(12) United States Patent
Hidaka et al.

(10) Patent No.: US 8,951,997 B2
(45) Date of Patent: Feb. 10, 2015

(54) SUBSTITUTED ISOQUINOLINE DERIVATIVE

(75) Inventors: Hiroyoshi Hidaka, Nagoya (JP); Kouichi Takahashi, Nagoya (JP); Yoshihiro Inoue, Nagoya (JP); Kengo Sumi, Nagoya (JP); Ryohei Nakamura, Nagoya (JP)

(73) Assignee: D. Western Therapeutics Institute, Inc., Nagoya-shi (JP)

( * ) Notice: Subject to any disclaimer, the term of this patent is extended or adjusted under 35 U.S.C. 154(b) by 346 days.

(21) Appl. No.: 13/265,246

(22) PCT Filed: Jun. 18, 2010

(86) PCT No.: PCT/JP2010/004101
§ 371 (c)(1),
(2), (4) Date: Oct. 19, 2011

(87) PCT Pub. No.: WO2010/146881
PCT Pub. Date: Dec. 23, 2010

(65) Prior Publication Data
US 2012/0035159 A1 Feb. 9, 2012

(30) Foreign Application Priority Data
Jun. 19, 2009 (JP) ................................ 2009-146040

(51) Int. Cl.
| C07D 403/12 | (2006.01) |
| A61K 31/47 | (2006.01) |
| A61K 31/551 | (2006.01) |
| A61K 31/407 | (2006.01) |
| A61K 31/4725 | (2006.01) |
| A61K 31/496 | (2006.01) |
| A61K 31/5377 | (2006.01) |
| C07D 217/02 | (2006.01) |
| C07D 401/12 | (2006.01) |
| C07D 487/08 | (2006.01) |

(52) U.S. Cl.
CPC ........... *A61K 31/407* (2013.01); *A61K 31/4725* (2013.01); *A61K 31/496* (2013.01); *A61K 31/5377* (2013.01); *A61K 31/551* (2013.01); *C07D 217/02* (2013.01); *C07D 401/12* (2013.01); *C07D 487/08* (2013.01)
USPC .......................................... 514/183; 540/470

(58) Field of Classification Search
None
See application file for complete search history.

(56) References Cited

U.S. PATENT DOCUMENTS

| 4,456,757 A | 6/1984 | Hidaka et al. |
| 4,525,589 A | 6/1985 | Hidaka et al. |
| 4,560,755 A | 12/1985 | Hidaka et al. |
| 4,634,770 A | 1/1987 | Hidaka et al. |
| 4,678,783 A | 7/1987 | Hidaka et al. |
| 4,709,032 A | 11/1987 | Hidaka et al. |
| 4,798,897 A | 1/1989 | Hidaka et al. |
| 4,943,581 A | 7/1990 | Hidaka et al. |
| 5,216,150 A | 6/1993 | Hidaka et al. |
| 5,244,895 A | 9/1993 | Hidaka et al. |
| 5,245,034 A | 9/1993 | Hidaka et al. |
| 6,153,608 A | 11/2000 | Hidaka et al. |
| 7,067,507 B2 * | 6/2006 | Pulley et al. .................. 514/183 |
| 7,517,991 B2 | 4/2009 | Sher et al. |
| 7,572,913 B2 | 8/2009 | McKerracher et al. |
| 2005/0272723 A1 | 12/2005 | Glick |
| 2006/0079556 A1 | 4/2006 | Sher et al. |
| 2007/0088021 A1 | 4/2007 | Hidaka et al. |
| 2007/0179127 A1 | 8/2007 | Yamada et al. |
| 2008/0064681 A1 | 3/2008 | Hidaka et al. |
| 2009/0048223 A1 | 2/2009 | Matsubara et al. |
| 2009/0306053 A1 | 12/2009 | Hidaka et al. |

FOREIGN PATENT DOCUMENTS

| WO | 2005 080394 | 9/2005 |
| WO | 2006 073448 | 7/2006 |

(Continued)

OTHER PUBLICATIONS

"Glaucoma", http://www.mayoclinic.com/health/glaucoma/DS00283/METHOD=print&DSECTION=all, accessed Nov. 26, 2013.*

(Continued)

*Primary Examiner* — Noble Jarrell
(74) *Attorney, Agent, or Firm* — Oblon, Spivak, McClelland, Maier & Neustadt, L.L.P.

(57) ABSTRACT

The present invention provides an isoquinoline-6-sulfonamide derivative that is useful as a novel pharmaceutical agent. The present invention provides an isoquinoline-6-sulfonamide derivative represented by Formula (1), a salt thereof, or a solvate of the derivative or the salt: wherein X and Y each independently represent a direct bond, NH, CH=CH, O, or S; $R^1$ and $R^2$ each independently represent a hydrogen atom, a halogen atom, a cyano group, an alkyl group, or the like; $R^3$ and $R^4$ each independently represent a hydrogen atom, an alkyl group, or the like, or $R^3$ and $R^4$ together form an alkylene group or an alkenylene group, which may be bridged between two carbon atoms to an arbitrary position; and l, m, and n represent an integer number of 1 to 4.

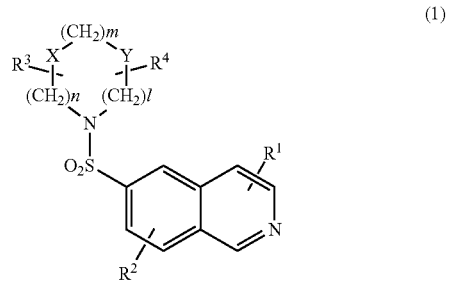

14 Claims, No Drawings

(56) References Cited

FOREIGN PATENT DOCUMENTS

| WO | 2008/077554 | 7/2008 |
| WO | 2008 105442 | 9/2008 |

OTHER PUBLICATIONS

"Spinal Cord Injury", http://www.mayoclinic.com/health/spinal-cord-injury/DS00460/METHOD=print&DSEC . . . , accessed Nov. 26, 2013.*

Lizarzaburu, E.M., et al., "Convenient preparation of aryl ether derivatives using a sequence of functionalized polymers," Tetrahedron Letters, vol. 44, pp. 4873-4876, (2003).

International Search Report Issued Jul. 13, 2010 in PCT/JP10/004101 Filed Jun. 18, 2010.

U.S. Appl. No. 09/673,246, filed Oct. 23, 2000, Hidaka, et al.

Office Action as received in the corresponding Taiwanese Patent Application No. 099120004 dated Jul. 28, 2014.

Extended European Search Report issued Oct. 30, 2012 in European Patent Application No. 10789260.6.

H. Fukao, et al., "Effects of fibrin on the secretion of plasminogen activator inhibitor-1 from endothelial cells and on protein kinase c", Life Sciences, vol. 57, No. 13, XP55041979, Aug. 1, 1995, pp. 1267-1276.

* cited by examiner

SUBSTITUTED ISOQUINOLINE DERIVATIVE

This application is a National Stage of PCT/JP10/004101 filed Jun. 18, 2010 and claims the benefit of JP 2009-146040 filed Jun. 19, 2009.

FIELD OF THE INVENTION

The present invention relates to isoquinoline-6-sulfonamide derivatives that are useful for the prevention and/or treatment of glaucoma, cardiovascular diseases, or diseases or disorders caused by neurodegeneration or nerve injury.

BACKGROUND OF THE INVENTION

Among compounds having an isoquinoline skeleton, there exist a number of compounds useful as pharmaceuticals. However, a few reports have made mention of compounds having an isoquinoline skeleton substituted at the 6th position by an aminosulfonyl group, which include cannabinoid receptor antagonists disclosed in Patent Document 1, mitochondrial F1F0 ATPase inhibitors disclosed in Patent Document 2, and a method for producing a compound having a phenoxy group disclosed in Non Patent Document 1.

RELATED ART DOCUMENT

Patent Document

[Patent Document 1] U.S. Patent Publication No. US-20060079556
[Patent Document 2] WO2006/073448

Non Patent Document

[Non Patent Document 1] Tetrahedron Letters 44, 4873-4876 (2003)

SUMMARY OF THE INVENTION

Problem to be Solved by the Invention

An object of the present invention is to provide novel isoquinoline-6-sulfonamide derivatives that are useful as pharmaceuticals.

Solution to Problem

The present inventor conducted a study to introduce various substituents to the 6th position of an isoquinoline skeleton and used 6-chlorosulfonylisoquinoline as a key intermediate to synthesize various novel isoquinoline-6-sulfonamide derivatives represented by Formula (1) described below. As a result of studying the pharmacological effects of these compounds, it was found that they have excellent ocular hypotensive effect, blood pressure lowering effect, neurite outgrowth promoting effect, and so on. They are useful as active ingredients for the prevention or treatment of glaucoma, cardiovascular diseases, or diseases or disorders caused by neurodegeneration or nerve injury.

Specifically, the present invention provides isoquinoline-6-sulfonamide derivatives represented by Formula (1), salts thereof, or solvates of the derivative or the salt:

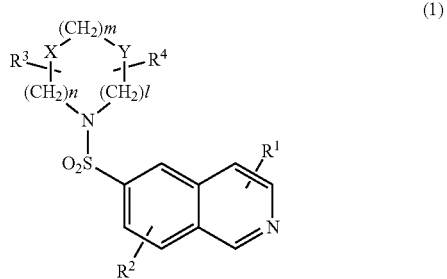

(1)

wherein
X and Y each independently represent a direct bond, NH, CH=CH, O, or S;
$R^1$ and $R^2$ each independently represent a hydrogen atom, a halogen atom, a cyano group, an alkyl group, a halogenoalkyl group, an alkenyl group, an alkoxy group, an alkylthio group, a hydroxyl group, a mercapto group, a nitro group, an aryl group, an amino group, or an aminoalkylthio group;
$R^3$ and $R^4$ each independently represent a hydrogen atom, an alkyl group, an alkenyl group, an amino group, an alkylamino group, a dialkylamino group, an aminoalkyl group, a halogenoalkyl group, an alkanoyl group, an aminoalkanoyl group, an alkylaminoalkanoyl group, an alkoxycarbonyl group, a hydroxyl group, or a mercapto group, or $R^3$ and $R^4$ together form an alkylene group or an alkenylene group, which may be bridged between two carbon atoms to an arbitrary position; and
l, m, and n represent a number of 1 to 4.

Moreover, the present invention provides pharmaceutical compositions containing an isoquinoline-6-sulfonamide derivative represented by Formula (1), a salt thereof, or a solvate of the derivative or the salt.

Moreover, the present invention provides isoquinoline-6-sulfonamide derivatives represented by Formula (1), salts thereof, or solvates of the derivative or the salt for preventing or treating glaucoma, cardiovascular diseases, or diseases or disorders caused by neurodegeneration or nerve injury.

Furthermore, the present invention provides a method for preventing or treating glaucoma, cardiovascular diseases, or diseases or disorders caused by neurodegeneration or nerve injury, including administering an effective amount of an isoquinoline-6-sulfonamide derivative represented by Formula (1), a salt thereof, or a solvate of the derivative or the salt.

Effects of the Invention

Isoquinoline-6-sulfonamide derivatives of the present invention have excellent ocular hypotensive effect, blood pressure lowering effect, vasodilating effect, neurite outgrowth promoting effect, and the like, and are useful as an active ingredient for the prevention or treatment of glaucoma, cardiovascular diseases, or diseases or disorders caused by neurodegeneration or nerve injury.

MODE FOR CARRYING OUT THE INVENTION

In Formula (1), X and Y each independently represent a direct bond, NH, CH=CH, O, or S. X is more preferably a direct bond or NH, particularly preferably NH. Moreover, Y is more preferably a direct bond, NH, CH=CH, or O, particularly preferably a direct bond, CH=CH, or O.

$R^1$ and $R^2$ each independently represent a hydrogen atom, a halogen atom, a cyano group, an alkyl group, a halogenoalkyl group, an alkenyl group, an alkoxy group, an alkylthio group, a hydroxyl group, a mercapto group, a nitro group, an aryl group, an amino group, or aminoalkylthio group.

Examples of the halogen atom include fluorine, chlorine, bromine, and iodine atoms. Of them, a fluorine, chlorine, or bromine atom is preferable.

Examples of the alkyl group include linear, branched, or cyclic alkyl groups having 1 to 8 carbon atoms ($C_{1-8}$ alkyl groups). Alkyl groups having 1 to 6 carbon atoms are preferable, with alkyl groups having 1 to 3 carbon atoms further preferred.

Specific examples thereof can include methyl, ethyl, n-propyl, isopropyl, n-butyl, isobutyl, sec-butyl, tert-butyl, n-pentyl, isopentyl, n-hexyl, isohexyl, and cyclopropyl groups. Among them, those having 1 to 3 carbon atoms are preferable, with a methyl or ethyl group particularly preferred.

The halogenoalkyl group is preferably a halogeno $C_{1-8}$ alkyl group, more preferably a halogeno $C_{1-6}$ alkyl group. Specific examples thereof include chloromethyl, fluoromethyl, chloroethyl, fluoroethyl, and trifluoromethyl groups.

Examples of the alkenyl group include linear or branched alkenyl groups having 2 to 8 carbon atoms ($C_{2-8}$ alkenyl groups). Alkenyl groups having 2 to 6 carbon atoms are preferable. Specific examples thereof can include vinyl, allyl, isopropenyl, 2-methallyl, 2-butenyl, and 3-butenyl groups. Among them, those having 2 to 4 carbon atoms are preferable.

Examples of the alkoxy group include linear or branched alkoxy groups having 1 to 8 carbon atoms ($C_{1-8}$ alkoxy groups). Alkoxy groups having 1 to 6 carbon atoms are preferable. Specific examples thereof can include methoxy, ethoxy, n-propoxy, isopropoxy, n-butoxy, isobutoxy, sec-butoxy, and tert-butoxy groups.

Examples of the alkylthio group include linear or branched alkylthio groups having 1 to 8 carbon atoms ($C_{1-8}$ alkylthio groups). Alkylthio groups having 1 to 6 carbon atoms are preferable. Specific examples thereof include methylthio, ethylthio, isopropylthio, and n-propylthio groups.

Examples of the aryl group include $C_{6-14}$ aryl groups. Phenyl and naphthyl groups are preferable, with a phenyl group more preferred.

The aminoalkylthio group is preferably an amino-$C_{1-8}$ alkylthio group, more preferably an amino-$C_{1-6}$ alkylthio group. Specific examples thereof include aminomethylthio, aminoethylthio, and aminopropylthio groups.

Preferably, $R^1$ and $R^2$ are each independently a hydrogen atom, a halogen atom, a $C_{1-8}$ alkyl group, a nitro group, a cyano group, a halogeno $C_{1-8}$ alkyl group, a phenyl group, a $C_{2-8}$ alkenyl group, a hydroxyl group, an amino group, or an amino $C_{1-8}$ alkylthio group. Moreover, more preferably, they are each independently a hydrogen atom, a halogen atom, a cyano group, a $C_{1-6}$ alkyl group, or a halogeno $C_{1-6}$ alkyl group. Further preferably, they are each independently a hydrogen atom, a halogen atom, or a $C_{1-3}$ alkyl group.

$R^1$ may be substituted at any of the 1st, 3rd, and 4th positions of the isoquinoline skeleton. Moreover, $R^2$ may be substituted at any of the 5th, 7th, and 8th positions of the isoquinoline skeleton.

$R^3$ and $R^4$ each independently represent a hydrogen atom, an alkyl group, an alkenyl group, an amino group, an alkylamino group, a dialkylamino group, an aminoalkyl group, a halogenoalkyl group, an alkanoyl group, an aminoalkanoyl group, an alkylaminoalkanoyl group, an alkoxycarbonyl group, a hydroxyl group, or a mercapto group, or $R^3$ and $R^4$ together form an alkylene group or an alkenylene group, which may be bridged between two carbon atoms to an arbitrary position.

Examples of the alkyl group, the alkenyl group, and the halogenoalkyl group include those illustrated above as examples of $R^1$ and $R^2$.

The alkylamino group is preferably a $C_{1-8}$ alkylamino group. Specific examples thereof include methylamino, ethylamino, n-propylamino, isopropylamino, n-butylamino, isobutylamino, sec-butylamino, n-pentylamino, and n-hexylamino groups. The dialkylamino group is preferably a di-$C_{1-8}$ alkylamino group. Specific examples thereof include dimethylamino, diethylamino, dipropylamino, and dibutylamino groups. The aminoalkyl group is preferably an amino $C_{1-8}$ alkyl group. Specific examples thereof include aminomethyl, aminoethyl, aminopropyl, and aminobutyl groups.

Examples of the alkanoyl group include linear or branched alkanoyl groups having 2 to 8 carbon atoms ($C_{2-8}$ alkanoyl groups). Alkanoyl groups having 2 to 6 carbon atoms are preferable. Specific examples thereof include acetyl, propionyl, and butyryl groups. Examples of the aminoalkanoyl group include amino-$C_{2-8}$ alkanoyl groups. Amino-$C_{2-6}$ alkanoyl groups are preferable. Specific examples thereof include aminoacetyl, aminopropionyl, and aminobutyryl groups.

Examples of the alkylaminoalkanoyl group include $C_{1-8}$ alkylamino $C_{2-8}$ alkanoyl groups. $C_{1-4}$ alkylamino $C_{2-4}$ alkanoyl groups are preferable. Specific examples thereof include methylaminoacetyl and methylaminopropionyl groups. Examples of the alkoxycarbonyl group include $C_{1-8}$ alkoxycarbonyl groups, for example, methoxycarbonyl and ethoxycarbonyl groups.

These $R^3$ and $R^4$ moieties may be substituted at any position of the cyclic amino group in Formula (1) and are preferably substituted on the carbon atom or on the nitrogen or carbon atom when X and Y are NH or CH=CH, more preferably on the carbon atom.

Examples of the alkylene group formed by $R^3$ and $R^4$ together include $C_{1-3}$ alkylene groups, for example, methylene, ethylene, and trimethylene (—$CH_2CH_2CH_2$—) groups. Particularly, methylene and ethylene groups are preferable. Examples of the alkenylene group formed by $R^3$ and $R^4$ together include $C_{2-4}$ alkenylene groups, for example, —CH=CH— and —$CH_2$CH=CH—. This alkylene or alkenylene group may be bridged between two carbon atoms to an arbitrary position on the nitrogen-containing saturated heterocyclic ring in Formula (1). Such bridging is preferably bridging based on a bridged $C_{1-3}$ alkylene group, i.e., —$CH_2$—, —$CH_2CH_2$—, or —$CH_2CH_2CH_2$—.

Preferably, $R^3$ and $R^4$ each independently represent a hydrogen atom, a $C_{1-8}$ alkyl group, a $C_{2-8}$ alkenyl group, an amino group, an amino $C_{1-8}$ alkyl group, a halogeno $C_{1-8}$ alkyl group, a $C_{1-8}$ alkylamino group, a di-$C_{1-8}$ alkylamino group, a $C_{2-8}$ alkanoyl group, an amino $C_{2-8}$ alkanoyl group, a $C_{1-8}$ alkoxycarbonyl group, a hydroxyl group, or a mercapto group, or $R^3$ and $R^4$ together form a bridged $C_{1-3}$ alkylene group.

Moreover, more preferably, $R^3$ and $R^4$ are each independently a hydrogen atom, a $C_{1-8}$ alkyl group, an amino group, a $C_{1-8}$ alkylamino group, an amino $C_{1-8}$ alkyl group, or a halogeno $C_{1-8}$ alkyl group, or $R^3$ and $R^4$ together form a bridged $C_{1-3}$ alkylene group.

Further preferably, $R^3$ and $R^4$ are a hydrogen atom, a $C_{1-6}$ alkyl group, or a halogeno $C_{1-6}$ alkyl group.

When $R^3$ and $R^4$ are substituted on the nitrogen atom of NH as X and/or Y in Formula (1), the substituent is preferably a hydrogen atom, a $C_{1-8}$ alkyl group, a $C_{2-8}$ alkenyl group, a halogeno $C_{1-8}$ alkyl group, a $C_{2-8}$ alkanoyl group, an amino $C_{2-8}$ alkanoyl group, an amino $C_{1-8}$ alkyl group, a $C_{2-8}$ alkanoyl group, or a $C_{1-8}$ alkoxycarbonyl group.

l, m, and n represent a number of 1 to 4. l and m are each independently preferably a number of 1 to 3. Moreover, n is preferably a number of 2 to 3, particularly preferably 2.

Specific examples of the nitrogen-containing heterocyclic ring in Formula (1) can include pyrrolidino, imidazolidinyl, piperidino, piperazino, morpholino, thiomorpholino, 1,4-diazepanyl, 1,4-diazocanyl, 1,4-diazononyl, 1,4-diazecanyl, 1,5-diazecanyl, tetrahydro-1,4-diazepinyl, hexahydro-1,4-diazocinyl, 1,4,7-oxadiazonanyl, 1,4,7-thiadiazonanyl, 1,4, 7-triazonanyl, 3,6-diazabicyclo[3.2.2]nonan-3-yl, 3,6-diazabicyclo[3.2.1]octan-3-yl, 2,5-diazabicyclo[2.2.1]heptan-2-yl, and 2,5-diazabicyclo[2.2.2]octan-2-yl.

Preferable examples of the compound of Formula (1) include the following compounds:

a compound selected from the group consisting of the following, a salt thereof, or a solvate thereof:

6-(piperazin-1-ylsulfonyl)isoquinoline,
(R)-6-(3-aminopyrrolidin-1-ylsulfonyl)isoquinoline,
6-(1,4-diazepan-1-ylsulfonyl)isoquinoline,
6-(4-aminopiperidin-1-ylsulfonyl)isoquinoline,
5-bromo-6-(1,4-diazepan-1-ylsulfonyl)isoquinoline,
6-(1,4-diazepan-1-ylsulfonyl)-8-fluoroisoquinoline,
6-{(1S,4S)-2,5-diazabicyclo[2.2.1]heptan-2-ylsulfonyl}isoquinoline,
(R,Z)-6-(2-methyl-2,3,4,5-tetrahydro-1,4-diazocin-1(8H)-ylsulfonyl)isoquinoline,
6-(morpholin-1-ylsulfonyl)isoquinoline,
(S)-6-{3-(N-methylamino)pyrrolidin-1-ylsulfonyl}isoquinoline,
(S)-6-{3-(N-butylamino)pyrrolidin-1-ylsulfonyl}isoquinoline,
(S)-6-(2-methyl-1,4-diazepan-1-ylsulfonyl)isoquinoline,
(S)-6-(2-methylpiperazin-1-ylsulfonyl)isoquinoline,
(R)-6-(2-methyl-1,4-diazocan-1-ylsulfonyl)isoquinoline,
(S)-5-bromo-6-(2-methyl-1,4-diazepan-1-ylsulfonyl)isoquinoline,
6-(3-methyl-1,4-diazepan-1-ylsulfonyl)isoquinoline,
6-(7-methyl-1,4-diazepan-1-ylsulfonyl)isoquinoline,
(R)-6-(2-methyl-1,4-diazepan-1-ylsulfonyl)isoquinoline,
(R)-6-(2-ethyl-1,4-diazepan-1-ylsulfonyl)isoquinoline,
(R)-6-(2-ethyl-1,4-diazocan-1-ylsulfonyl)isoquinoline,
6-(1,4-diazocan-1-ylsulfonyl)isoquinoline,
6-(2,2-dimethyl-1,4-diazepan-1-ylsulfonyl)isoquinoline,
(R)-5-bromo-6-(2-methyl-1,4-diazocan-1-ylsulfonyl)isoquinoline,
(S)-6-(2-methyl-1,4-diazocan-1-ylsulfonyl)isoquinoline,
(R)-6-(2-methyl-1,4-diazepan-1-ylsulfonyl)-7-fluoroisoquinoline,
(S)-6-(2-fluoromethyl-1,4-diazepan-1-ylsulfonyl)isoquinoline,
(S)-6-(2-fluoromethyl-1,4-diazocan-1-ylsulfonyl)isoquinoline,
(S)-6-(2-methyl-1,4-diazonan-1-ylsulfonyl)isoquinoline,
(R)-5-bromo-6-(2-methyl-1,4-diazepan-1-ylsulfonyl)isoquinoline,
(R)-6-(6-methyl-1,4-diazocan-1-ylsulfonyl)isoquinoline,
(R)-6-(7-methyl-1,4-diazocan-1-ylsulfonyl)isoquinoline,
(S)-6-(7-methyl-1,4-diazepan-1-ylsulfonyl)isoquinoline,
(R)-6-(2-methyl-1,4-diazonan-1-ylsulfonyl)isoquinoline,
(R)-6-(7-methyl-1,4-diazepan-1-ylsulfonyl)isoquinoline,
(2R,7R)-6-(2,7-dimethyl-1,4-diazepan-1-ylsulfonyl)isoquinoline,
(2S,7R)-6-(2,7-dimethyl-1,4-diazepan-1-ylsulfonyl)isoquinoline,
(R)-6-(8-methyl-1,4-diazocan-1-ylsulfonyl)isoquinoline,
(R)-6-(2-methyl-1,5-diazocan-1-ylsulfonyl)isoquinoline,
(R)-6-(2-methyl-1,4-diazocan-1-ylsulfonyl)-5-nitroisoquinoline,
(2R,6R)-6-(2,6-dimethylpiperazin-1-ylsulfonyl)isoquinoline,
(2S,7S)-6-(2,7-dimethyl-1,4-diazepan-1-ylsulfonyl)isoquinoline,
(S)-6-(2-methyl-1,5-diazocan-1-ylsulfonyl)isoquinoline,
(R)-6-(5-methyl-1,4,7-oxadiazonan-4-ylsulfonyl)isoquinoline,
(R)-6-(2-methyl-1,4,7-triazonan-1-ylsulfonyl)isoquinoline,
6-(4-glycyl-1,4-diazepan-1-ylsulfonyl)isoquinoline,
(S)-6-(4-glycyl-2-methyl-1,4-diazepan-1-ylsulfonyl)isoquinoline,
(R)-6-(4-glycyl-2-methyl-1,4-diazocan-1-ylsulfonyl)isoquinoline,
(R)-6-(4-sarcosyl-2-methyl-1,4-diazocan-1-ylsulfonyl)isoquinoline,
(S)-5-methyl-6-(2-methyl-1,4-diazepan-1-ylsulfonyl)isoquinoline,
(S)-1-(2-aminoethylthio)-6-(2-methyl-1,4-diazepan-1-ylsulfonyl)isoquinoline,
(R)-1-(2-aminoethylthio)-6-(7-methyl-1,4-diazepan-1-ylsulfonyl)isoquinoline,
(R)-1-(2-aminoethylthio)-6-(2-methyl-1,4-diazocan-1-ylsulfonyl)isoquinoline,
6-(1,4-diazepan-1-ylsulfonyl)isoquinolin-1(2H)-one,
1-amino-6-(1,4-diazepan-1-ylsulfonyl)isoquinoline,
1-nitrile-6-(1,4-diazepan-1-ylsulfonyl)isoquinoline,
(S)-6-(2-(4-aminobutyl)-1,4-diazepin-1-ylsulfonyl)isoquinoline,
6-(4-methoxycarbonylpiperidin-1-ylsulfonyl)isoquinoline,
(S)-6-(3-hydroxypyrrolidin-1-ylsulfonyl)isoquinoline, and
5-phenyl-6-(1,4-diazepan-1-ylsulfonyl)isoquinoline.

A salt of the compound (1) of the present invention needs only to be a pharmaceutically acceptable salt, and examples thereof include acid-addition salts. Specific examples thereof can include salts of inorganic acids (e.g., hydrochloric acid, sulfuric acid, nitric acid, phosphoric acid, hydrofluoric acid, and hydrobromic acid) and salts of organic acids (e.g., acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, and camphorsulfonic acid).

The compound (1) of the present invention can be produced by, for example, the following methods:

Production Method 1

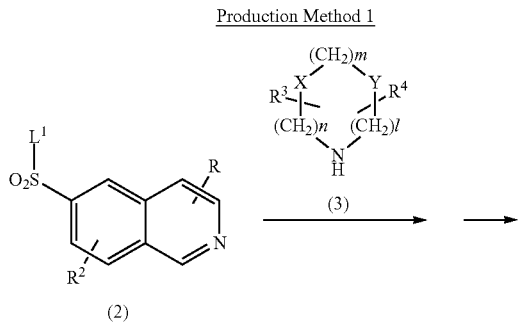

-continued

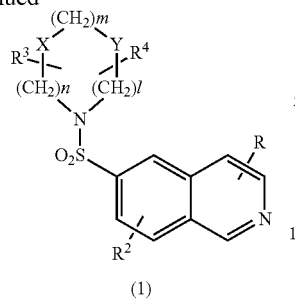

(1)

wherein $L^1$ represents a hydroxyl or a leaving group; and $R^1$ to $R^4$, X, Y, l, m, and n are the same as above.

Examples of $L^1$ as a leaving group can include a residue of a reactive derivative of sulfonic acid described later. Examples of a protective group used when X and Y are N can include: acyl groups such as formyl, acetyl, and benzoyl; aralkyloxycarbonyl groups such as benzyloxycarbonyl; alkoxycarbonyl groups such as tert-butyloxycarbonyl; and aralkyl groups such as benzyl. When X and Y are a direct bond, CH=CH, O, or S, a protective group is not required.

Amine represented by Formula (3) is reacted with sulfonic acid represented by Formula (2) or a reactive derivative thereof in an appropriate solvent, and the protective group is removed, if necessary, to produce a compound (1). Any reaction solvent that does not hinder the reaction can be used and is, for example, ethers (e.g., tetrahydrofuran, dioxane, and diethyl ether), hydrocarbons (e.g., benzene and toluene), halogenated hydrocarbons (e.g., methylene chloride and chloroform), aprotic solvents (e.g., N,N-dimethylformamide and N,N-dimethylacetamide), pyridine, acetonitrile, or a mixture thereof can be used.

Sulfonic acid halide (e.g., sulfonic acid chloride and sulfonic acid bromide), sulfonic anhydride, N-sulfonylimidazolide, or the like is used as the reactive derivative of sulfonic acid. Particularly, sulfonic acid halide is preferable.

The present reaction is preferably performed in the presence of an appropriate base. Alkali such as alkali metal bicarbonate (e.g., sodium bicarbonate), alkali metal carbonate (e.g., potassium carbonate), alkali metal hydroxide (e.g., sodium hydroxide and potassium hydroxide), and organic tertiary amine such as triethylamine and triethylenediamine can be used as such a base. When a basic solvent such as pyridine is used as the solvent, such a base is not required. This case is preferable.

The present reaction usually proceeds at room temperature in many cases and can be performed, if necessary, by cooling or heating at −78 to 150° C., preferably 0 to 120° C. When the base is used, the amount of the reactive derivative (2) used is preferably in the range of 1- to 10-fold moles, more preferably 1- to 3-fold moles, with respect to the amine (3). The amount of the base used is preferably in the range of 1- to 10-fold moles, more preferably 1- to 3-fold moles, with respect to the amine (3). When the base is not used, the amount of the sulfonic acid or reactive derivative (2) used is a mole equal to or smaller than the amine (3), more preferably in the range of 0.5- to 0.1-fold moles, with respect to the amine (3). The reaction time differs depending on the starting material used, solvents, reaction temperatures, etc., and is usually 5 minutes to 70 hours. Subsequently, the protective group is removed, if necessary, by a method known per se in the art.

Production Method 2

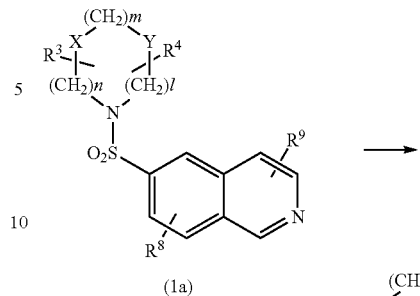

(1a)

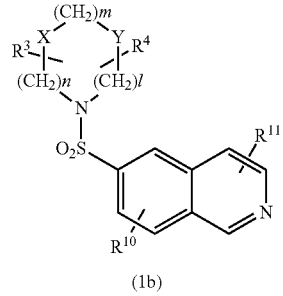

(1b)

wherein $R^8$ and $R^9$ each independently represent a hydrogen atom, a halogen atom, or a trifluoromethanesulfonyloxy group, and when either of them is a hydrogen atom, the other moiety represents a halogen atom or a trifluoromethanesulfonyloxy group; $R^{10}$ represents those defined above in $R^2$ except for a halogen atom; $R^{11}$ represents those defined above in $R^1$ except for a halogen atom; and $R^3$, $R^4$, X, Y, l, m, and n are the same as above.

The halogen represented by $R^8$ and $R^9$ is preferably chlorine or bromine.

A halogen form represented by Formula (1a) is treated with a Grignard reagent corresponding to $R^{10}$ and $R^{11}$, alkali such as organic metal reagents (e.g., alkyllithium), alkali metal hydroxide (e.g., sodium hydroxide and potassium hydroxide) or sodium alcoholate (e.g., sodium methylate and sodium ethylate), or potassium cyanide to produce a compound (1b). The present reaction can be performed according to a method known in the art.

Moreover, the compound (1b) can also be synthesized using Suzuki-Miyaura coupling performed in the presence of a palladium catalyst.

A compound (1d) wherein the nitrogen-containing heterocyclic ring in Formula (1) is cyclic diamino can also be produced as follows:

Production Method 3

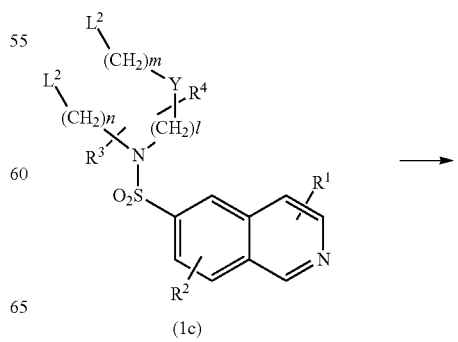

(1c)

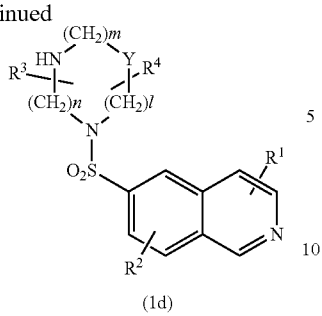

(1d)

wherein $L^2$ represents a leaving group; and $R^1$ to $R^4$, Y, l, m, and n are the same as above.

Examples of $L^2$ as a leaving group can include: halogen such as chlorine and bromine; and acyloxy groups such as, acetyloxy, mesyloxy, and tosyloxy.

A compound (1c) is reacted with amine, guanidine, or ammonia corresponding to X to produce a compound (1d). The present reaction can be performed according to a method known in the art (Acta Chemica Scand., 45, 621 (1991)).

Production Method 4

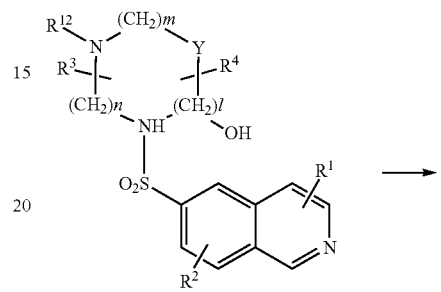

wherein $R^{12}$ represents a hydrogen atom or a protective group for the amino group; and $L^2$, $R^1$ to $R^4$, Y, l, m, and n are the same as above.

A compound (1e) is reacted with a compound (1f), and the protective group is removed, if necessary, by acid or alkali treatment to produce a compound (1d). The present reaction can be performed according to a method known in the art (Acta Chemica Scand., 45, 621 (1991)).

Production Method 5

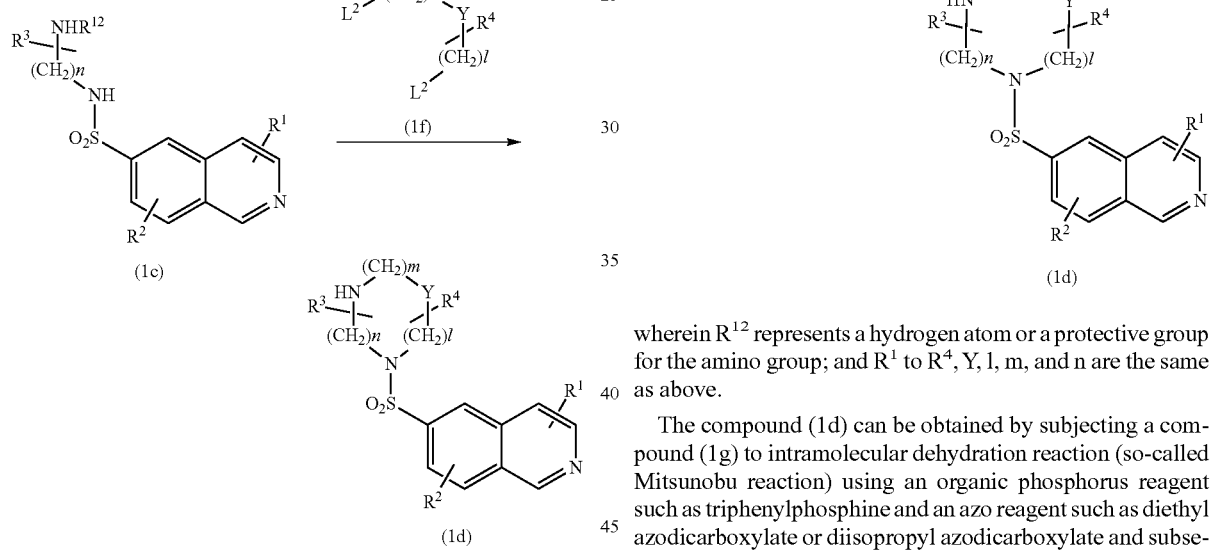

wherein $R^{12}$ represents a hydrogen atom or a protective group for the amino group; and $R^1$ to $R^4$, Y, l, m, and n are the same as above.

The compound (1d) can be obtained by subjecting a compound (1g) to intramolecular dehydration reaction (so-called Mitsunobu reaction) using an organic phosphorus reagent such as triphenylphosphine and an azo reagent such as diethyl azodicarboxylate or diisopropyl azodicarboxylate and subsequently removing the protective group $R^{12}$.

Production Method 6

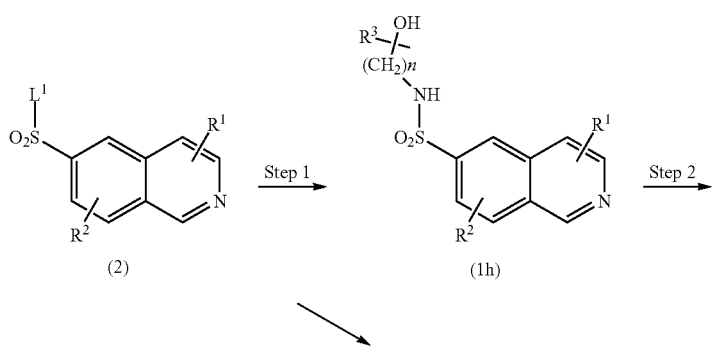

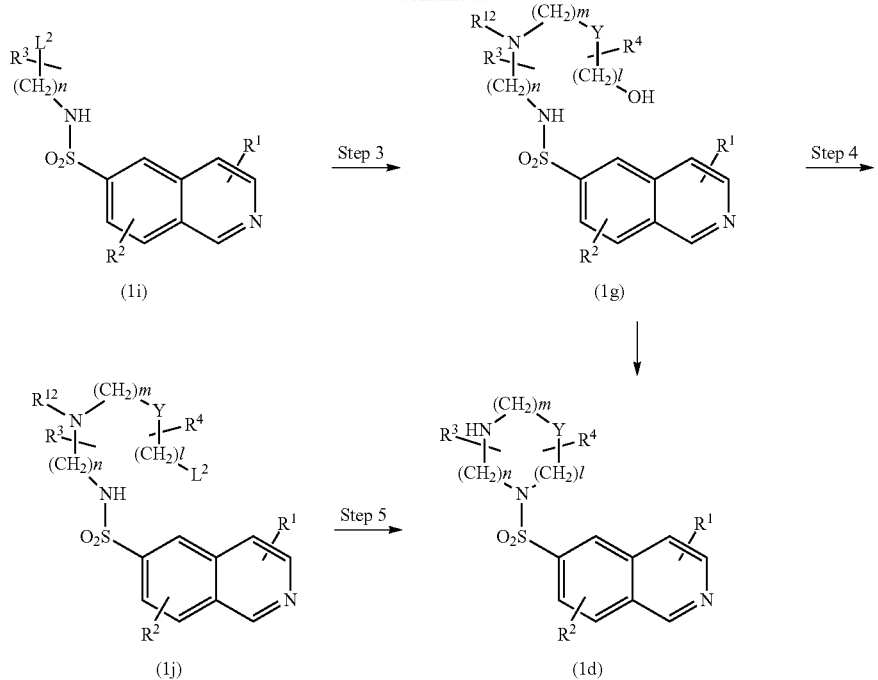

wherein $R^{12}$ represents a hydrogen atom or a protective group for the amino group; and $R^1$ to $R^4$, Y, l, m, n, $L^1$, and $L^2$ are the same as above.

(Step 1) An aminoalkyl alcohol and a compound (2) are reacted in the same way as in Production Method 1 to produce a compound (1h).

(Step 2) The hydroxyl group of the compound (1h) is converted to halogen (e.g., chlorine and bromine) or acyloxy (e.g., tosyloxy, methanesulfonyloxy, and acetyloxy) by a method known per se in the art, and then, a compound (1i) is produced.

(Step 3) The compound (1i) and aminoalkyl alcohol are reacted in the same way as in Production Method 1 in the presence or absence of a base in an appropriate solvent to produce a compound (1g).

Moreover, the compound (1g) may be synthesized in one step by reacting the compound (2) with corresponding amino alcohol.

(Step 4) The nitrogen atom in the secondary amino of the compound (1g) is protected, if necessary, by a method known in the art, and then, the compound (1g) can be converted to a compound (1j) according to a standard method.

(Step 5) The compound (1j) is treated with a base in an appropriate solvent, and the protective group is removed, if necessary, by acid or alkali treatment to produce a compound (1d). Alkali (e.g., sodium hydride, sodium bicarbonate, potassium carbonate, sodium hydroxide, and potassium hydroxide) or organic tertiary amine (e.g., triethylamine and triethylenediamine) can be used as the base. The reaction is performed under the same reaction conditions as in Production Method 1 using the reaction solvent exemplified in Production Method 1.

Moreover, the compound (1d) can also be synthesized by intramolecular dehydration reaction (so-called Mitsunobu reaction) and subsequent deprotection of $R^{12}$ according to Production Method 5.

In these production methods, the hydroxyl or amino group is protected, if necessary, with a protective group usually used, and the protective group can be removed by a method known per se in the art such as acid treatment, alkali treatment, or catalytic reduction after the reaction. For example, benzyl, benzyloxycarbonyl, or trifluoroacetyl can be used as a protective group for the amino group. Methoxymethyl, 2-methoxyethoxymethyl, methylthiomethyl, tetrahydropyranyl, tert-butyl, benzyl, trimethylsilyl, tert-butyldimethylsilyl, or the like can be used as a protective group for the hydroxyl group. When the hydroxyl group is protected with a benzyl group, it also undergoes debenzylation during catalytic reduction to form a free hydroxyl group.

The starting material (2) can be produced using commercially available 6-aminoisoquinoline (2d) or 6-bromoisoquinoline (2c). In addition, it can also be synthesized by a method shown below.

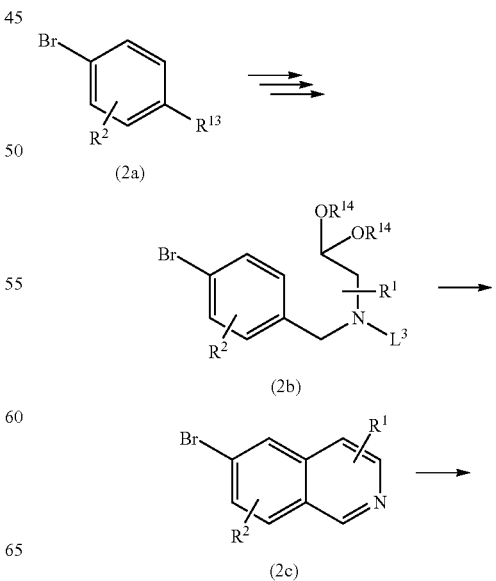

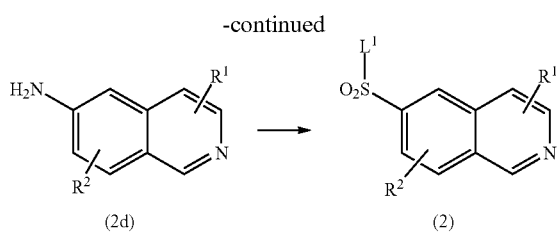

wherein $R^{14}$ represents an alkyl group; $L^3$ represents a leaving group such as a methanesulfonyl group or a toluenesulfonyl group; and $R^1$, $R^2$, and $L^1$ are the same as above.

In Formula, examples of $R^{13}$ can include a formyl group, a halomethyl group, halogen, and acyloxymethyl such as acetyloxymethyl, mesyloxymethyl, and tosyloxymethyl. When $R^{13}$ is a formyl group, secondary amine can be synthesized by reductive amination and then reacted with sulfonyl halide typified by tosyl and mesyl groups to produce a compound (2b). When $R^{13}$ is a halomethyl group, halogen, or acyloxymethyl such as acetyloxymethyl, mesyloxymethyl, or tosyloxymethyl, the compound (2b) can be synthesized through substitution reaction by amine. The compound (2b) can be reacted in the presence of strong acid and Lewis acid to produce a compound (2c). A compound (2) can be synthesized from the compound (2c) using a method known in the art.

Some compounds of the present invention have asymmetric carbon and include optical isomers. Each of these isomers and any of their mixtures are also encompassed by the present invention. They are usually obtained as racemic bodies. These racemic bodies have pharmacological activity in themselves and can be resolved into each isomer, if desired. For example, an isomeric mixture can be resolved by an optical resolution method known in the art, for example, a method involving generating a salt with optically active carboxylic acid (e.g., (+)- or (−)-tartaric acid or (+)- or (−)-malic acid) or optically active sulfonic acid (e.g., (+)-camphorsulfonic acid), followed by fractional crystallization, or a method using an optically active column. Moreover, the optical isomer can be obtained using an optically active starting compound (S or R configuration).

The compound of the present invention can form the salt by a method known in the art. For example, hydrochloride of the compound of the present invention can be obtained by dissolving the compound of the present invention in an alcohol solution or ethyl ether solution of hydrogen chloride.

The compound of the present invention or the salt thereof may be recrystallized from an appropriate solvent (also including water) to obtain a solvate (also including a hydrate). These solvates are also included in the present invention. For example, hydrate of the compound of the present invention may be obtained by recrystallizing the compound of the present invention from hydrous alcohol.

The compound of the present invention may assume a crystal polymorph. This crystal polymorph is also included in the present invention.

The compound of the present invention thus produced can be isolated and purified in a free base form or acid-addition salt form by means known per se in the art, for example, concentration, liquid conversion, solvent conversion, solvent extraction, crystallization, fractionation, and chromatography.

The compound of the present invention has, as shown later in Examples, excellent ocular hypotensive effect, blood pressure lowering effect, vasodilating effect, neurite outgrowth promoting effect, and effect of recovering motor function after spinal cord injury. Thus, the compounds of the present invention are useful as therapeutic drugs for glaucoma, cardiovascular diseases, or diseases or disorders caused by neurodegeneration or nerve injury.

In this context, the glaucoma according to the present invention includes primary open-angle glaucoma, normal tension glaucoma, hypersecretion glaucoma, ocular hypertension, acute closed-angle glaucoma, chronic closed-angle glaucoma, mixed glaucoma, steroid-induced glaucoma, pigmentary glaucoma, exfoliation glaucoma, amyloidotic glaucoma, neovascular glaucoma, malignant glaucoma, capsular glaucoma, and plateau iris syndrome.

Moreover, the cardiovascular disease according to the present invention includes, but not limited to, hypertension, arteriosclerosis, cerebrovascular diseases, heart diseases, and peripheral vascular diseases.

More specifically, examples of the hypertension include essential hypertension, renal hypertension, renovascular hypertension, pregnancy-induced hypertension, endocrine hypertension, cardiovascular hypertension, neurogenic hypertension, iatrogenic hypertension, and pulmonary hypertension. Examples of the arteriosclerosis include those having a lesion in the main artery in the whole body, such as coronary artery/abdominal aorta/renal artery/carotid artery/ocular fundus artery/cerebral artery. Examples of the cerebrovascular diseases include cerebral thrombosis, cerebral infarction, cerebral hemorrhage, transient ischemic attack, hypertensive encephalopathy, cerebral arteriosclerosis, subdural hematoma, epidural hematoma, subarachnoid hemorrhage, brain hypoxia, brain edema, encephalitis, brain abscess, head injury, psychosis, metabolic poisoning, medicinal poisoning, transient cessation of breathing, and deep anesthesia during operation. The heart diseases includes congestive heart failure, acute myocardial infarction, old myocardial infarction, subendocardial infarction, right ventricular infarction, atypical myocardial infarction, ischemic cardiomyopathy, variant angina, stable angina, effort angina, coronary spastic angina, post-infarction angina, unstable angina, arrhythmia, and acute cardiac death.

The peripheral vascular disease includes: arterial disease such as Buerger disease, arteriosclerosis obliterans, and Raynaud's syndrome; venous disease such as phlebothrombosis and thrombophlebitis; and blood hyperviscosity syndrome, frostbite, cold feeling and sleep initiation disorder due to poor blood circulation, decubitus ulcer, chapped skin, and alopecia.

The diseases or disorders caused by neurodegeneration or nerve injury includes, but not limited to, disease associated with the central nervous system, for example, dementia, Alzheimer's disease, Parkinson's disease, progressive supranuclear palsy, subacute sclerosing panencephalitic Parkinsonism, postencephalitic parkinsonism, boxer's encephalopathy, Parkinsonism-dementia complex of Guam, Pick's disease, corticobasal degeneration, spinocerebellar degeneration, frontotemporal dementia, Huntington's disease, chronic neurodegeneration symptoms including AIDS-associated dementia, amyotrophic lateral sclerosis, multiple sclerosis, and neurotrauma (e.g., acute cerebral infarction, dysfunction after cerebral infarction, cerebral hemorrhage, traumatic brain damage, and spinal cord injury).

It also includes, but not limited to, disease associated with the peripheral nervous system, for example, trigeminal nerve disorder, facial nerve disorder, mononeuropathy, polyneuropathy, diabetic neuropathy, and traumatic nerve palsy.

It further includes, but not limited to, disease associated with the retinal nerve and optic nerve, for example, glaucoma, age-related macular degeneration, retinitis pigmentosa, diabetic retinopathy, neuroretinitis, optic neuritis, optic nerve avulsion, and traumatic optic neuropathy.

The compound of the present invention can be administered orally or parenterally. Examples of its dosage form include tablets, capsules, granules, powders, injections, and ophthalmic solutions. These dosage forms can be used by a combination of techniques routinely used.

For example, the oral agents such as tablets, capsules, granules, and powders can be prepared by combining the compound of the present invention, as appropriate, with a diluent (e.g., lactose, mannitol, starch, crystalline cellulose, light anhydrous silicic acid, calcium carbonate, and calcium hydrogen phosphate), a lubricant (e.g., stearic acid, magnesium stearate, and talc), a binder (e.g., starch, hydroxypropylcellulose, hydroxypropylmethylcellulose, and polyvinylpyrrolidone), a disintegrant (e.g., carboxymethylcellulose, low substituted hydroxypropylmethylcellulose, and calcium citrate), a coating agent (e.g., hydroxypropylmethylcellulose, macrogol, and silicone resin), a stabilizer (e.g., ethyl p-oxybenzoate and benzyl alcohol), a corrigent (e.g., sweetening agents, acidulants, and flavors), and the like.

Moreover, the parenteral agents such as injections and ophthalmic solutions can be prepared by combining the compound of the present invention, as appropriate, with, for example, a tonicity agent (e.g., glycerin, propylene glycol, sodium chloride, potassium chloride, sorbitol, and mannitol), a buffering agent (e.g., phosphoric acid, phosphate, citric acid, glacial acetic acid, ε-aminocaproic acid, and Trometamol), a pH adjuster (e.g., hydrochloric acid, citric acid, phosphoric acid, glacial acetic acid, sodium hydroxide, potassium hydroxide, sodium carbonate, and sodium bicarbonate), a solubilizing or dispersing agent (e.g., polysorbate 80, polyoxyethylene hydrogenated castor oil 60, macrogol 4000, purified soybean lecithin, and polyoxyethylene (160) polyoxypropylene (30) glycol), a cellulose polymer (e.g., hydroxypropylmethylcellulose and hydroxypropylcellulose), a thickening agent (e.g., polyvinyl alcohol and polyvinylpyrrolidone), a stabilizer (e.g., edetic acid and sodium edetate), a preservative or antiseptic routinely used (e.g., sorbic acid, potassium sorbate, benzalkonium chloride, benzethonium chloride, methyl p-oxybenzoate, propyl p-oxybenzoate, and chlorobutanol), and a soothing agent (e.g., chlorobutanol, benzyl alcohol, and lidocaine).

In this context, the pH of the injection or ophthalmic solution is preferably set to 4.0 to 8.0, and the osmotic pressure ratio is preferably set to around 1.0.

The dose of the compound of the present invention can be selected appropriately for use according to conditions, age, dosage forms, etc. For example, the oral agent can usually be administered at single or divided doses of 0.01 to 1000 mg, preferably 1 to 100 mg, per day.

Moreover, the ophthalmic solution can usually be administered at single or divided doses at a concentration of 0.0001% to 10% (w/v), preferably 0.01% to 5% (w/v). Intravenous administration is performed at a dose ranging from 0.1 to 100 mg/human, preferably 1 to 30 mg/human, per day. Oral administration is performed at a dose ranging from 1 to 1,000 mg/human, preferably 10 to 30 mg/human, per day. According to circumstances, a dose below this range suffices, or on the contrary, a dose above the range may be required. Moreover, the daily dose can also be divided into two or three portions for administration.

EXAMPLES

Hereinafter, production examples of synthetic intermediates and compounds of the present invention, and subsequently evaluation examples of biological activity will be shown. These examples are provided for well understanding the present invention and are not intended to limit the scope of the present invention. Moreover, Boc in chemical structures represents a tert-butoxycarbonyl group, unless otherwise specified.

Production Examples

Reference Example 1

Synthesis of 6-aminoisoquinoline (Reference Compound 1)

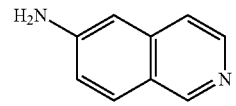 [SMILES: Nc1ccc2cnccc2c1]

6-bromoisoquinoline that weighed 17.2 g (see WO 2008/077553), 200 mL of 28% ammonia water and 10.8 g of copper (II) sulfate pentahydrate were put into the autoclave and tightly sealed, and the mixture was then stirred at 190° C. for 6 hours. After cooling to room temperature, the reaction solution was poured into 250 mL of a 10% aqueous sodium hydroxide solution, followed by extraction with ethyl acetate (100 mL×5). The extract was dried over anhydrous sodium sulfate, filtered, and then concentrated. The obtained crude product was suspended in dichloromethane and then filtered to obtain 10.2 g of the compound of interest as a light brown crystal (85%).

$^1$H-NMR spectrum (CDCl$_3$, δ ppm): 5.54 (br s, 2H), 6.58 (s, 1H), 7.00 (d, J=9.0 Hz, 1H), 7.35 (d, J=5.5 Hz, 1H), 7.75 (d, J=9.0 Hz, 1H), 8.32 (d, J=5.5 Hz, 1H), 8.98 (s, 1H)

Reference Example 2

Synthesis of 6-chlorosulfonylisoquinoline (Reference Compound 2)

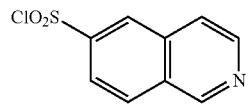 [SMILES: O=S(=O)(Cl)c1ccc2cnccc2c1]

4.0 g of 6-aminoisoquinoline (Reference Compound 1) was suspended at 0° C. in 40 mL of concentrated hydrochloric acid (35%). To the suspension, 4.0 g of sodium nitrite was added in small portions, and the mixture was stirred for 30 minutes. This reaction solution was added dropwise at 0° C. to a mixed solution of 20 mL of acetic acid saturated with sulfite gas generated from sodium bisulfite and sulfuric acid, and 298 mg of copper chloride, and the mixture was stirred for 1 hour. The mixture was neutralized by the addition of a saturated aqueous solution of sodium bicarbonate, followed by extraction with dichloromethane (100 mL×2). The organic layer was washed with saturated saline and then dried over anhydrous sodium sulfate. The obtained dichloromethane solution was used in the next reaction without being further purified because the compound of interest was unstable.

Reference Example 3

Synthesis of 6-chlorosulfonyl-8-fluoroisoquinoline (Reference Compound 3)

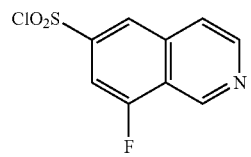 [SMILES: O=S(=O)(Cl)c1cc(F)c2cnccc2c1]

Reference Compound 3 was synthesized using 6-bromo-8-fluoroisoquinoline (synthesized with reference to WO 2008/077553) according to the production methods of Reference Compounds 1 and 2. The obtained dichloromethane solution was used in the next reaction without being further purified.

Reference Example 4

Synthesis of 5-bromo-6-chlorosulfonylisoquinoline (Reference Compound 4)

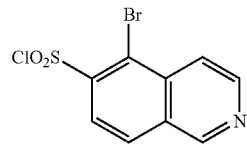 [SMILES: O=S(=O)(Cl)c1ccc2cnccc2c1Br]

Reference Compound 4 was synthesized using 6-amino-5-bromoisoquinoline (see Bioorg. Med. Chem. Lett. 13, 1345 (2003)) according to the production method of Reference Compound 2. The obtained dichloromethane solution was used in the next reaction without being further purified.

Reference Example 5

Synthesis of 6-chlorosulfonyl-7-fluoroisoquinoline (Reference Compound 5)

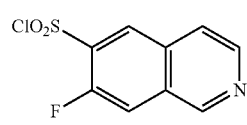 [SMILES: O=S(=O)(Cl)c1cc2ccncc2cc1F]

Reference Compound 5 was synthesized using 6-bromo-7-fluoroisoquinoline (synthesized with reference to WO 2008/077553) according to the production methods of Reference Compounds 1 and 2. The obtained dichloromethane solution was used in the next reaction without being further purified.

Reference Example 6

Synthesis of 6-chlorosulfonyl-5-nitroisoquinoline (Reference Compound 6)

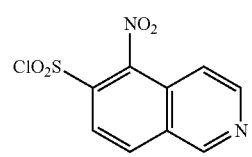 [SMILES: O=[N+]([O-])c1c(S(=O)(=O)Cl)ccc2cnccc12]

Reference Compound 6 was synthesized using 6-bromo-5-nitroisoquinoline (see Bioorg. Med. Chem. Lett. 16, 3150 (2006)) according to the production methods of Reference Compounds 1 and 2. The obtained dichloromethane solution was used in the next reaction without being further purified.

Reference Example 7

Hereinafter, Reference Compounds 7 to 34 were synthesized according to WO2006/115244 and US2008/064681.

(S)-2-amino-1-{tert-butoxycarbonyl(2-tert-butyldimethylsiloxymethyl)amino}propane (Reference Compound 7)

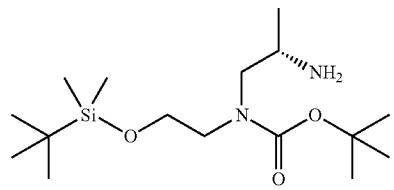 [SMILES: C[C@H](N)CN(CCO[Si](C)(C)C(C)(C)C)C(=O)OC(C)(C)C]

$^1$H-NMR spectrum (CDCl$_3$, δ ppm): 0.04 (s, 6H), 0.89 (s, 9H), 1.17 (d, J=5.5 Hz, 3H), 1.45 (s, 9H), 3.08-3.14 (m, 3H), 3.29 (s, 2H), 3.63-3.68 (m, 2H), 4.23 (br s, 2H)

(2R,2'S)-2-amino-N-(tert-butoxycarbonyl)-N-(2-hydroxypropyl)propylamine (Reference Compound 8)

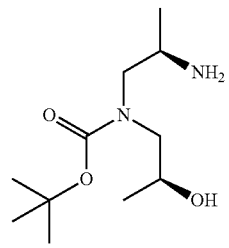 [SMILES: C[C@H](O)CN(C[C@@H](C)N)C(=O)OC(C)(C)C]

¹H-NMR spectrum (CDCl₃, δ ppm): 1.10 (s, 6H), 1.43 (s, 9H), 2.67-2.69 (m, 2H), 3.29 (br s, 3H), 3.41 (br s, 1H), 3.62 (br s, 1H), 4.03 (br s, 2H)

(S)-2-amino-1-{tert-butoxycarbonyl(3-tert-butyldimethylsiloxypropyl)amino}propane (Reference Compound 9)

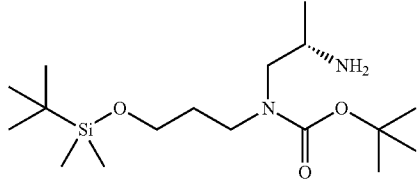 [SMILES: C[C@H](N)CN(CCCO[Si](C)(C)C(C)(C)C)C(=O)OC(C)(C)C]

¹H-NMR spectrum (CDCl₃, δ ppm): 0.04 (s, 6H), 0.89 (s, 9H), 1.06 (m, 3H), 1.45 (s, 9H), 1.74 (br s, 2H), 3.10 (br s, 2H), 3.29 (br s, 2H), 3.61 (m, 3H), 4.56 (br s, 2H)

S)-2-amino-1-(tert-butoxycarbonyl-3-hydroxypropylamino)propane (Reference Compound 10)

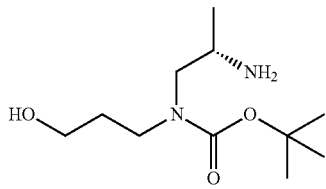 [SMILES: C[C@H](N)CN(CCCO)C(=O)OC(C)(C)C]

¹H-NMR spectrum (CDCl₃, δ ppm): 1.07 (d, J=6.1 Hz, 3H), 1.47 (s, 9H), 1.70 (br s, 2H), 3.00 (br s, 1H), 3.09-3.11 (m, 1H), 3.14-3.19 (m, 1H), 3.44 (br s, 3H), 3.55 (br s, 2H), 3.97 (br s, 2H)

(R)-2-amino-1-{tert-butoxycarbonyl(3-tert-butyldimethylsiloxypropyl)amino}propane (Reference Compound 11)

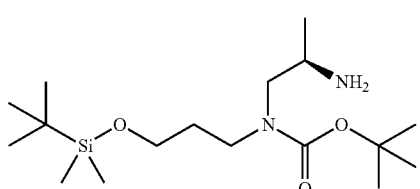

¹H-NMR spectrum (CDCl₃, δ ppm): 0.04 (s, 6H), 0.89 (s, 9H), 1.05 (d, J=5.5 Hz, 3H), 1.45 (s, 9H), 1.75 (s, 2H), 3.08-3.14 (m, 3H), 3.29 (s, 2H), 3.65 (t, J=6.1 Hz, 2H), 5.13 (br s, 2H)

1-{(2-amino-1-methylethyl)-tert-butoxycarbonylamino}-3-tert-butyldimethylsiloxypropane (Reference Compound 12)

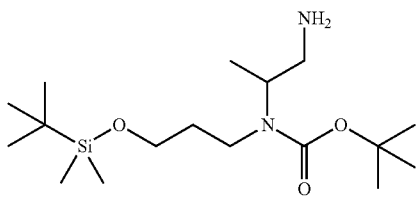 [SMILES: CC(CN)N(CCCO[Si](C)(C)C(C)(C)C)C(=O)OC(C)(C)C]

¹H-NMR spectrum (CDCl₃, δ ppm): 0.05 (s, 6H), 0.89 (s, 9H), 1.12 (d, J=6.1 Hz, 3H), 1.46 (s, 9H), 1.66-1.77 (m, 2H), 2.71 (br s, 2H), 3.10-3.15 (br m, 3H), 3.62 (s, 2H), 3.98 (br s, 2H)

2-amino-4-{tert-butoxycarbonyl(2-tert-butyldimethylsiloxyethyl)amino}butane (Reference Compound 13)

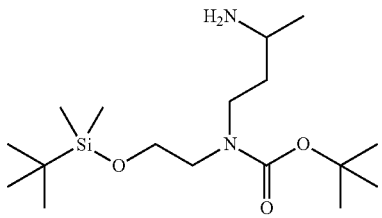 [SMILES: CC(N)CCN(CCO[Si](C)(C)C(C)(C)C)C(=O)OC(C)(C)C]

¹H-NMR spectrum (CDCl₃, δ ppm): 0.07 (s, 6H), 0.84 (s, 9H), 1.17 (d, J=5.5 Hz, 3H), 1.40 (s, 9H), 1.56-1.66 (m, 2H), 2.71-2.91 (br m, 3H), 3.14-3.27 (m, 2H), 3.53-3.67 (m, 2H), 4.89 (br s, 2H)

R)-4-(2-aminoethyl-tert-butoxycarbonylamino)-2-tert-butyldimethylsiloxybutane (Reference Compound 14)

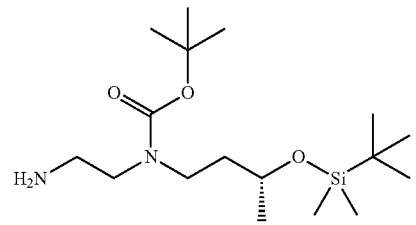 [SMILES: C[C@H](CCN(CCN)C(=O)OC(C)(C)C)O[Si](C)(C)C(C)(C)C]

¹H-NMR spectrum (CDCl₃, δ ppm): 0.05 (s, 6H), 0.89 (s, 9H), 1.15 (d, J=7.7 Hz, 4H), 1.46 (s, 9H), 1.62-1.67 (m, 3H), 2.81 (t, J=6.4 Hz, 2H), 3.23 (br s, 4H), 3.79-3.86 (m, 1H)

S)-4-(2-aminoethyl-tert-butoxycarbonylamino)-2-tert-butyldimethylsiloxybutane (Reference Compound 15)

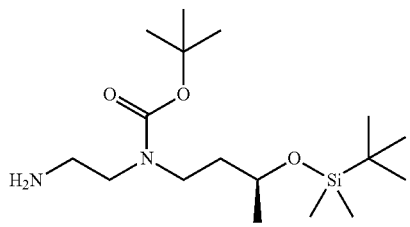 [SMILES: C[C@@H](CCN(CCN)C(=O)OC(C)(C)C)O[Si](C)(C)C(C)(C)C]

¹H-NMR spectrum (CDCl₃, δ ppm): 0.02 (s, 6H), 0.89 (s, 9H), 1.13 (d, J=6.4 Hz, 3H), 1.46 (s, 9H), 1.54-1.65 (m, 4H), 2.81 (t, J=6.2 Hz, 2H), 3.28 (s, 4H), 3.78-3.82 (m, 1H)

3S,2'R)-3-amino-N-(tert-butoxycarbonyl)-N-(2-hydroxypropyl)butylamine (Reference Compound 16)

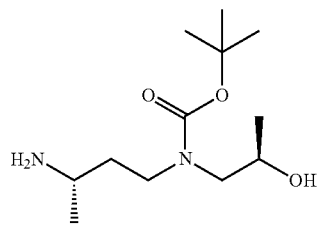 [SMILES: C[C@H](N)CCN(C[C@@H](C)O)C(=O)OC(C)(C)C]

¹H-NMR spectrum (CDCl₃, δ ppm): 1.10 (d, J=6.0 Hz, 3H), 1.14 (d, J=6.0 Hz, 3H), 1.46 (s, 10H), 1.51-1.57 (br s, 2H), 1.65 (br s, 2H), 3.00-3.48 (m, 4H), 3.64 (br s, 1H), 4.03 (br s, 1H)

(3R,2'S)-3-amino-N-(tert-butoxycarbonyl)-N-(2-hydroxypropyl)butylamine (Reference Compound 17)

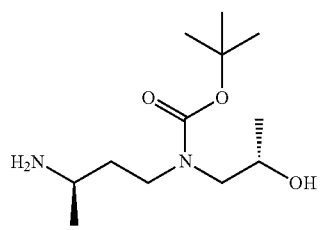 [SMILES: C[C@H](O)CN(CC[C@@H](C)N)C(=O)OC(C)(C)C]

¹H-NMR spectrum (CDCl₃, δ ppm): 1.09 (d, J=5.8 Hz, 3H), 1.14 (d, J=5.8 Hz, 3H), 1.46 (s, 10H), 1.54-1.59 (br s, 2H), 1.72 (br s, 2H), 2.97-3.35 (m, 4H), 3.61 (br s, 1H), 4.33 (br s, 1H)

(2'S,3S)-2-amino-N-(tert-butoxycarbonyl)-N-(3-tert-butyldimethylsiloxybutyl)propylamine (Reference Compound 18)

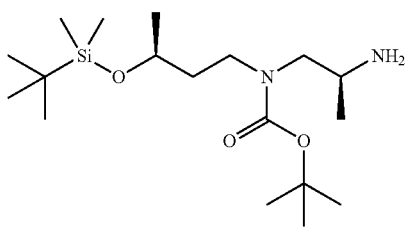 [SMILES: C[C@H](N)CN(CC[C@H](C)O[Si](C)(C)C(C)(C)C)C(=O)OC(C)(C)C]

¹H-NMR spectrum (CDCl₃, δ ppm): 0.01 (s, 6H), 0.84 (s, 9H), 1.02 (d, J=6.0 Hz, 6H), 1.09-1.13 (m, 2H), 1.41 (s, 9H), 1.55-1.60 (m, 2H), 3.02-3.21 (m, 2H), 3.56-3.76 (m, 3H), 3.74-3.78 (m, 1H)

R)-2-amino-1-(tert-butoxycarbonyl-3-hydroxypropylamino)butane (Reference Compound 19)

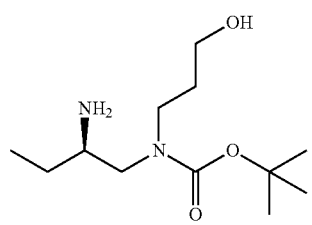 [SMILES: CC[C@@H](N)CN(CCCO)C(=O)OC(C)(C)C]

¹H-NMR spectrum (CDCl₃, δ ppm): 0.96 (t, J=7.8 Hz, 3H), 1.20-1.28 (m, 2H), 1.44 (s, 9H), 1.63-1.67 (m, 2H), 2.90-2.94 (m, 1H), 3.18-3.28 (m, 2H), 3.44-3.66 (m, 5H), 4.66 (br s, 2H)

S)-2-amino-3-fluoro-N-(tert-butoxycarbonyl)-N-(3-hydroxypropyl)propylamine (Reference Compound 20)

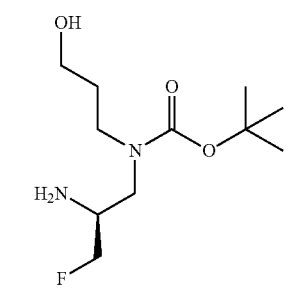 [SMILES: CC(C)(C)OC(=O)N(CCCO)C[C@H](N)CF]

¹H-NMR spectrum (CDCl₃, δ ppm): 1.44 (s, 9H), 1.64-1.75 (m, 5H), 3.12-3.16 (m, 1H), 3.25-3.27 (m, 2H), 3.40-3.44 (m, 2H), 3.56-3.60 (m, 2H), 4.25-4.47 (m, 2H)

1-(2-aminoethyl-tert-butoxycarbonylamino)-4-tert-butyldimethylsiloxybutane (Reference Compound 21)

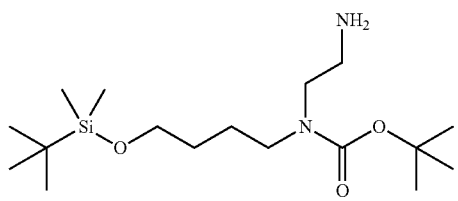 [SMILES: CC(C)(C)OC(=O)N(CCN)CCCCO[Si](C)(C)C(C)(C)C]

¹H-NMR spectrum (CDCl₃, δ ppm): 0.04 (s, 6H), 0.88 (s, 9H), 1.45 (s, 9H), 1.49-1.52 (m, 2H), 1.54-1.60 (m, 2H), 3.08-3.21 (m, 4H), 3.23 (br s, 2H), 3.59-3.72 (m, 4H)

(S)-1-{tert-butoxycarbonyl(2-aminopropyl)amino}-4-tert-butyldimethylsiloxybutane (Reference Compound 22)

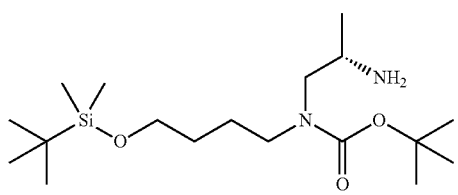 [SMILES: C[C@H](N)CN(CCCCO[Si](C)(C)C(C)(C)C)C(=O)OC(C)(C)C]

¹H-NMR spectrum (CDCl₃, δ ppm): 0.04 (s, 6H), 0.90 (s, 9H), 1.11 (d, J=6.0 Hz, 3H), 1.46 (s, 9H), 1.52 (s, 2H), 1.47-1.74 (m, 2H), 3.07-3.23 (m, 3H), 3.23 (br s, 2H), 3.61 (t, J=6.2 Hz, 2H), 4.02 (br s, 2H)

(R)-1-{tert-butoxycarbonyl(2-aminopropyl)amino}-4-tert-butyldimethylsiloxybutane (Reference Compound 23)

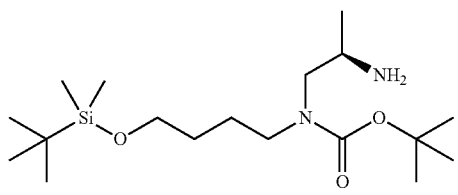 [SMILES: C[C@@H](N)CN(CCCCO[Si](C)(C)C(C)(C)C)C(=O)OC(C)(C)C]

¹H-NMR spectrum (CDCl₃, δ ppm): 0.04 (s, 6H), 0.89 (s, 9H), 1.06 (d, J=6.1 Hz, 3H), 1.45 (s, 9H), 1.49 (s, 2H), 1.54-1.61 (m, 2H), 3.08-3.14 (m, 3H), 3.23 (br s, 2H), 3.61 (t, J=6.1 Hz, 2H), 4.13 (br s, 2H)

R)-4-amino-1-{tert-butoxycarbonyl(2-hydroxyethyl)amino}-2-methylbutane (Reference Compound 24)

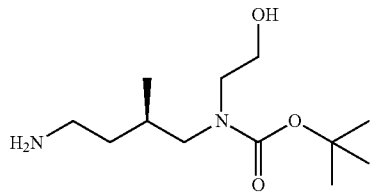 [SMILES: C[C@H](CCN)CN(CCO)C(=O)OC(C)(C)C]

¹H-NMR spectrum (CDCl₃, δ ppm): 0.89 (d, J=6.9 Hz, 3H), 1.24-1.26 (m, 1H), 1.46 (s, 9H), 1.47-1.52 (m, 2H), 1.87 (br s, 3H), 2.68 (dt, J=7.6, 14.2 Hz, 1H), 2.79-2.85 (m, 1H), 2.96-3.01 (m, 1H), 3.30 (br s, 2H), 3.47 (dt, J=5.0, 14.7 Hz, 1H), 3.70-3.79 (m, 2H)

(R)-1-{tert-butoxycarbonyl(2-aminoethyl)amino}-4-hydroxy-3-methylbutane (Reference Compound 25)

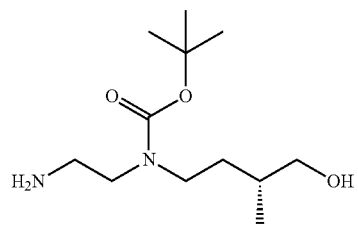 [SMILES: C[C@@H](CO)CCN(CCN)C(=O)OC(C)(C)C]

¹H-NMR spectrum (CDCl₃, δ ppm): 0.95 (d, J=6.7 Hz, 3H), 1.46 (s, 9H), 1.55 (br s, 3H), 1.61-1.71 (m, 3H), 2.84 (t, J=6.8 Hz, 2H), 3.21-3.29 (m, 4H), 3.46-3.52 (m, 2H)

R)-2-amino-1-(tert-butoxycarbonyl-4-hydroxybutylamino)butane (Reference Compound 26)

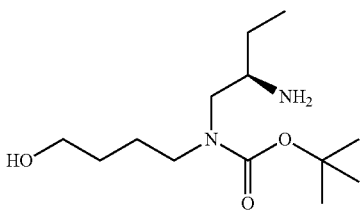 [SMILES: CC[C@@H](N)CN(CCCCO)C(=O)OC(C)(C)C]

¹H-NMR spectrum (CDCl₃, δ ppm): 0.95 (t, J=7.0 Hz, 3H), 1.45 (s, 9H), 1.52-1.63 (m, 6H), 2.86-2.89 (m, 1H), 3.16-3.26 (m, 3H), 3.65-3.67 (m, 4H), 4.56 (br s, 2H)

S)-2-amino-3-fluoro-N-(tert-butoxycarbonyl)-N-(4-hydroxybutyl)propylamine (Reference Compound 27)

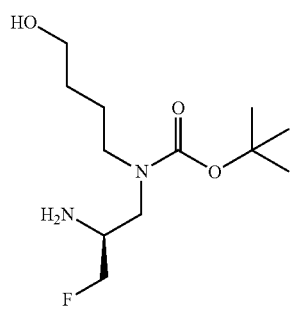 [SMILES: CC(C)(C)OC(=O)N(CCCCO)C[C@H](N)CF]

¹H-NMR spectrum (CDCl₃, δ ppm): 1.44 (s, 9H), 1.54-1.63 (m, 5H), 2.86-2.89 (br s, 2H), 3.20-3.28 (m, 4H), 3.48-3.49 (m, 1H), 3.66-3.68 (m, 2H), 4.27-4.54 (m, 2H)

S)-3-amino-N-(tert-butoxycarbonyl)-N-(3-hydroxypropyl)butylamine (Reference Compound 28)

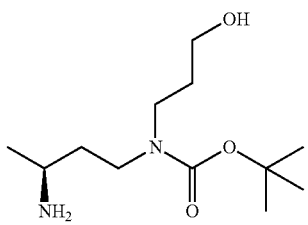 [SMILES: C[C@H](N)CCN(CCCO)C(=O)OC(C)(C)C]

¹H-NMR spectrum (CDCl₃, δ ppm): 1.09 (d, J=6.5 Hz, 3H), 1.47 (s, 9H), 1.62-1.70 (m, 4H), 2.87-2.90 (m, 1H), 3.13-3.19 (m, 1H), 3.25-3.37 (m, 3H), 3.54 (br s, 2H)

Synthesis of (R)-3-amino-N-(tert-butoxycarbonyl)-N-(3-hydroxypropyl)butylamine (Reference Compound 29)

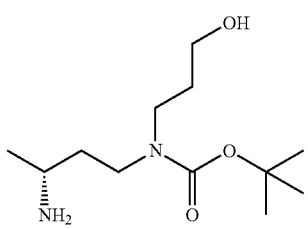 [SMILES: C[C@@H](N)CCN(CCCO)C(=O)OC(C)(C)C]

¹H-NMR spectrum (CDCl₃, δ ppm): 1.09 (d, J=6.5 Hz, 3H), 1.47 (s, 9H), 1.59-1.67 (m, 4H), 2.88-2.91 (m, 1H), 3.13-3.19 (m, 1H), 3.24-3.37 (m, 3H), 3.54 (br s, 2H)

(S)-1-{tert-butoxycarbonyl(2-aminopropyl)amino}-4-hydroxypentane (Reference Compound 30)

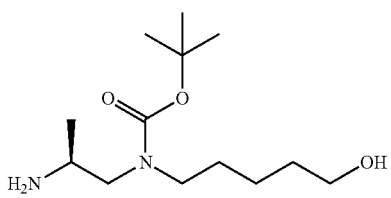 [SMILES: C[C@H](N)CN(CCCCCO)C(=O)OC(C)(C)C]

¹H-NMR spectrum (CDCl₃, δ ppm): 0.94 (d, J=6.9 Hz, 3H), 1.46 (s, 9H), 1.51-1.58 (m, 2H), 1.60-1.64 (m, 2H), 1.73 (br s, 5H), 3.08-3.16 (m, 3H), 3.23-3.28 (m, 2H), 3.66 (t, J=6.3 Hz, 2H)

(R)-1-{tert-butoxycarbonyl(2-aminopropyl)amino}-4-hydroxypentane (Reference Compound 31)

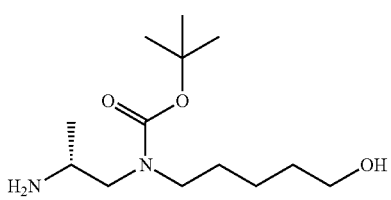 [SMILES: C[C@@H](N)CN(CCCCCO)C(=O)OC(C)(C)C]

¹H-NMR spectrum (CDCl₃, δ ppm): 0.96 (d, J=6.7 Hz, 3H), 1.46 (s, 9H), 1.52-1.58 (m, 2H), 1.61-1.64 (m, 2H), 1.68 (br s, 5H), 3.11-3.20 (m, 3H), 3.29-3.32 (m, 2H), 3.72 (t, J=6.3 Hz, 2H)

R)-2-amino-N-(tert-butoxycarbonyl)-N-(2-hydroxyethoxyethyl)propylamine (Reference Compound 32)

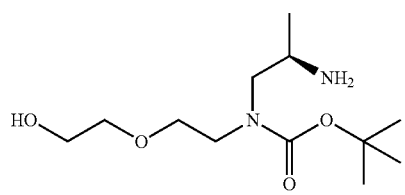 [SMILES: C[C@@H](N)CN(CCOCCO)C(=O)OC(C)(C)C]

¹H-NMR spectrum (CDCl₃, δ ppm): 1.04 (d, J=6.0 Hz, 3H), 1.46 (s, 9H), 1.52-1.56 (br s, 3H), 3.24-3.34 (m, 3H), 3.54-3.75 (m, 8H)

R)-1-amino-N-[2-{(2-tert-butyldimethylsiloxyethyl)-tert-butoxycarbonylamino}ethyl]-N-tert-butoxycarbonylaminopropane (Reference Compound 33)

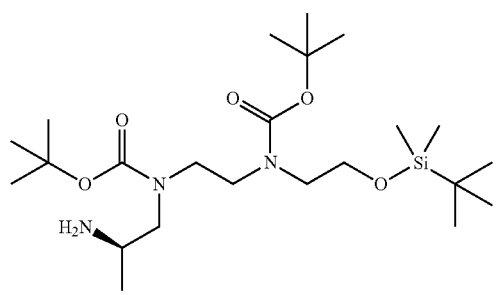 [SMILES: C[C@@H](N)CN(CCN(CCO[Si](C)(C)C(C)(C)C)C(=O)OC(C)(C)C)C(=O)OC(C)(C)C]

¹H-NMR spectrum (CDCl₃, δ ppm): 0.04 (s, 6H), 0.88 (s, 9H), 1.13 (d, J=6.0 Hz, 3H), 1.44 (s, 9H), 1.47 (s, 9H), 3.12-3.52 (m, 11H), 3.64-3.73 (m, 2H)

S)-1-(tert-butoxycarbonyl-3-hydroxypropylamino)-6-tert-butoxycarbonylamino-2-aminohexane (Reference Compound 34)

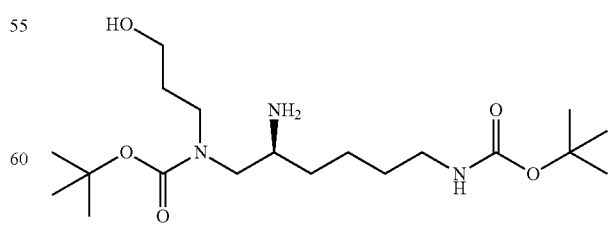

¹H-NMR spectrum (CDCl₃, δ ppm): 1.24-1.33 (m, 2H), 1.38-1.49 (m, 22H), 1.49-1.69 (m, 3H), 2.88-3.13 (m, 6H), 3.44-3.54 (m, 4H), 4.68 (br s, 2H)

Reference Example 8

Synthesis of (R)-4-amino-N-(tert-butoxycarbonyl)-N-(2-hydroxyethyl)pentylamine (Reference Compound 35)

Step 1

Synthesis of N—[(R)-4-(benzyloxy)-1-methyl-but-2-enyl]-trifluoroacetamide

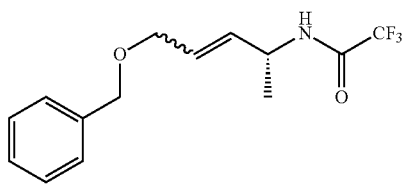 [SMILES: C[C@H](C=CCOCc1ccccc1)NC(=O)C(F)(F)F]

(2R)-(2-trifluoroacetamidopropyl)triphenylphosphonium iodide (8.3 g) synthesized according to J. Med. Chem. 2007, 50, 5627-5643 was dissolved in anhydrous tetrahydrofuran and cooled to −78° C. n-butyllithium (1.6 M n-hexane solution, 18.7 mL) was slowly added dropwise. After the dropwise addition, the mixture was stirred at room temperature for 20 minutes. Subsequently, the mixture was cooled to −78° C., and an anhydrous tetrahydrofuran (10 mL) solution of 2-benzyloxyacetaldehyde (2.35 g) was added. The mixture was gradually returned to room temperature and stirred at room temperature for 12 hours. After the completion of reaction, a saturated aqueous solution of ammonium chloride was added, followed by extraction with ethyl acetate. The organic layer was washed with saturated saline and dried over anhydrous sodium sulfate. After concentration under reduced pressure, the obtained residue was purified by silica gel column chromatography (hexane/ethyl acetate=5/1) to obtain the compound of interest as a pale yellow oil (2.30 g, 52.6%).

$^1$H-NMR spectrum (CDCl$_3$, δ ppm): 1.31 (d, J=6.0 Hz, 1.5H), 1.33 (d, J=6.0 Hz, 1.5H), 4.14-4.16 (m, 2H), 4.52 (s, 2H), 4.58-4.63 (m, 0.5H), 4.77-4.79 (m, 0.5H), 5.46-5.50 (m, 0.5H), 5.75-5.80 (m, 1.5H), 6.17 (br s, 0.5H), 6.43 (br s, 0.5H), 7.30-7.41 (m, 5H)

Step 2

Synthesis of (R)-4-(trifluoroacetylamino)-1-pentanol

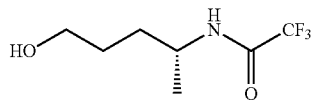

The product (1.0 g) obtained in Step 1 was dissolved in ethyl acetate (10 mL). To the solution, 10% palladium-carbon (300 mg) was added, and the mixture was stirred at 70° C. for 3 hours in a hydrogen atmosphere. After the completion of reaction, the mixture was returned to room temperature, and dichloromethane (5 mL) was added, followed by filtration through celite. The filtrate was concentrated under reduced pressure, and the obtained residue was dissolved in methanol. 10% palladium-carbon (200 mg) was added again thereto, and the mixture was stirred at 70° C. for 16 hours in a hydrogen atmosphere. The mixture was returned to room temperature, and dichloromethane (5 mL) was added, followed by filtration through celite. The filtrate was concentrated under reduced pressure to obtain the compound of interest as a colorless oil (676 mg, 98.3%).

$^1$H-NMR spectrum (CDCl$_3$, δ ppm): 1.24 (d, J=6.0 Hz, 3H), 1.52 (dd, J=5.0 Hz, 1H), 1.59-1.69 (m, 4H), 3.69-3.72 (m, 2H), 4.05-4.08 (m, 1H), 6.59 (br s, 1H)

Step 3

Synthesis of (R)-4-(benzyloxycarbonylamino)-1-pentanol

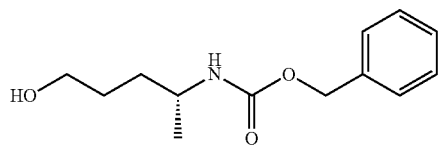 [SMILES: C[C@H](CCCO)NC(=O)OCc1ccccc1]

The product (3.00 g) obtained in Step 2 was dissolved in methanol (200 mL)-water (40 mL). To the solution, potassium carbonate (10 g) was added, and the mixture was stirred at 80° C. for 30 hours. After the completion of reaction, the mixture was returned to room temperature and concentrated under reduced pressure. Methanol was added, and the deposited redundant potassium carbonate was removed by filtration. The filtrate was concentrated under reduced pressure, and the obtained residue was dissolved in dichloromethane (20 mL). After cooling to 0° C., triethylamine (2.10 mL) and benzyl chloroformate (2.55 g) were added, and the mixture was stirred at room temperature for 16 hours. Water was added, followed by extraction with dichloromethane. The organic layer was washed with saturated saline and dried over anhydrous sodium sulfate. After concentration under reduced pressure, the obtained residue was purified by silica gel column chromatography (hexane/ethyl acetate=1/2) to obtain the compound of interest as a white solid (900 mg, 25.2%, 2 steps).

$^1$H-NMR spectrum (CDCl$_3$, δ ppm): 1.15 (d, J=6.5 Hz, 3H), 1.25-1.31 (m, 1H), 1.53-1.60 (m, 4H), 3.66-3.77 (m, 3H), 4.59-4.70 (m, 1H), 5.08 (s, 2H), 7.31-7.36 (m, 5H)

Step 4

Synthesis of (R)-4-amino-N-(tert-butoxycarbonyl)-N-(2-hydroxyethyl)pentylamine (Reference Compound 35)

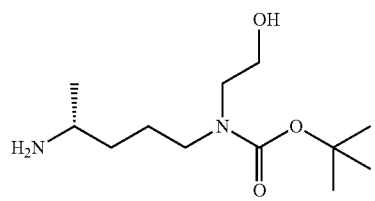 [SMILES: C[C@@H](N)CCCN(CCO)C(=O)OC(C)(C)C]

The compound of interest was synthesized (631 mg, 97.7%) according to WO2006/115244 and US2008/064681 using the compound (1.0 g) obtained in Step 3.

¹H-NMR spectrum (CDCl₃, δ ppm): 1.07 (d, J=6.0 Hz, 3H), 1.27-1.31 (m, 2H), 1.46 (s, 9H), 1.58 (m, 1H), 1.78-1.85 (m, 4H), 2.88-2.91 (m, 1H), 3.20-3.25 (m, 2H), 3.35-3.40 (m, 2H), 3.70-3.75 (m, 2H)

Reference Example 9

Synthesis of (R,Z)-4-tert-butoxycarbonyl-2-methyl-1,2,3,4,5,8-hexahydro-1,4-diazocine (Reference Compound 36)

Step 1

Synthesis of (R)—N-{1-(allylamino)propan-2-yl}-2-nitrobenzenesulfonamide

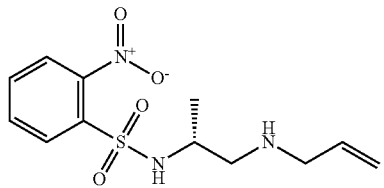 [SMILES: C=CCNC[C@@H](C)NS(=O)(=O)c1ccccc1[N+](=O)[O-]]

5.4 mL of allylamine was added to a tetrahydrofuran (100 mL) solution of 8.2 g of (R)-2-(2-nitrophenylsulfonamido)propyl methanesulfonate, and the mixture was stirred at 80° C. for 16 hours. After the completion of reaction, the reaction solution was returned to room temperature, and 100 mL of saturated saline was added thereto. From this mixed solution, two extractions were performed with 100 mL of ethyl acetate. The extract was dried over anhydrous sodium sulfate. After filtration, the filtrate was concentrated, and the obtained crude product was purified by silica gel column chromatography (ethyl acetate:hexane=1:1) to obtain 7 g of the compound of interest as a yellow oil (96%).

¹H-NMR spectrum (CDCl₃, δ ppm): 1.16 (d, J=6.7 Hz, 3H), 2.60 (ddd, J=26.7, 12.7, 6.0 Hz, 2H), 3.08 (d, J=6.1 Hz, 2H), 3.50-3.52 (m, 1H), 5.03-5.07 (m, 3H), 5.72-5.75 (m, 1H), 6.21 (br s, 1H), 7.73-7.74 (m, 3H), 8.16-8.18 (m, 1H)

Step 2

Synthesis of (R)—N-[1-{allyl(tert-butoxycarbonyl)amino}propan-2-yl]-2-nitrobenzenesulfonamide

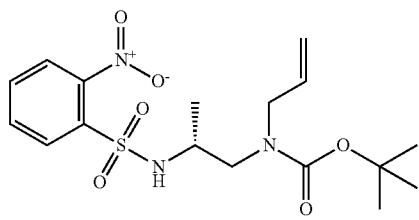 [SMILES: C=CCN(C[C@@H](C)NS(=O)(=O)c1ccccc1[N+](=O)[O-])C(=O)OC(C)(C)C]

A 2N aqueous NaOH solution (50 mL) and 6.1 g of tert-butyl dicarbonate were added to a tetrahydrofuran (100 mL) solution of 7 g of the compound obtained in Step 1, stirring at room temperature and reacted at room temperature for 6 hours. After the completion of reaction, 100 mL of water was added, followed by two extractions with 100 mL of ethyl acetate. The combined organic layer was washed with 100 mL of saturated saline and dried over anhydrous sodium sulfate. After filtration, the filtrate was concentrated, and the obtained crude product was purified by silica gel column chromatography (ethyl acetate:hexane=1:2) to obtain 8 g of the compound of interest as a yellow oil (86%).

¹H-NMR spectrum (CDCl₃, δ ppm): 1.10 (d, J=5.9 Hz, 3H), 1.43 (s, 9H), 3.13 (dd, J=5.0, 14.0 Hz, 1H), 3.24-3.36 (m, 1H), 3.72 (s, 2H), 3.77-3.84 (m, 1H), 5.05-5.11 (m, 2H), 5.68 (br s, 1H), 5.86 (br s, 1H), 7.73 (s, 2H), 7.84 (s, 1H), 8.13 (d, J=6.2 Hz, 1H)

Step 3

Synthesis of (R)—N-allyl-N-[1-{allyl(tert-butoxycarbonyl)amino}propan-2-yl]-2-nitrobenzenesulfonamide

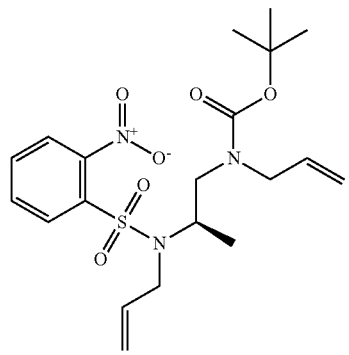 [SMILES: C=CCN(C[C@@H](C)N(CC=C)S(=O)(=O)c1ccccc1[N+](=O)[O-])C(=O)OC(C)(C)C]

0.4 mL of allyl alcohol and 1.5 mL of diisopropyl azodicarboxylate were added dropwise at room temperature in an argon atmosphere to a solution containing 1 g of the compound obtained in Step 2 and 2 g of triphenylphosphine dissolved in 100 mL of tetrahydrofuran, and then reacted for 16 hours. The reaction solution was diluted with water, followed by extraction with ethyl acetate (100 mL×2). Then, the extract was dried over anhydrous sodium sulfate. After filtration, the filtrate was concentrated, and the obtained crude product was purified by silica gel column chromatography (acetone:hexane=1:2) to obtain 550 mg of the compound of interest as a colorless oil (50%).

¹H-NMR spectrum (CDCl₃, δ ppm): 1.18 (d, J=6.3 Hz, 3H), 1.45 (s, 9H), 3.20-3.43 (m, 2H), 3.69-3.83 (m, 2H), 3.99 (s, 2H), 4.25 (q, J=6.4 Hz, 1H), 5.02-5.20 (m, 4H), 5.69-5.78 (m, 2H), 7.62-7.69 (m, 3H), 8.04 (s, 1H)

Step 4

Synthesis of (R,Z)-4-tert-butoxycarbonyl-2-methyl-1-(2-nitrophenylsulfonyl)-1,2,3,4,5,8-hexahydro-1,4-diazocine

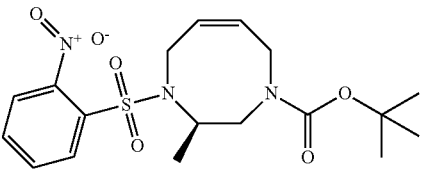

550 mg of the compound obtained in Step 3 and 21 mg of Ru catalyst were dissolved in 30 mL of dichloromethane and heated to reflux with stirring in an argon atmosphere. After 16 hours, the reaction solution was cooled to room temperature and concentrated, and the obtained crude product was purified by silica gel column chromatography (ethyl acetate:hexane=1:2) to obtain 500 mg of the compound of interest as a colorless crystal (97%).

$^1$H-NMR spectrum (CDCl$_3$, δ ppm): 1.07 (d, J=4.6 Hz, 1.5H), 1.09 (d, J=4.6 Hz, 1.5H), 1.47 (s, 9H), 3.47-3.65 (m, 1H), 3.80 (d, J=18.9 Hz, 1H), 4.06-4.28 (m, 5H), 5.71 (s, 2H), 7.66-7.69 (m, 3H), 8.03 (s, 1H)

Step 5

Synthesis of (R,Z)-4-tert-butoxycarbonyl-2-methyl-1,2,3,4,5,8-hexahydro-1,4-diazocine (Reference Compound 36)

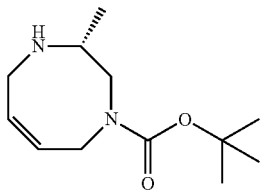 [SMILES: C[C@@H]1CN(C(=O)OC(C)(C)C)C/C=C\CN1]

60 mg of the compound obtained in Step 4 was dissolved in 5 mL of acetonitrile, and 100 mg of potassium carbonate and 0.03 mL of thiophenol were added thereto with stirring at room temperature. After stirring at room temperature for 6 hours, the reaction solution was diluted with water, followed by extraction with dichloromethane (50 mL×2). Then, the extract was dried over anhydrous sodium sulfate. After filtration, the filtrate was concentrated, and the obtained crude product was purified by silica gel column chromatography (methanol:dichloromethane=1:10) to obtain 25 mg of the compound of interest as a colorless oil (76%).

$^1$H-NMR spectrum (CDCl$_3$, δ ppm): 1.04 (d, J=3.1 Hz, 1.5H), 1.06 (d, J=3.1 Hz, 1.5H), 1.46 (s, 9H), 1.78 (br s, 1H), 2.82 (dd, J=9.8, 13.4 Hz, 0.5H), 2.92 (dd, J=9.8, 14.0 Hz, 0.5H), 3.10-3.16 (m, 1H), 3.30 (dd, J=4.9, 15.9 Hz, 1H), 3.53-3.67 (m, 2H), 3.87 (d, J=17.4 Hz, 0.5H), 3.89 (d, J=17.4 Hz, 0.5H), 4.16 (dd, J=4.6, 17.4 Hz, 0.5H), 4.35 (dd, J=3.4, 17.4 Hz, 0.5H), 5.60-5.76 (m, 2H)

Reference Example 10

Synthesis of 2-amino-1-(tert-butoxycarbonyl-3-hydroxypropylamino)-2-methylpropane (Reference Compound 37)

Step 1

Synthesis of benzyl 1-hydroxy-2-methylpropan-2-ylcarbamate

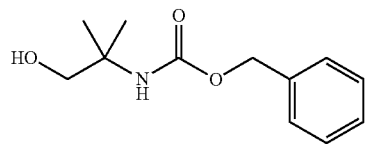 [SMILES: CC(C)(CO)NC(=O)OCc1ccccc1]

3.0 g of 2-amino-2-methylpropan-1-ol was dissolved in 100 mL of dichloromethane, and 100 mL of water and 8.4 g of sodium bicarbonate were then added. To this solution, 5.7 g of benzyl chloroformate was added dropwise, and the mixture was stirred at room temperature for 16 hours. After extraction with dichloromethane (100 mL×3), the extract was dried over anhydrous sodium sulfate. After filtration, the filtrate was concentrated, and the obtained crude product was purified by silica gel column chromatography (ethyl acetate:hexane=1:1) to obtain 7.6 g of the compound of interest as a colorless oil (86%).

$^1$H-NMR spectrum (CDCl$_3$, δ ppm): 1.28 (s, 6H), 1.51 (br s, 1H), 3.60 (d, J=6.0 Hz, 2H), 5.29 (s, 2H), 6.12 (s, 1H), 7.26-7.38 (m, 5H)

Step 2

Synthesis of benzyl 2-methyl-1-oxopropan-2-ylcarbamate

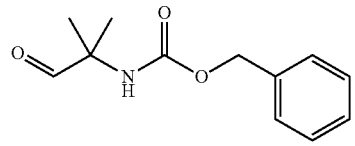 [SMILES: CC(C)(C=O)NC(=O)OCc1ccccc1]

5 mL of oxalyl chloride was dissolved in 30 mL of dichloromethane and then cooled to −78° C. 1.4 mL of dimethyl sulfoxide was added, and the mixture was stirred for 10 minutes. To this reaction solution, a dichloromethane (5 mL) solution of 1.5 g of benzyl-1-hydroxy-2-methylpropan-2-ylcarbamate was added dropwise, and the mixture was stirred for 10 minutes.

To this reaction solution, 3.6 mL of triethylamine was added dropwise, and the mixture was stirred for 10 minutes and then stirred for 1.5 hours with gradual heating to −10° C. After the completion of reaction, water was added to the reaction solution, followed by extraction with dichloromethane (30 mL×2). The extract was dried over anhydrous sodium sulfate. After filtration, the filtrate was concentrated, and the obtained crude product was purified by silica gel column chromatography (ethyl acetate:hexane=1:2) to obtain 960 mg of the compound of interest as a white solid (65%).

$^1$H-NMR spectrum (CDCl$_3$, δ ppm): 1.39 (s, 6H), 5.09 (s, 2H), 6.23 (br s, 1H), 7.28-7.40 (m, 5H), 9.43 (s, 1H)

Step 3

Synthesis of 2-(benzyloxycarbonylamino)-1-(tert-butoxycarbonyl-3-hydroxypropylamino)-2-methylpropane

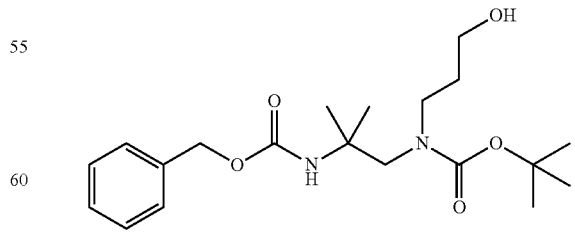

486 mg of 3-aminopropanol and 311 μL of acetic acid were added to a methanol (30 mL) solution of 960 mg of benzyl 2-methyl-1-oxopropan-2-ylcarbamate, and the mixture was then cooled to 0° C. 537 mg of sodium cyanoborohydride was added, and the mixture was stirred at room temperature for 1 hour. After the completion of reaction, water was added to the reaction solution, followed by extraction with ethyl acetate (40 mL×3). The extract was dried over anhydrous sodium sulfate. After filtration, the filtrate was concentrated. To a tetrahydrofuran (30 mL) solution of 1.4 g of the obtained crude product, 7.9 mL of a 10% aqueous sodium hydroxide solution and 20 mL of water were added, then 1.41 g of di-tert-butyl dicarbonate was added, and the mixture was stirred at room temperature for 2 hours. After the completion of reaction, extraction was performed with ethyl acetate (30 mL×3), and the extract was dried over anhydrous sodium sulfate. After filtration, the filtrate was concentrated, and the obtained crude product was purified by silica gel column chromatography (ethyl acetate:hexane=1:1) to obtain 1.1 g of the compound of interest as a colorless oil (67%).

$^1$H-NMR spectrum (CDCl$_3$, δ ppm): 1.33 (s, 6H), 1.46 (s, 9H), 1.60-1.79 (m, 3H), 3.29-3.63 (br m, 6H), 5.04 (s, 2H), 6.31 (br s, 1H), 7.27-7.37 (m, 5H)

Step 4

Synthesis of 2-amino-1-(tert-butoxycarbonyl-3-hydroxypropylamino)-2-methylpropane (Reference Compound 37)

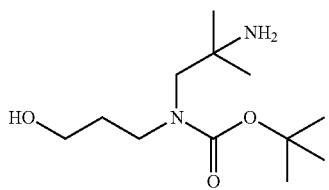 [SMILES: CC(C)(N)CN(CCCO)C(=O)OC(C)(C)C]

0.11 g of palladium-carbon was added to an ethanol (30 mL) solution of 1.1 g of 2-(benzyloxycarbonylamino)-1-(tert-butoxycarbonyl-3-hydroxypropylamino)-2-methylpropane, and the mixture was stirred at room temperature for 2 hours in a hydrogen atmosphere. After the completion of reaction, the reaction solution was concentrated to obtain the compound of interest.

$^1$H-NMR spectrum (CDCl$_3$, δ ppm): 1.15 (s, 6H), 1.47 (s, 9H), 1.75 (br s, 2H), 1.95 (br s, 3H), 3.12 (br s, 2H), 3.53 (br s, 4H)

Example 1

Synthesis of 6-(piperazin-1-ylsulfonyl)isoquinoline dihydrochloride (Compound 1)

Step 1

Synthesis of 6-(4-tert-butoxycarbonylpiperazin-1-ylsulfonyl)isoquinoline

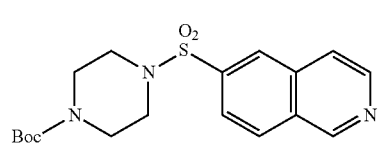 [SMILES: CC(C)(C)OC(=O)N1CCN(S(=O)(=O)c2ccc3cnccc3c2)CC1]

0.5 mL of triethylamine and 0.5 g of tert-butoxycarbonylpiperazine were added with stirring at room temperature to a dichloromethane solution (100 mL) of 6-chlorosulfonylisoquinoline (Reference Compound 2) synthesized according to Reference Example 2 from 500 mg of 6-aminoisoquinoline (Reference Compound 1), and reacted for 6 hours. After the completion of reaction, the reaction solution was washed with saturated saline and dried over anhydrous sodium sulfate. After concentration, the obtained crude product was purified by silica gel column chromatography (ethyl acetate:hexane=1:1) to obtain 150 mg of the compound of interest as a white crystal (23%).

$^1$H-NMR spectrum (CDCl$_3$, δ ppm): 2.42 (s, 9H), 3.11 (d, J=4.9 Hz, 4H), 3.40 (s, 4H), 7.56 (d, J=9.2 Hz, 1H), 7.58 (d, J=5.5 Hz, 1H), 7.83 (s, 1H), 7.93 (d, J=8.5 Hz, 1H), 8.55 (d, J=5.5 Hz, 1H), 9.24 (s, 1H)

Step 2

Synthesis of 6-(piperazin-1-ylsulfonyl)isoquinoline dihydrochloride

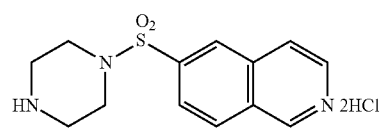

150 mg of 6-(4-tert-butoxycarbonylpiperazin-1-ylsulfonyl)isoquinoline was dissolved in 10 mL of dichloromethane, and 1 mL of 4 M hydrochloric acid-dioxane solution was added dropwise thereto with stirring and then reacted at room temperature for 3 hours. From the reaction solution, the solvent was distilled off, and the obtained residue was dissolved in 0.5 mL of methanol. Then, 5 mL of ethyl acetate was added with vigorous stirring, and the deposited white crystal was collected by filtration and dried to obtain 35 mg of the compound of interest as a white crystal (25%).

$^1$H-NMR spectrum (DMSO-d$_6$, δ ppm): 2.98 (d, J=4.3 Hz, 4H), 3.39 (s, 4H), 4.33 (br s, 1H), 7.99 (d, J=7.9 Hz, 1H), 8.19 (s, 1H), 8.47 (d, J=8.5 Hz, 1H), 8.50 (br s, 2H), 8.59 (s, 1H), 8.72 (dd, J=5.5, 11.0 Hz, 1H), 9.58 (s, 1H)

mp: 242° C.

Example 2

Synthesis of (R)-6-(3-aminopyrrolidin-1-ylsulfonyl)isoquinoline dihydrochloride (Compound 2)

Step 1

Synthesis of (R)-6-(3-tert-butoxycarbonylaminopyrrolidin-1-ylsulfonyl)isoquinoline

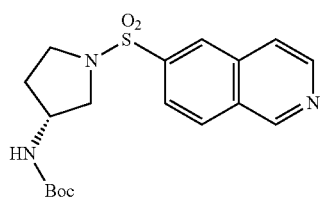 [SMILES: CC(C)(C)OC(=O)N[C@@H]1CCN(S(=O)(=O)c2ccc3cnccc3c2)C1]

The compound of interest was produced (82%) using (3R)-3-(tert-butoxycarbonylamino)pyrrolidine instead of tert-butoxycarbonylpiperazine in Step 1 of Example 1.

$^1$H-NMR spectrum (CDCl$_3$, δ ppm): 1.37 (s, 9H), 1.77-1.80 (m, 1H), 2.05-2.09 (m, 1H), 3.29 (s, 2H), 3.45-3.52 (m, 2H), 4.09-4.14 (m, 1H), 4.48 (s, 1H), 7.81 (d, J=5.5 Hz, 1H), 7.96 (dd, J=1.8, 8.5 Hz, 1H), 8.16 (d, J=9.2 Hz, 1H), 8.38 (s, 1H), 8.71 (d, J=5.5 Hz, 1H), 9.39 (s, 1H)

Step 2

Synthesis of (R)-6-(3-aminopyrrolidin-1-ylsulfonyl)isoquinoline dihydrochloride (Compound 2)

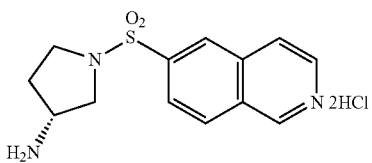

Compound 2 was obtained (67%) using (R)-6-(3-tert-butoxycarbonylaminopyrrolidin-1-ylsulfonyl)isoquinoline instead of 6-(4-tert-butoxycarbonylpiperazin-1-ylsulfonyl)isoquinoline in Step 2 of Example 1.

$^1$H-NMR spectrum (DMSO-d$_6$, δ ppm): 1.83-1.85 (m, 1H), 2.03-2.06 (m, 1H), 3.25-3.28 (m, 1H), 3.31 (dd, J=10.7, 4.0 Hz, 1H), 3.44 (dd, J=7.0, 10.7 Hz, 1H), 3.50 (dd, J=7.9, 16.5 Hz, 1H), 3.70 (s, 1H), 4.36 (br s, 2H), 8.11 (d, J=5.5 Hz, 1H), 8.38 (d, J=5.5 Hz, 1H), 8.54 (d, J=8.5 Hz, 1H), 8.59 (br s, 1H), 8.63 (br s, 1H), 8.69 (s, 1H), 8.75 (d, J=6.1 Hz, 1H), 9.73 (s, 1H)

mp: 281° C.

Example 3

Synthesis of 6-(1,4-diazepan-1-ylsulfonyl)isoquinoline dihydrochloride (Compound 3)

Step 1

Synthesis of 6-(4-tert-butoxycarbonyl-1,4-diazepan-1-ylsulfonyl)isoquinoline

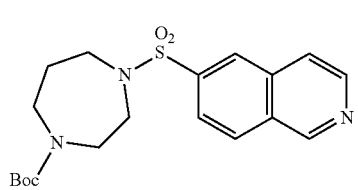 [SMILES: CC(C)(C)OC(=O)N1CCCN(S(=O)(=O)c2ccc3cnccc3c2)CC1]

The compound of interest was produced (54%) using 1-tert-butoxycarbonylhexahydro-1,4-diazepane instead of tert-butoxycarbonylpiperazine in Step 1 of Example 1.

$^1$H-NMR spectrum (CDCl$_3$, δ ppm): 1.41 (s, 9H), 1.96-1.97 (m, 2H), 3.31-3.32 (m, 2H), 3.35-3.42 (m, 2H), 3.47-3.58 (m, 4H), 7.78 (d, J=5.5 Hz, 1H), 7.89 (d, J=8.5 HZ, 1H), 8.12 (d, J=8.5 Hz, 1H), 8.34 (s, 1H), 8.68 (d, J=5.5 Hz, 1H), 9.36 (s, 1H)

Step 2

Synthesis of 6-(1,4-diazepan-1-ylsulfonyl)isoquinoline dihydrochloride (Compound 3)

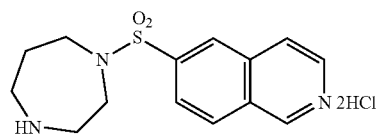

Compound 3 was obtained (42%) using 6-(4-tert-butoxycarbonyl-1,4-diazepan-1-ylsulfonyl)isoquinoline instead of 6-(4-tert-butoxycarbonylpiperazin-1-ylsulfonyl)isoquinoline in Step 2 of Example 1.

$^1$H-NMR spectrum (D$_2$O, δ ppm): 1.99-2.03 (m, 2H), 3.27 (t, J=5.5 Hz, 2H), 3.30 (t, J=5.2 Hz, 2H), 3.41 (t, J=6.1 Hz, 2H), 3.60 (t, J=5.5 Hz, 2H), 8.14-8.15 (m, 1H), 8.41-8.46 (m, 1H), 8.53 (d, J=6.7 Hz, 2H), 8.66 (s, 1H), 9.65 (dd, J=5.2, 8.2 Hz, 1H.

mp: 204° C.

Example 4

Synthesis of 6-(4-aminopiperidin-1-ylsulfonyl)isoquinoline dihydrochloride (Compound 4)

Step 1

Synthesis of 6-{4-(tert-butoxycarbonylamino)piperidin-1-ylsulfonyl}isoquinoline

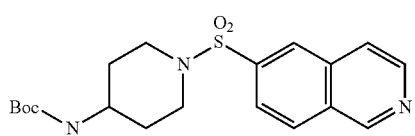

The compound of interest was produced (48%) using 4-(tert-butoxycarbonylamino)piperidine instead of tert-butoxycarbonylpiperazine in Step 1 of Example 1.

$^1$H-NMR spectrum (CDCl$_3$, δ ppm): 1.40 (s, 9H), 1.48-1.53 (m, 2H), 2.00 (d, J=12.2 Hz, 2H), 2.56 (t, J=11.6 Hz, 2H), 3.40 (s, 1H), 3.80 (d, J=10.4 Hz, 2H), 4.39 (s, 1H), 7.80 (d, J=5.5 Hz, 1H), 7.88 (d, J=8.5 Hz, 1H), 8.15 (d, J=9.2 Hz, 1H), 8.32 (s, 1H), 8.71 (d, J=5.5 Hz, 1H), 9.40 (s, 1H)

Step 2

Synthesis of 6-(4-aminopiperidin-1-ylsulfonyl)isoquinoline dihydrochloride (Compound 4)

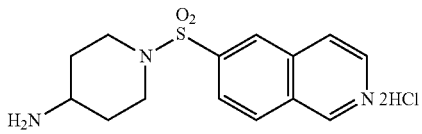

Compound 4 was obtained (31%) using 6-{4-(tert-butoxycarbonylamino)piperidin-1-ylsulfonyl}isoquinoline instead of 6-(4-tert-butoxycarbonylpiperazin-1-ylsulfonyl)isoquinoline in Step 2 of Example 1.

$^1$H-NMR spectrum (DMSO-$d_6$, δ ppm): 1.54 (dd, J=3.8, 11.7 Hz, 2H), 1.94 (d, J=10.4 Hz, 2H), 2.49-2.52 (m, 2H), 3.01-3.03 (m, 1H), 3.74 (d, J=12.8 Hz, 2H), 5.13 (bs s, 2H), 8.01 (dd, J=1.2, 8.5 Hz, 1H), 8.02 (br s, 2H), 8.28 (d, J=5.5 Hz, 1H), 8.49 (d, J=9.2 Hz, 1H), 8.59 (s, 1H), 8.73 (d, J=6.1 Hz, 1H), 9.66 (s, 1H)

mp: 290° C.

Example 5

Synthesis of 5-bromo-6-(1,4-diazepan-1-ylsulfonyl)isoquinoline dihydrochloride (Compound 5)

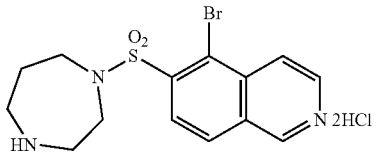

Compound 5 was obtained according to Example 1 using Reference Compound 4 and 1-tert-butoxycarbonylhexahydro-1,4-diazepane.

$^1$H-NMR spectrum (DMSO-$d_6$, δ ppm): 2.05 (t, J=4.9 Hz, 2H), 3.19-3.25 (m, 4H), 3.50 (t, J=6.1 Hz, 2H), 3.76 (t, J=4.6 Hz, 2H), 4.96 (br s, 1H), 8.12 (br s, 2H), 8.20 (d, J=8.5 Hz, 1H), 8.27 (d, J=6.1 Hz, 1H), 8.40 (d, J=8.5 Hz, 1H), 8.81 (d, J=6.1 Hz, 1H), 9.61 (s, 1H)

mp: 215° C.

Example 6

Synthesis of 6-(1,4-diazepan-1-ylsulfonyl)-8-fluoroisoquinoline dihydrochloride (Compound 6)

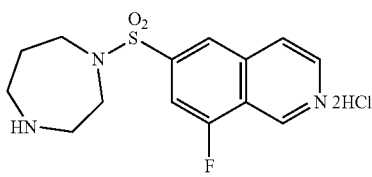

Compound 6 was obtained according to Example 1 using Reference Compound 3 and 1-tert-butoxycarbonylhexahydro-1,4-diazepane.

$^1$H-NMR spectrum (DMSO-$d_6$, δ ppm): 1.96-2.00 (m, 2H), 3.15 (s, 2H), 3.20 (s, 2H), 3.41 (t, J=5.8 Hz, 2H), 3.62 (t, J=4.9 Hz, 2H), 4.52 (br s, 1H), 7.88 (dd, J=1.2, 9.8 Hz, 1H), 8.22 (d, J=5.5 Hz, 1H), 8.27 (br s, 2H), 8.45 (s, 1H), 8.82 (d, J=5.5 Hz, 1H), 9.62 (s, 1H)

mp: 208° C.

Example 7

Synthesis of 6-{(1S,4S)-2,5-diazabicyclo[2.2.1]heptan-2-ylsulfonyl}isoquinoline dihydrochloride (Compound 7)

Step 1

Synthesis of 6-{(1S,4S)-4-tert-butoxycarbonyl-2,5-diazabicyclo[2.2.1]heptan-2-ylsulfonyl}isoquinoline

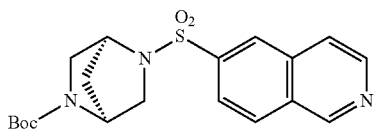 [SMILES: CC(C)(C)OC(=O)N1C[C@@H]2C[C@H]1CN2S(=O)(=O)c1ccc2cnccc2c1]

The compound of interest was produced (85%) using (1S,4S)-4-tert-butoxycarbonyl-2,5-diazabicyclo[2.2.1]heptane instead of tert-butoxycarbonylpiperazine in Step 1 of Example 1.

$^1$H-NMR spectrum (CDCl$_3$, δ ppm): 1.39-1.43 (m, 1H), 1.58 (s, 9H), 1.74 (m, 1H), 3.26-3.33 (m, 2H), 3.43-3.52 (m, 2H), 4.36 (s, 0.5H), 4.47 (s, 0.5H), 4.56 (s, 1H), 7.80 (s, 1H), 7.98 (d, J=7.9 Hz, 1H), 8.15 (d, J=8.5 Hz, 1H), 8.39 (s, 1H), 8.71 (br s, 1H), 9.40 (br s, 1H)

Step 2

Synthesis of 6-{(1S,4S)-2,5-diazabicyclo[2.2.1]heptan-2-ylsulfonyl}isoquinoline dihydrochloride (Compound 7)

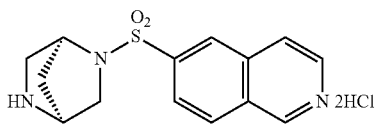

Compound 7 was obtained (95%) using 6-{(1S,4S)-4-tert-butoxycarbonyl-2,5-diazabicyclo[2.2.1]heptan-2-ylsulfonyl}isoquinoline instead of 6-(4-tert-butoxycarbonylpiperazin-1-ylsulfonyl)isoquinoline in Step 2 of Example 1.

$^1$H-NMR spectrum (D$_2$O, δ ppm): 1.38 (d, J=11.6 Hz, 1H), 1.75 (d, J=11.6 Hz, 1H), 3.28 (dd, J=2.4, 11.6 Hz, 2H), 3.43 (td, J=2.2, 10.8 Hz, 2H), 3.61 (d, J=11.0 Hz, 1H), 4.34 (s, 1H), 8.21-8.23 (m, 1H), 8.44 (t, J=5.5 Hz, 1H), 8.57 (d, J=7.3 Hz, 2H), 8.72 (s, 1H), 9.67 (s, 1H)

mp: 192° C.

Example 8

Synthesis of (R,Z)-6-(2-methyl-2,3,4,5-tetrahydro-1,4-diazocin-1(8H)-ylsulfonyl)isoquinoline dihydrochloride (Compound 8)

Step 1

Synthesis of (R,Z)-6-(4-tert-butoxycarbonyl-2-methyl-2,3,4,5-tetrahydro-1,4-diazocin-1(8H)-ylsulfonyl)isoquinoline

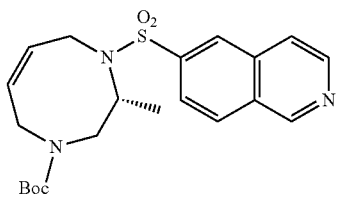 [SMILES: C[C@@H]1CN(C(=O)OC(C)(C)C)C/C=C\CN1S(=O)(=O)c1ccc2cnccc2c1]

The compound of interest was produced (colorless oil, 68%) using Reference Compound 36 instead of tert-butoxycarbonylpiperazine in Step 1 of Example 1.

$^1$H-NMR spectrum (CDCl$_3$, δ ppm): 0.98 (d, J=5.2 Hz, 1.5H), 1.00 (d, J=5.2 Hz, 1.5 Hz), 1.47 (s, 9H), 3.59 (m, 3H), 3.71 (d, J=17.1 Hz, 1H), 4.07-4.14 (m, 1H), 4.22-4.29 (m, 2H), 5.61-5.70 (m, 1H), 5.76-5.81 (m, 1H), 7.78 (d, J=5.5 Hz, 1H), 7.90 (dd, J=1.8, 8.5 Hz, 1H), 8.11 (d, J=8.5 Hz, 1H), 8.37 (s, 1H), 8.68 (d, J=6.1 Hz, 1H), 9.36 (s, 1H)

Step 2

Synthesis of (R,Z)-6-(2-methyl-2,3,4,5-tetrahydro-1,4-diazocin-1(8H)-ylsulfonyl)isoquinoline

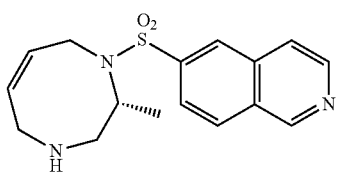 [SMILES: C[C@@H]1CNC/C=C\CN1S(=O)(=O)c1ccc2cnccc2c1]

100 mg of the compound obtained in Step 1 was dissolved in 10 mL of dichloromethane, and 1 mL of trifluoroacetic acid was added dropwise thereto at room temperature and then reacted for 6 hours. The reaction solution was neutralized with a saturated aqueous solution of sodium bicarbonate, followed by extraction with dichloromethane (50 mL×2). The extract was dried over anhydrous sodium sulfate. After filtration, the filtrate was concentrated, and the obtained crude product was purified by silica gel column chromatography (dichloromethane:methanol=10:1) to obtain 40 mg of the compound of interest as a pale yellow oil (53%).

$^1$H-NMR spectrum (CDCl$_3$, δ ppm): 0.96 (d, J=6.1 Hz, 3H), 2.59 (br s, 1H), 2.73 (dd, J=2.4, 14.6 Hz, 1H), 3.04 (dd, J=6.1, 14.6 Hz, 1H), 3.52 (dd, J=4.3, 16.5 Hz, 1H), 3.78 (dd, J=5.2, 16.2 Hz, 1H), 4.08-4.14 (m, 2H), 4.27 (dd, J=5.5, 16.5 Hz, 1H), 5.53-5.57 (m, 1H), 5.83-5.88 (m, 1H), 7.78 (d, J=5.5 Hz, 1H), 7.95 (dd, J=1.2, 8.5 Hz, 1H), 8.10 (d, J=8.5 Hz, 1H), 8.40 (s, 1H), 8.67 (d, J=6.1 Hz, 1H), 9.35 (s, 1H)

Step 3

Synthesis of (R,Z)-6-(2-methyl-2,3,4,5-tetrahydro-1,4-diazocin-1(8H)-ylsulfonyl)isoquinoline dihydrochloride (Compound 8)

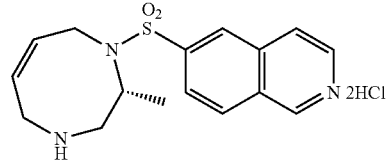

The compound of interest was obtained as a white crystal (81%) using (R,Z)-6-(2-methyl-2,3,4,5-tetrahydro-1,4-diazocin-1(8H)-ylsulfonyl)isoquinoline instead of 6-(4-tert-butoxycarbonylpiperazin-1-ylsulfonyl)isoquinoline in Step 2 of Example 1.

$^1$H-NMR spectrum (D$_2$O, δ ppm): 0.71 (d, J=6.7 Hz, 3H), 3.11 (dd, J=3.1, 14.6 Hz, 1H), 3.21 (t, J=13.4 Hz, 1H), 3.57 (dd, J=8.9, 13.7 Hz, 1H), 3.84 (d, J=20.1 Hz, 1H), 4.53 (m, 3H), 5.61 (d, J=11.0 Hz, 1H), 6.07 (d, J=11.0 Hz, 1H), 8.20 (t, J=6.7 Hz, 1H), 8.38-8.44 (m, 1H), 8.54 (dd, J=6.7, 14.6 Hz, 2H), 8.71 (s, 1H), 9.63 (d, J=7.3 Hz, 1H)

$[α]^{25}_D$ −59.0 (c=0.031, H$_2$O)

Example 9

Synthesis of 6-(morpholin-1-ylsulfonyl)isoquinoline hydrochloride (Compound 9)

Step 1

Synthesis of 6-(morpholin-1-ylsulfonyl)isoquinoline

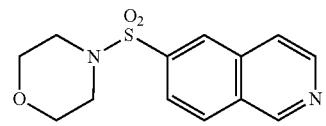 [SMILES: O=S(=O)(c1ccc2cnccc2c1)N1CCOCC1]

The compound of interest was produced (57%) using morpholine instead of tert-butoxycarbonylpiperazine in Step 1 of Example 1.

$^1$H-NMR spectrum (CDCl$_3$, δ ppm): 3.10 (t, J=4.6 Hz, 4H), 3.76 (t, J=4.6 Hz, 4H), 7.81 (d, J=5.5 Hz, 1H), 7.89 (dd, J=1.2, 8.5 Hz, 1H), 8.17 (d, J=8.5 Hz, 1H), 8.33 (s, 1H), 8.71 (d, J=5.5 Hz, 1H), 9.41 (s, 1H)

Step 2

Synthesis of 6-(morpholin-1-ylsulfonyl)isoquinoline hydrochloride (Compound 9)

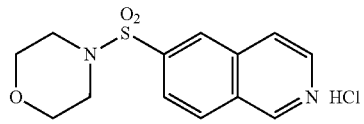 [SMILES: O=S(=O)(c1ccc2cnccc2c1)N1CCOCC1 ; Cl]

Compound 9 was obtained (79%) using 6-(morpholin-1-ylsulfonyl)isoquinoline instead of 6-(4-tert-butoxycarbonylpiperazin-1-ylsulfonyl)isoquinoline in Step 2 of Example 1.

$^1$H-NMR spectrum (D$_2$O, δ ppm): 3.08 (t, J=4.6 Hz, 4H), 3.66 (t, J=4.6 Hz, 4H), 8.14 (d, J=8.5 Hz, 1H), 8.47 (d, J=6.7 Hz, 1H), 8.57 (t, J=7.0 Hz, 2H), 8.64 (s, 1H), 9.69 (s, 1H)
mp: 202° C.

Example 10

Synthesis of (S)-6-{3-(N-methylamino)pyrrolidin-1-ylsulfonyl}isoquinoline dihydrochloride (Compound 10)

Step 1

Synthesis of (S)-6-{3-(tert-butoxycarbonylamino)pyrrolidin-1-ylsulfonyl}isoquinoline

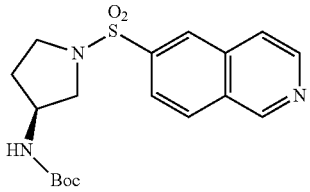 [SMILES: CC(C)(C)OC(=O)N[C@H]1CCN(S(=O)(=O)c2ccc3cnccc3c2)C1]

A dichloromethane solution (100 mL) of 6-chlorosulfonyl-isoquinoline (Reference Compound 2) was added with stirring at room temperature to a solution containing 423 mg of (S)-(−)-3-(tert-butoxycarbonylamino)pyrrolidine dissolved in 20 mL of dichloromethane further supplemented with 0.5 mL of triethylamine, and reacted for 6 hour. The reaction solution was washed with saturated saline and dried over anhydrous sodium sulfate. After filtration, the filtrate was concentrated, and the obtained crude product was purified by silica gel column chromatography (acetone:hexane=1:2) to obtain 560 mg of the compound of interest as a colorless oil (65%).

$^1$H-NMR spectrum (CDCl$_3$, δ ppm): 1.37 (s, 9H), 1.79 (br s, 1H), 2.06-2.09 (m, 1H), 3.26-3.33 (m, 2H), 3.44-3.52 (m, 2H), 4.10 (s, 1H), 4.49 (s, 1H), 7.82 (d, J=4.3 Hz, 1H), 7.96 (dd, J=1.2, 8.5 Hz, 1H), 8.16 (d, J=8.5 Hz, 1H), 8.38 (s, 1H), 8.72 (s, 1H), 9.41 (s, 1H)

Step 2

Synthesis of (S)-6-{3-(N-tert-butoxycarbonyl-N-methylamino)pyrrolidin-1-ylsulfonyl}isoquinoline

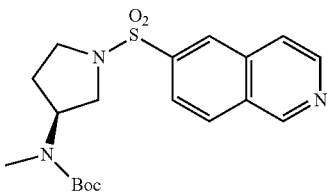 [SMILES: CN(C(=O)OC(C)(C)C)[C@H]1CCN(S(=O)(=O)c2ccc3cnccc3c2)C1]

265 mg of sodium hydride was added with stirring under ice cooling to an N,N-dimethylformamide (10 mL) solution of 500 mg of (S)-6-{3-(tert-butoxycarbonylamino)pyrrolidin-1-ylsulfonyl}isoquinoline obtained in Step 1. After stirring in this state for 30 minutes, 0.8 mL of methyl iodide was added dropwise to the reaction solution, and the mixture was further stirred for 30 minutes for reaction. The reaction was terminated by the dropwise addition of water in small portions under ice cooling to the reaction solution. Then, 50 mL of water was added thereto, followed by three extractions with 50 mL of ether. The combined organic layer was washed with 100 mL of saturated saline and dried over anhydrous sodium sulfate. After filtration, the filtrate was concentrated, and the obtained crude product was purified by silica gel column chromatography (acetone:hexane=1:1) to obtain 100 mg of the compound of interest as a colorless oil (19%).

$^1$H-NMR spectrum (CDCl$_3$, δ ppm): 1.13 (s, 9H), 1.89-1.97 (m, 1H), 1.98-2.04 (m, 1H), 2.71 (s, 3H), 3.15 (s, 1H), 3.23 (t, J=7.9 Hz, 1H), 3.40 (t, J=8.5 Hz, 1H), 3.60 (s, 1H), 4.62 (br s, 1H), 7.81 (d, J=6.1 Hz, 1H), 7.96 (dd, J=1.2, 8.5 Hz, 1H), 8.16 (d, J=8.5 Hz, 1H), 8.38 (s, 1H), 8.70 (d, J=5.5 Hz, 1H), 9.39 (s, 1H)

Step 3

Synthesis of (S)-6-{3-(N-methylamino)pyrrolidin-1-ylsulfonyl}isoquinoline

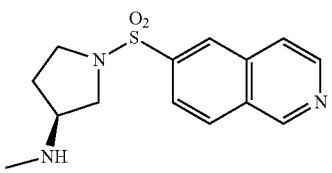 [SMILES: CN[C@H]1CCN(S(=O)(=O)c2ccc3cnccc3c2)C1]

The compound of interest was obtained (pale yellow oil, 54%) according to the method of Step 2 of Example 8 using (S)-6-{3-(N-tert-butoxycarbonyl-N-methylamino)pyrrolidin-1-ylsulfonyl}isoquinoline.

$^1$H-NMR spectrum (CDCl$_3$, δ ppm): 1.57 (br s, 1H), 1.62-1.69 (m, 1H), 1.98-2.05 (m, 1H), 2.30 (s, 3H), 3.13 (dd, J=4.6, 10.1 Hz, 1H), 3.16-3.20 (m, 1H), 3.35-3.40 (m, 1H), 3.42-3.46 (m, 1H), 3.48-3.52 (m, 1H), 7.80 (d, J=5.5 Hz, 1H), 7.98 (dd, J=1.2, 8.5 Hz, 1H), 8.14 (d, J=8.5 Hz, 1H), 8.39 (s, 1H), 8.68 (d, J=6.1 Hz, 1H), 9.37 (s, 1H)

Step 4

Synthesis of (S)-6-{3-(N-methylamino)pyrrolidin-1-ylsulfonyl}isoquinoline dihydrochloride (Compound 10)

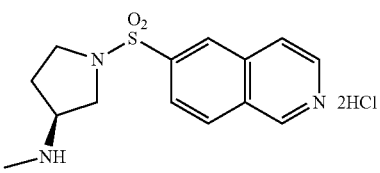 [SMILES: CN[C@H]1CCN(S(=O)(=O)c2ccc3cnccc3c2)C1]

Compound 10 was obtained (white crystal, 90%) using (S)-6-{3-(N-methylamino)pyrrolidin-1-ylsulfonyl}isoquinoline instead of 6-(4-tert-butoxycarbonylpiperazin-1-ylsulfonyl)isoquinoline in Step 2 of Example 1.

$^1$H-NMR spectrum (D$_2$O, δ ppm): 1.97-2.03 (m, 1H), 2.13-2.21 (m, 1H), 2.60 (s, 3H), 3.18-3.24 (m, 1H), 3.44 (dd, J=6.4, 11.3 Hz, 1H), 3.54-3.59 (m, 2H), 3.68-3.72 (m, 1H), 8.19 (dd, J=2.1, 8.9 Hz, 1H), 8.45 (dd, J=3.4, 6.4 Hz, 1H), 8.56 (d, J=6.7 Hz, 2H), 8.69 (s, 1H), 9.67 (s, 1H)
mp: 189° C.
$[α]^{25}{}_D$ +30.3 (c=0.038, H$_2$O)

Example 11

Synthesis of (S)-6-{3-(N-butylamino)pyrrolidin-1-ylsulfonyl}isoquinoline dihydrochloride (Compound 11)

Step 1

Synthesis of (S)-6-{3-(N-tert-butoxycarbonyl-N-butylamino)pyrrolidin-1-ylsulfonyl}isoquinoline

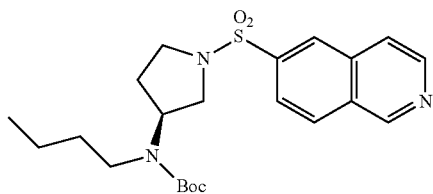 [SMILES: CCCCN(C(=O)OC(C)(C)C)[C@H]1CCN(S(=O)(=O)c2ccc3cnccc3c2)C1]

265 mg of sodium hydride was added with stirring under ice cooling to an N,N-dimethylformamide (10 mL) solution of 500 mg of (S)-6-{3-(tert-butoxycarbonylamino)pyrrolidin-1-ylsulfonyl}isoquinoline obtained in Step 1 of Example 10. After stirring in this state for 30 minutes, 0.8 mL of butyl iodide was added dropwise to the reaction solution, and the mixture was further stirred for 30 minutes for reaction. The reaction was terminated by the dropwise addition of water in small portions under ice cooling to the reaction solution. Then, 50 mL of water was added thereto, followed by three extractions with 50 mL of ether. The combined organic layer was washed with 100 mL of saturated saline and dried over anhydrous sodium sulfate. After filtration, the filtrate was concentrated, and the obtained crude product was purified by silica gel column chromatography (acetone:hexane=1:1) to obtain 350 mg of the compound of interest as a colorless oil (61%).

$^1$H-NMR spectrum (CDCl$_3$, δ ppm): 0.87 (t, J=7.3 Hz, 3H), 1.18-1.23 (m, 2H), 1.34 (s, 9H), 1.39-1.44 (m, 2H), 1.94-2.05 (m, 2H), 2.96-3.07 (m, 2H), 3.18-3.22 (m, 2H), 3.50 (t, J=9.2 Hz, 1H), 3.55 (s, 1H), 4.27 (br s, 1H), 7.80 (d, J=5.5 Hz, 1H), 7.97 (dd, J=1.8, 8.5 Hz, 1H), 8.15 (d, J=8.5 Hz, 1H), 8.38 (s, 1H), 8.70 (d, J=6.1 Hz, 1H), 9.39 (s, 1H)

Step 2

Synthesis of (S)-6-{3-(N-butylamino)pyrrolidin-1-ylsulfonyl}isoquinoline

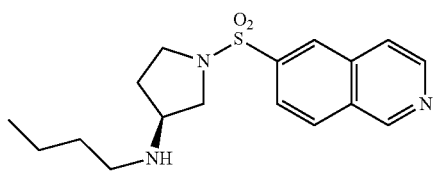 [SMILES: CCCCN[C@H]1CCN(S(=O)(=O)c2ccc3cnccc3c2)C1]

The compound of interest was obtained (pale yellow oil, 85%) according to the method of Step 2 of Example 8 using (S)-6-{3-(N-tert-butoxycarbonyl-N-butylamino)pyrrolidin-1-ylsulfonyl}isoquinoline.

$^1$H-NMR spectrum (CDCl$_3$, δ ppm): 0.81 (t, J=7.0 Hz, 3H), 1.14-1.29 (m, 5H), 1.60-1.66 (m, 1H), 1.99-2.06 (m, 1H), 2.38-2.47 (m, 2H), 3.08 (dd, J=4.9, 10.4 Hz, 1H), 3.23-3.27 (m, 1H), 3.36-3.45 (m, 2H), 3.52 (dd, J=6.1, 10.4 Hz, 1H), 7.80 (d, J=5.5 Hz, 1H), 7.98 (dd, J=1.8, 8.5 Hz, 1H), 8.13 (d, J=8.5 Hz, 1H), 8.39 (s, 1H), 8.69 (d, J=5.5 Hz, 1H), 9.38 (s, 1H)

Step 3

Synthesis of (S)-6-{3-(N-butylamino)pyrrolidin-1-ylsulfonyl}isoquinoline dihydrochloride (Compound 11)

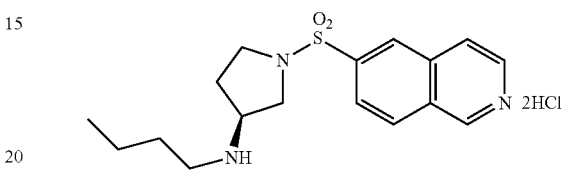

Compound 11 was obtained (white crystal, 78%) using (S)-6-{3-(N-butylamino)pyrrolidin-1-ylsulfonyl}isoquinoline instead of 6-(4-tert-butoxycarbonylpiperazin-1-ylsulfonyl)isoquinoline in Step 2 of Example 1.

$^1$H-NMR spectrum (D$_2$O, δ ppm): 0.76 (t, J=7.3 Hz, 3H), 1.20-1.25 (m, 2H), 1.46-1.52 (m, 2H), 1.94-1.99 (m, 1H), 2.15-2.21 (m, 1H), 2.89-2.92 (m, 2H), 3.18-3.23 (m, 1H), 3.46-3.58 (m, 3H), 3.71-3.74 (m, 1H), 8.20 (d, J=7.9 Hz, 1H), 8.54-8.59 (m, 3H), 8.70 (s, 1H), 9.70 (s, 1H)

mp: 207° C.

[α]$^{25}$$_D$+30.0 (c=0.053, H$_2$O)

Example 12

Synthesis of (S)-6-(2-methyl-1,4-diazepan-1-ylsulfonyl)isoquinoline dihydrochloride (Compound 12)

Step 1

Synthesis of (S)-6-(4-tert-butoxycarbonyl-2-methyl-1,4-diazepan-1-ylsulfonyl)isoquinoline (1) Synthesis of (S)-6-{2-(tert-butoxycarbonyl-3-tert-butyldimethylsiloxypropylamino)-1-methylethylaminosulfonyl}isoquinoline

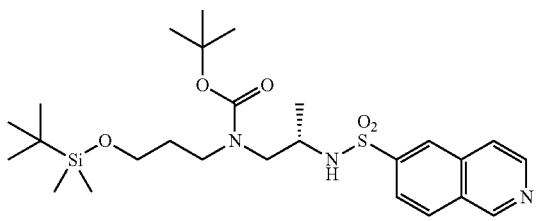 [SMILES: C[C@@H](CN(CCCO[Si](C)(C)C(C)(C)C)C(=O)OC(C)(C)C)NS(=O)(=O)c1ccc2cnccc2c1]

A dichloromethane solution (200 mL) of Reference Compound 9 (5.5 g) was added with stirring at room temperature to a dichloromethane solution (200 mL) of 6-chlorosulfonylisoquinoline (Reference Compound 2) synthesized according to Reference Example 2 from 2 g of 6-aminoisoquinoline (Reference Compound 1), and reacted for 16 hours. After the completion of reaction, the reaction solution was washed with saturated saline and dried over anhydrous sodium sulfate. After filtration, the filtrate was concentrated, and the obtained crude product was purified by silica gel column chromatography (ethyl acetate:hexane=1:1) to obtain 2.7 g of the compound of interest as a colorless oil (31%).

(2) Synthesis of (S)-6-{2-(tert-butoxycarbonyl-3-hydroxypropylamino)-1-methylethylaminosulfonyl}isoquinoline

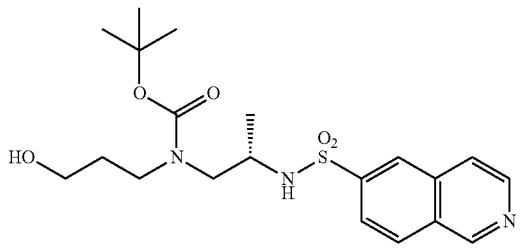 [SMILES: C[C@@H](CN(CCCO)C(=O)OC(C)(C)C)NS(=O)(=O)c1ccc2cnccc2c1]

2.7 g of the compound obtained in (1) was dissolved in 100 mL of tetrahydrofuran. To the solution, a tetrahydrofuran solution (15 mL) of 1 M tetrabutylammonium fluoride was added with stirring at room temperature, and the mixture was then stirred for 12 hours. The reaction solution was diluted with water, followed by extraction with ethyl acetate (100 mL×2). Then, the extract was dried over anhydrous sodium sulfate. After filtration, the filtrate was concentrated, and the obtained crude product was purified by silica gel column chromatography (acetone:hexane=1:1) to obtain 1.5 g of the compound of interest as a colorless oil (71%).

In another synthesis method, a dichloromethane solution (200 mL) of 6-chlorosulfonylisoquinoline (Reference Compound 2) was added with stirring at room temperature to a solution containing 792 mg of (S)-2-amino-1-(tert-butoxycarbonyl-3-hydroxypropylamino)propane (Reference Compound 10) dissolved in 30 mL of dichloromethane further supplemented with 0.8 mL of triethylamine, and reacted for 6 hours. The reaction solution was washed with saturated saline and dried over anhydrous sodium sulfate. After filtration, the filtrate was concentrated, and the obtained crude product was purified by silica gel column chromatography (acetone:hexane=1:1) to obtain 1.05 g of the compound of interest as a colorless oil (87%).

$^1$H-NMR spectrum (CDCl$_3$, δ ppm): 1.12 (s, 1.5H), 1.13 (s, 1.5H), 1.48 (m, 9H), 1.62 (s, 2H), 2.90 (m, 1H), 3.03-3.08 (m, 4H), 3.30-3.32 (m, 1H), 3.50 (s, 2H), 3.62 (s, 1H), 7.78 (d, J=5.5 Hz, 1H), 7.94-7.96 (m, 1H), 8.11-8.12 (m, 1H), 8.41 (s, 1H), 8.69 (d, J=3.7 Hz, 1H), 9.37 (s, 1H)

(3) Synthesis of (S)-6-(4-tert-butoxycarbonyl-2-methyl-1,4-diazepan-1-ylsulfonyl)isoquinoline

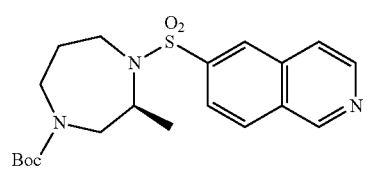 [SMILES: C[C@H]1CN(C(=O)OC(C)(C)C)CCCN1S(=O)(=O)c1ccc2cnccc2c1]

1.5 g of the compound obtained in (2) and 1.2 g of triphenylphosphine were dissolved in 100 mL of tetrahydrofuran.

To the solution, 0.9 mL of diisopropyl azodicarboxylate was added dropwise with stirring at room temperature in an argon atmosphere and then reacted for 16 hours. The reaction solution was diluted with water, followed by extraction with ethyl acetate (100 mL×2). Then, the extract was dried over anhydrous sodium sulfate. After filtration, the filtrate was concentrated, and the obtained crude product was purified by silica gel column chromatography (ethyl acetate:hexane=1:2) to obtain 1.1 g of the compound of interest as a colorless oil (76%).

$^1$H-NMR spectrum (CDCl$_3$, δ ppm): 0.95 (d, J=6.7 Hz, 1.5H), 0.99 (d, J=6.7 Hz, 1.5H), 1.46 (s, 9H), 1.73-1.78 (m, 2H), 3.09-3.14 (m, 2H), 3.52-3.76 (m, 2H), 3.87 (m, 1H), 3.91 (m, 1H), 4.43 (dd, J=6.7, 12.8 Hz, 1H), 7.79 (d, J=5.5 Hz, 1H), 7.92 (t, J=8.2 Hz, 1H), 8.11 (d, J=8.5 Hz, 1H), 8.40 (s, 1H), 8.68 (s, 1H), 9.37 (s, 1H)

Step 2

Synthesis of (S)-6-(2-methyl-1,4-diazepan-1-ylsulfonyl)isoquinoline dihydrochloride (1) Synthesis of (S)-6-(2-methyl-1,4-diazepan-1-ylsulfonyl)isoquinoline

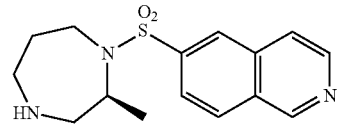 [SMILES: C[C@H]1CNCCCN1S(=O)(=O)c1ccc2cnccc2c1]

1.1 g of (S)-6-(4-tert-butoxycarbonyl-2-methyl-1,4-diazepan-1-ylsulfonyl)isoquinoline was dissolved in 50 mL of dichloromethane, and 1.8 mL of trifluoroacetic acid was added dropwise thereto at room temperature and then reacted for 6 hours. The reaction solution was neutralized with a saturated aqueous solution of sodium bicarbonate, followed by extraction with dichloromethane (50 mL×2). The extract was dried over anhydrous sodium sulfate. After filtration, the filtrate was concentrated, and the obtained crude product was purified by silica gel column chromatography (dichloromethane:methanol:28% ammonia water=10:1:0.05) to obtain 0.4 g of the compound of interest as a white crystal (48%).

$^1$H-NMR spectrum (CDCl$_3$, δ ppm): 0.99 (d, J=6.7 Hz, 3H), 1.66-1.79 (m, 3H), 2.49 (dd, J=8.5, 14.6 Hz, 1H), 2.65-2.69 (m, 1H), 3.01 (td, J=4.1, 9.0 Hz, 1H), 3.16-3.20 (m, 2H), 3.85 (d, J=15.9 Hz, 1H), 4.18 (dd, J=6.4, 13.7 Hz, 1H), 7.78 (d, J=5.5 Hz, 1H), 7.99 (d, J=8.5 Hz, 1H), 8.10 (d, J=8.5 Hz, 1H), 8.45 (s, 1H), 8.67 (d, J=5.5 Hz, 1H), 9.35 (s, 1H)

2) Synthesis of (S)-6-(2-methyl-1,4-diazepan-1-ylsulfonyl)isoquinoline dihydrochloride (Compound 12)

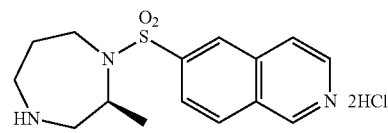 [SMILES: C[C@H]1CNCCCN1S(=O)(=O)c1ccc2cnccc2c1]

3.3 mL of a 4 M hydrochloric acid-dioxane solution was added dropwise with stirring to a dichloromethane (20 mL)

solution of 0.4 g of the compound obtained in (1), and then reacted at room temperature for 3 hours. From the reaction solution, the solvent was distilled off under reduced pressure, and the obtained residue was dissolved in 1 mL of methanol. Then, 10 mL of ethyl acetate was added thereto with vigorous stirring to deposit a white crystal. The deposited white crystal was collected by filtration and dried under reduced pressure to obtain 0.35 g of the compound of interest as a white crystal (71%).

$^1$H-NMR spectrum (D$_2$O, δ ppm): 0.81 (d, J=6.7 Hz, 3H), 1.99 (m, 2H), 3.00 (m, 2H), 3.30 (m, 1H), 3.41 (m, 1H), 3.55 (dd, J=5.8, 14.3 Hz, 1H), 3.84 (m, 1H), 4.46 (m, 1H), 8.23 (d, J=8.5 Hz, 1H), 8.48 (s, 1H), 8.54 (m, 2H), 8.72 (s, 1H), 9.67 (s, 1H)

mp: 232° C.

[α]$^{25}_D$+88.3 (c=0.043, H$_2$O)

Example 13

Synthesis of (S)-6-(2-methylpiperazin-1-ylsulfonyl)isoquinoline dihydrochloride (Compound 13)

Step 1

Synthesis of (S)-6-(4-tert-butoxycarbonyl-2-methylpiperazin-1-ylsulfonyl)isoquinoline

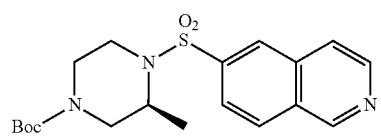 [SMILES: C[C@H]1CN(C(=O)OC(C)(C)C)CCN1S(=O)(=O)c1ccc2cnccc2c1]

The compound of interest was synthesized according to the production method of Step 1 of Example 12 using Reference Compound 7 instead of Reference Compound 9.

$^1$H-NMR spectrum (CDCl$_3$, δ ppm): 0.95 (m, 3H), 1.40 (s, 9H), 2.00 (d, J=12.2 Hz, 2H), 2.56 (t, J=11.6 Hz, 2H), 3.80 (d, J=10.4 Hz, 2H), 4.39 (s, 1H), 7.80 (d, J=5.5 Hz, 1H), 7.88 (d, J=8.5 Hz, 1H), 8.15 (d, J=9.2 Hz, 1H), 8.43 (s, 1H), 8.71 (d, J=5.5 Hz, 1H), 9.40 (s, 1H)

Step 2

Synthesis of (S)-6-(2-methylpiperazin-1-ylsulfonyl)isoquinoline dihydrochloride (Compound 13)

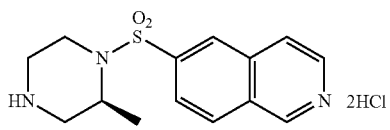 [SMILES: C[C@H]1CNCCN1S(=O)(=O)c1ccc2cnccc2c1]

Compound 13 was synthesized according to the production method of Step 2 of Example 12 using (S)-6-(4-tert-butoxycarbonyl-2-methylpiperazin-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 1.07 (d, J=7.3 Hz, 3H), 2.97 (td, J=4.3, 12.8 Hz, 1H), 3.11 (dd, J=4.3, 13.4 Hz, 1H), 3.20 (d, J=13.4 Hz, 1H), 3.32 (d, J=12.8 Hz, 1H), 3.42-3.48 (m, 1H), 3.96 (d, 15.3 Hz, 1H), 4.44 (t, J=5.8 Hz, 1H), 8.17-8.20 (m, 1H), 8.41-8.46 (m, 1H), 8.56 (d, J=7.3 Hz, 2H), 8.72 (s, 1H), 9.65-9.66 (m, 1H)

mp: 229° C.

[α]$^{25}_D$+39.7 (c=0.045, H$_2$O)

Example 14

Synthesis of (R)-6-(2-methyl-1,4-diazocan-1-ylsulfonyl)isoquinoline dihydrochloride (Compound 14)

Step 1

Synthesis of (R)-6-(4-tert-butoxycarbonyl-2-methyl-1,4-diazocan-1-ylsulfonyl)isoquinoline

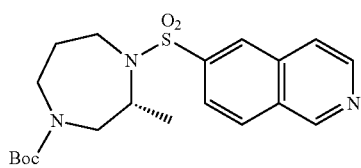 [SMILES: C[C@@H]1CN(C(=O)OC(C)(C)C)CCCN1S(=O)(=O)c1ccc2cnccc2c1]

The compound of interest was synthesized according to the production method of Step 1 of Example 12 using Reference Compound 23 instead of Reference Compound 9.

$^1$H-NMR spectrum (CDCl$_3$, δ ppm): 0.84 (d, J=6.7 Hz, 1.5H), 0.88 (d, J=6.7 Hz, 1.5H), 1.47 (s, 9H), 1.70-1.81 (m, 2H), 1.91 (s, 2H), 2.99-3.09 (m, 1H), 3.32-3.39 (m, 1H), 3.43-3.53 (m, 3H), 3.62 (td, J=4.9, 9.8 Hz, 1H), 4.23-4.28 (m, 1H), 7.79 (d, J=4.3 Hz, 1H), 7.92 (dd, J=1.2, 8.5 Hz, 1H), 8.11 (d, J=8.5 Hz, 1H), 8.38 (s, 1H), 8.68 (d, J=5.5 Hz, 1H), 9.36 (s, 1H)

Step 2

Synthesis of (R)-6-(2-methyl-1,4-diazocan-1-ylsulfonyl)isoquinoline dihydrochloride (Compound 14)

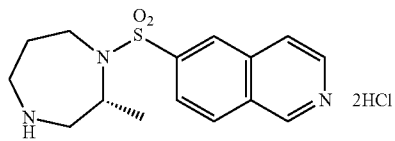 [SMILES: C[C@@H]1CNCCCN1S(=O)(=O)c1ccc2cnccc2c1]

Compound 14 was synthesized according to the production method of Step 2 of Example 12 using (R)-6-(4-tert-butoxycarbonyl-2-methyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.63 (d, J=6.1 Hz, 3H), 1.76-2.01 (m, 4H), 3.19 (m, 4H), 3.41 (dd, J=7.6, 13.7 Hz, 1H), 3.65 (d, J=15.3 Hz, 1H), 4.36-4.41 (m, 1H), 8.26 (d, J=9.2 Hz, 1H), 8.48 (d, J=6.7 Hz, 1H), 8.56 (t, J=8.2 Hz, 2H), 8.75 (s, 1H), 9.35 (s, 1H)

mp: 197° C.

[α]$^{24}_D$−60.8 (c=0.046, H$_2$O)

Example 15

Synthesis of (S)-5-bromo-6-(2-methyl-1,4-diazepan-1-ylsulfonyl)isoquinoline dihydrochloride (Compound 15)

Step 1

Synthesis of (S)-5-bromo-6-(4-tert-butoxycarbonyl-2-methyl-1,4-diazepan-1-ylsulfonyl)isoquinoline

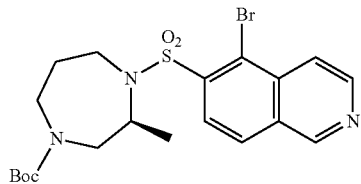 [SMILES: C[C@H]1CN(C(=O)OC(C)(C)C)CCCN1S(=O)(=O)c1ccc2cnccc2c1Br]

The compound of interest was synthesized according to the production method of Step 1 of Example 12 using Reference Compound 4 instead of Reference Compound 2.

$^1$H-NMR spectrum (CDCl$_3$, δ ppm): 0.86 (d, J=6.4 Hz, 1.5H), 0.90 (d, J=6.4 Hz, 1.5H), 1.49 (d, J=2.4 Hz, 9H), 1.83-1.94 (m, 2H), 3.17-3.29 (m, 4H), 3.64-3.71 (m, 2H), 4.29 (t, J=6.1 Hz, 1H), 8.03 (d, J=8.5 Hz, 1H), 8.21 (t, J=4.6 Hz, 1H), 8.32 (dd, J=8.5, 18.9 Hz, 1H), 8.75 (d, J=4.3 Hz, 1H), 9.36 (s, 1H)

Step 2

Synthesis of (S)-5-bromo-6-(2-methyl-1,4-diazepan-1-ylsulfonyl)isoquinoline dihydrochloride (Compound 15)

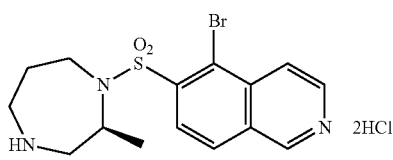 [SMILES: C[C@H]1CNCCCN1S(=O)(=O)c1ccc2cnccc2c1Br]

Compound 15 was synthesized according to the production method of Step 2 of Example 12 using (S)-5-bromo-6-(4-tert-butoxycarbonyl-2-methyl-1,4-diazepan-1-ylsulfonyl)isoquinoline instead of(S)-6-(4-tert-butoxycarbonyl-2-methyl-1,4-diazepan-1-ylsulfonyl)isoquinoline.

$^1$H-NMR spectrum (D$_2$O, δ ppm): 0.79 (d, J=6.7 Hz, 3H), 2.03 (m, 2H), 3.11 (m, 2H), 3.41 (td, J=4.3, 9.2 Hz, 1H), 3.50 (m, 2H), 4.04 (dt, J=5.3, 10.4 Hz, 1H), 4.35 (m, 1H), 8.30 (d, J=9.2 Hz, 1H), 8.36 (d, J=9.2 Hz, 1H), 8.59 (d, J=6.7 Hz, 1H), 8.62 (d, J=6.7 Hz, 1H), 9.57 (s, 1H)

mp: 251° C.

Example 16

Synthesis of 6-(3-methyl-1,4-diazepan-1-ylsulfonyl)isoquinoline dihydrochloride (Compound 16)

Step 1

Synthesis of 6-(4-tert-butoxycarbonyl-3-methyl-1,4-diazepan-1-ylsulfonyl)isoquinoline

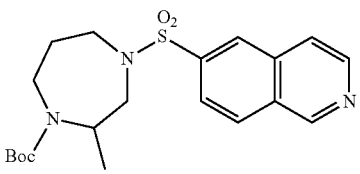 [SMILES: CC1CN(S(=O)(=O)c2ccc3cnccc3c2)CCCN1C(=O)OC(C)(C)C]

The compound of interest was synthesized according to the production method of Step 1 of Example 12 using Reference Compound 12 instead of Reference Compound 9.

$^1$H-NMR spectrum (CDCl$_3$, δ ppm): 1.07 (d, J=6.4 Hz, 1.5H), 1.12 (d, J=6.4 Hz, 1.5H), 1.43 (s, 4.5H), 1.47 (s, 4.5H), 1.95 (br s, 2H), 2.78-2.88 (m, 2H), 3.77-3.94 (m, 3H), 4.32-4.47 (m, 1H), 4.94-4.95 (m, 1H), 7.79 (d, J=6.1 Hz, 1H), 7.89 (d, J=8.5 Hz, 1H), 8.11 (s, 1H), 8.37 (s, 1H), 8.68 (s, 1H), 9.36 (d, J=4.9 Hz, 1H)

Step 2

Synthesis of 6-(3-methyl-1,4-diazepan-1-ylsulfonyl)isoquinoline dihydrochloride (Compound 16)

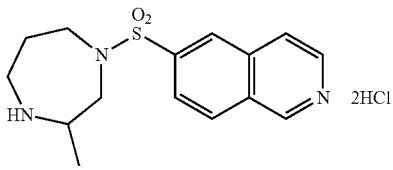 [SMILES: CC1CN(S(=O)(=O)c2ccc3cnccc3c2)CCCN1]

Compound 16 was synthesized according to the production method of Step 2 of Example 12 using 6-(4-tert-butoxycarbonyl-3-methyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 1.24 (d, J=6.7 Hz, 3H), 1.94-1.99 (m, 1H), 2.04-2.10 (m, 1H), 3.16-3.20 (m, 1H), 3.22-3.36 (m, 3H), 3.46-3.51 (m, 1H), 3.56-3.62 (m, 1H), 3.68 (m, 1H), 8.12 (dd, J=1.5, 8.6 Hz, 1H), 8.38 (d, J=6.7 Hz, 1H), 8.52 (dd, J=7.9, 10.4 Hz, 2H), 8.64 (s, 1H), 9.62 (s, 1H)

mp: not measurable due to the hygroscopic property of compound 16

Example 17

Synthesis of 6-(7-methyl-1,4-diazepan-1-ylsulfonyl)isoquinoline dihydrochloride (Compound 17)

Step 1

Synthesis of 6-(4-tert-butoxycarbonyl-7-methyl-1,4-diazepan-1-ylsulfonyl)isoquinoline

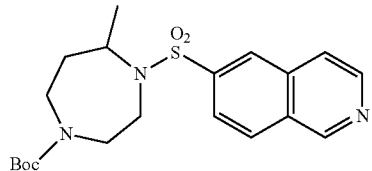 [SMILES: CC1CCN(C(=O)OC(C)(C)C)CCN1S(=O)(=O)c1ccc2cnccc2c1]

The compound of interest was synthesized according to the production method of Step 1 of Example 12 using Reference Compound 13 instead of Reference Compound 9.

$^1$H-NMR spectrum (CDCl$_3$, δ ppm): 0.97-1.11 (m, 3H), 1.40 (s, 9H), 1.54-1.73 (m, 2H), 2.56 (t, J=9.4 Hz, 2H), 3.30 (br s, 2H), 3.78-3.85 (m, 2H), 4.39 (s, 1H), 7.80 (d, J=5.5 Hz, 1H), 7.88 (d, J=8.5 Hz, 1H), 8.14-8.16 (m, 2H), 8.71 (d, J=5.5 Hz, 1H), 9.38 (s, 1H)

Step 2

Synthesis of 6-(7-methyl-1,4-diazepan-1-ylsulfonyl)isoquinoline dihydrochloride (Compound 17)

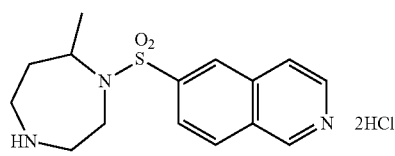 [SMILES: CC1CCNCCN1S(=O)(=O)c1ccc2cnccc2c1]

Compound 17 was synthesized according to the production method of Step 2 of Example 12 using 6-(4-tert-butoxycarbonyl-7-methyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.75 (d, J=6.7 Hz, 3H), 1.63 (m, 2H), 2.26-2.33 (m, 1H), 3.02-3.08 (m, 2H), 3.35-3.42 (m, 2H), 3.95-3.97 (m, 1H), 4.17-4.21 (m, 1H), 8.18 (d, J=8.5 Hz, 1H), 8.39 (d, J=6.7 Hz, 1H), 8.52 (dd, J=11.3, 7.6 Hz, 2H), 8.69 (s, 1H), 9.61 (s, 1H)

mp: 84° C. (absorbed moisture into deliquescence while measured)

Example 18

Synthesis of (R)-6-(2-methyl-1,4-diazepan-1-ylsulfonyl)isoquinoline dihydrochloride (Compound 18)

Step 1

Synthesis of (R)-6-(4-tert-butoxycarbonyl-2-methyl-1,4-diazepan-1-ylsulfonyl)isoquinoline

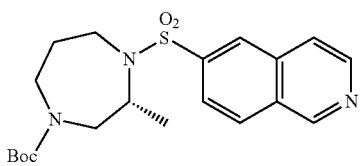 [SMILES: C[C@@H]1CN(C(=O)OC(C)(C)C)CCCN1S(=O)(=O)c1ccc2cnccc2c1]

The compound of interest was synthesized according to the production method of Step 1 of Example 12 using Reference Compound 11 instead of Reference Compound 9.

$^1$H-NMR spectrum (CDCl$_3$, δ ppm): 0.95 (d, J=6.7 Hz, 1.5H), 0.99 (d, J=6.7 Hz, 1.5H), 1.41 (s, 4.5H), 1.43 (s, 4.5H), 1.67-1.91 (m, 2H), 3.06-3.20 (m, 3H), 3.60-3.76 (m, 2H), 3.88 (d, J=15.6 Hz, 0.5H), 3.89 (d, J=15.6 Hz, 0.5H), 4.43 (td, J=6.3, 12.8 Hz, 1H), 7.77 (d, J=6.1 Hz, 1H), 7.91 (t, J=8.9 Hz, 1H), 8.09 (d, J=8.5 Hz, 1H), 8.39 (s, 1H), 8.67 (d, J=5.5 Hz, 1H), 9.35 (s, 1H)

Step 2

Synthesis of (R)-6-(2-methyl-1,4-diazepan-1-ylsulfonyl)isoquinoline dihydrochloride (Compound 18)

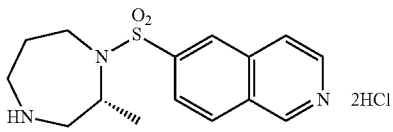 [SMILES: C[C@@H]1CNCCCN1S(=O)(=O)c1ccc2cnccc2c1]

Compound 18 was synthesized according to the production method of Step 2 of Example 12 using (R)-6-(4-tert-butoxycarbonyl-2-methyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.83 (d, J=6.7 Hz, 3H), 1.97-2.09 (m, 2H), 3.00-3.03 (m, 2H), 3.31 (m, 1H), 3.43 (dt, J=4.5, 9.2 Hz, 1H), 3.57 (dd, J=6.1, 14.6 Hz, 1H), 3.86 (dt, J=5.3, 9.9 Hz, 1H), 4.48 (dt, J=5.0, 12.2 Hz, 1H), 8.24 (d, J=9.2 Hz, 1H), 8.49 (d, J=6.1 Hz, 1H), 8.56 (t, J=7.3 Hz, 2H), 8.74 (s, 1H), 9.69 (s, 1H)

mp: 224° C.

$[α]^{24}{}_D$ −84.3 (c=0.043, H$_2$O)

Example 19

Synthesis of (R)-6-(2-ethyl-1,4-diazepan-1-ylsulfonyl)isoquinoline dihydrochloride (Compound 19)

Step 1

Synthesis of (R)-6-(4-tert-butoxycarbonyl-2-ethyl-1,4-diazepan-1-ylsulfonyl)isoquinoline

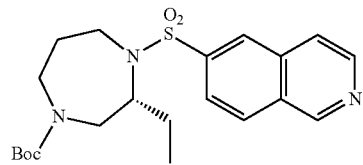 [SMILES: CC[C@@H]1CN(C(=O)OC(C)(C)C)CCCN1S(=O)(=O)c1ccc2cnccc2c1]

The compound of interest was synthesized according to the production method of Step 1 of Example 12 using Reference Compound 2 and using Reference Compound 19 instead of Reference Compound 10.

$^1$H-NMR spectrum (CDCl$_3$, δ ppm): 0.62-0.75 (m, 3H), 1.39-1.46 (m, 11H), 1.70-1.76 (m, 2H), 3.00-3.04 (m, 1H), 3.39-3.61 (m, 4H), 3.81-4.12 (m, 2H), 7.77 (d, J=5.5 Hz, 1H), 7.90 (d, J=9.0 Hz, 1H), 8.09 (d, J=9.0 Hz, 1H), 8.39 (s, 1H), 8.67 (d, J=5.5 Hz, 1H), 9.35 (s, 1H)

Step 2

Synthesis of (R)-6-(2-ethyl-1,4-diazepan-1-ylsulfonyl)isoquinoline dihydrochloride (Compound 19)

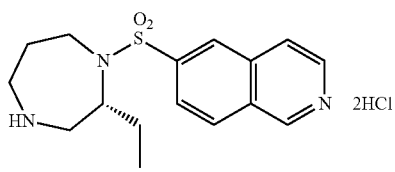 [SMILES: CC[C@@H]1CNCCCN1S(=O)(=O)c1ccc2cnccc2c1]

Compound 19 was synthesized according to the production method of Step 2 of Example 12 using (R)-6-(4-tert-butoxycarbonyl-2-ethyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (DMSO-d$_6$, δ ppm): 0.57 (t, J=7.2H, 3H), 1.48-1.58 (m, 2H), 1.88-1.90 (m, 3H), 3.05-3.08 (m, 2H), 3.24-3.37 (m, 3H), 3.79-3.84 (m, 1H), 4.22-4.26 (m, 1H), 8.16 (d, J=8.5 Hz, 1H), 8.31 (br s, 1H), 8.46 (d, J=8.5 Hz, 1H), 8.70 (s, 3H), 9.13 (br s, 1H), 9.49 (br s, 1H)

mp: 199-200° C.

$[α]^{26}{}_D$ –35.0 (c=0.049, H$_2$O)

Example 20

Synthesis of (R)-6-(2-ethyl-1,4-diazocan-1-ylsulfonyl)isoquinoline dihydrochloride (Compound 20)

Step 1

Synthesis of (R)-6-(4-tert-butoxycarbonyl-2-ethyl-1,4-diazocan-1-ylsulfonyl)isoquinoline

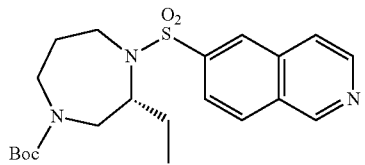 [SMILES: CC[C@@H]1CN(C(=O)OC(C)(C)C)CCCN1S(=O)(=O)c1ccc2cnccc2c1]

The compound of interest was synthesized according to the production method of Step 1 of Example 12 using Reference Compound 2 and using Reference Compound 26 instead of Reference Compound 10.

$^1$H-NMR spectrum (CDCl$_3$, δ ppm): 0.47-0.50 (m, 3H), 1.18-1.27 (m, 2H), 1.46 (s, 9H), 1.71-1.85 (m, 4H), 2.96-3.24 (m, 2H), 3.46-3.94 (m, 5H), 7.78 (d, J=6.0 Hz, 1H), 7.92 (d, J=8.5 Hz, 1H), 8.10 (d, J=8.5 Hz, 1H), 8.36 (s, 1H), 8.67 (d, J=6.0 Hz, 1H), 9.35 (s, 1H)

Step 2

Synthesis of (R)-6-(2-ethyl-1,4-diazocan-1-ylsulfonyl)isoquinoline dihydrochloride (Compound 20)

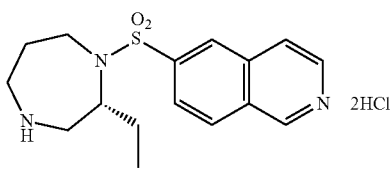 [SMILES: CC[C@@H]1CNCCCN1S(=O)(=O)c1ccc2cnccc2c1]

Compound 20 was synthesized according to the production method of Step 2 of Example 12 using (R)-6-(4-tert-butoxycarbonyl-2-ethyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (DMSO-d$_6$, δ ppm): 0.55 (t, J=7.2 H, 3H), 1.13-1.21 (m, 1H), 1.36-1.42 (m, 1H), 1.60-1.84 (m, 4H), 3.06-3.17 (m, 4H), 3.26-3.48 (m, 2H), 3.63-3.69 (m, 1H), 4.12-4.16 (m, 1H), 8.27 (d, J=8.0 Hz, 1H), 8.57-8.59 (m, 4H), 8.81 (s, 1H), 9.18 (bs, 1H), 9.47 (br s, 1H)

mp: 99-100° C.

$[α]^{25}{}_D$ –21.3 (c=0.043, H$_2$O)

Example 21

Synthesis of 6-(1,4-diazocan-1-ylsulfonyl)isoquinoline dihydrochloride (Compound 21)

Step 1

Synthesis of 6-(4-tert-butoxycarbonyl-1,4-diazocan-1-ylsulfonyl)isoquinoline

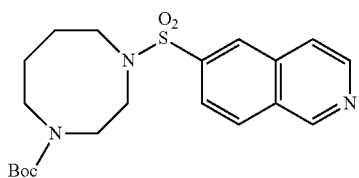 [SMILES: CC(C)(C)OC(=O)N1CCCCN(S(=O)(=O)c2ccc3cnccc3c2)CC1]

The compound of interest was synthesized according to the production method of Step 1 of Example 12 using Reference Compound 21 instead of Reference Compound 9.

$^1$H-NMR spectrum (CDCl$_3$, δ ppm): 1.46 (s, 9H), 1.57 (s, 4H), 1.61-1.67 (m, 2H), 3.24 (s, 2H), 3.28 (t, J=7.0 Hz, 2H), 3.69 (t, J=6.1 Hz, 2H), 7.80 (d, J=6.1 Hz, 1H), 7.91 (dd, J=1.8, 8.5 Hz, 1H), 8.14 (d, J=7.9 Hz, 1H), 8.35 (s, 1H), 8.69 (d, J=5.5 Hz, 1H), 9.38 (s, 1H)

Step 2

Synthesis of 6-(1,4-diazocan-1-ylsulfonyl)isoquinoline dihydrochloride (Compound 21)

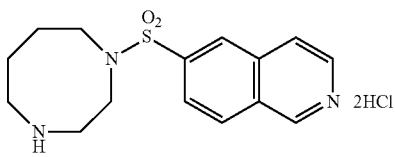 [SMILES: O=S(=O)(c1ccc2cnccc2c1)N1CCCCNCC1]

Compound 21 was synthesized according to the production method of Step 2 of Example 12 using 6-(4-tert-butoxycarbonyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 1.92-1.95 (m, 2H), 2.04-2.08 (m, 2H), 3.05-3.10 (m, 2H), 3.38-3.40 (m, 4H), 3.70-3.74 (m, 2H), 8.11 (d, J=8.5 Hz, 1H), 8.33-8.36 (m, 1H), 8.51 (d, J=8.5 Hz, 1H), 8.54 (d, J=6.7 Hz, 1H), 8.63 (s, 1H), 9.60 (s, 1H)

mp: not measurable due to the hygroscopic property of compound 21

Example 22

Synthesis of 6-(2,2-dimethyl-1,4-diazepan-1-ylsulfonyl)isoquinoline dihydrochloride (Compound 22)

Step 1

Synthesis of 6-{2-(tert-butoxycarbonyl-3-hydroxypropylamino)-1,1-dimethylethylaminosulfonyl}isoquinoline

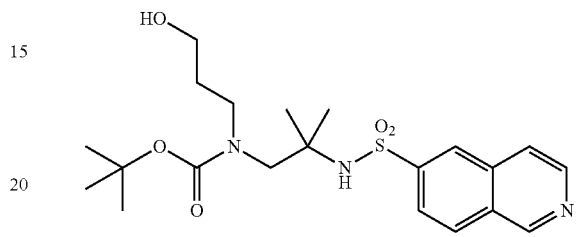

0.7 mL of triethylamine was added to a dichloromethane (20 mL) solution of 550 mg of 2-(benzyloxycarbonylamino)-1-(tert-butoxycarbonyl-3-hydroxypropylamino)-2-methylpropane (Reference Compound 37). To this reaction solution, a dichloromethane solution (100 mL) of 6-chlorosulfonylisoquinoline (Reference Compound 2) synthesized according to Reference Example 2 was added, and the mixture was stirred at room temperature for 16 hours. After the completion of reaction, water was added, followed by extraction with dichloromethane (20 mL×3). The extract was dried over anhydrous sodium sulfate. After filtration, the filtrate was concentrated, and the obtained crude product was purified by silica gel chromatography (acetone:hexane=1:1) to obtain 140 mg of the compound of interest as a brown oil (14%).

$^1$H-NMR spectrum (CDCl$_3$, δ ppm): 1.24 (s, 6H), 1.54 (s, 9H), 1.69-1.77 (m, 3H), 3.16-3.67 (br m, 6H), 5.92 (br s, 1H), 7.75 (d, J=5.5 Hz, 1H), 7.95 (d, J=8.4 Hz, 1H), 8.05 (br s, 1H), 8.40 (s, 1H), 8.65 (d, J=5.3 Hz, 1H), 9.34 (s, 1H)

Step 2

Synthesis of 6-(2,2-dimethyl-1,4-diazepan-1-ylsulfonyl)isoquinoline

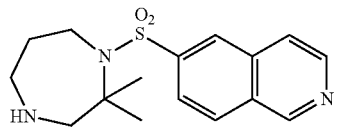 [SMILES: CC1(C)CNCCCN1S(=O)(=O)c1ccc2cnccc2c1]

168 mg of triphenylphosphine was added to a tetrahydrofuran (50 mL) solution of 140 mg of 6-{2-(tert-butoxycarbonyl-3-hydroxypropylamino)-1,1-dimethylethylaminosulfonyl}isoquinoline, then 130 µL of diisopropyl azodicarboxylate was added, and the mixture was stirred at room temperature for 16 hours. After the completion of reaction, water was added, followed by extraction with ethyl acetate (50 mL×3). The extract was dried over anhydrous sodium sulfate. After filtration, the filtrate was concentrated. To a dichloromethane (6 mL) solution of the obtained crude product, 1 mL of trifluoroacetic acid was added, and the mixture was stirred at room temperature for 16 hours. After the completion of reaction, water was added, and the mixture was neutralized with sodium bicarbonate, followed by extraction with dichloromethane (10 mL×3). The extract was dried over anhydrous sodium sulfate. After filtration, the filtrate was concentrated, and the obtained crude product was purified by preparative thin-layer chromatography (ethyl acetate) to obtain 64 mg of the compound of interest as a brown oil (63%).

$^1$H-NMR spectrum (CDCl$_3$, δ ppm): 1.51 (s, 6H), 1.54-1.65 (m, 2H), 1.94 (br s, 1H), 2.80-2.85 (m, 4H), 3.60-3.66 (m, 2H), 7.77 (d, J=6.1 Hz, 1H), 8.03 (dd, J=1.8, 8.5 Hz, 1H), 8.10 (d, J=8.5 Hz, 1H), 8.46 (s, 1H), 8.65 (d, J=6.1 Hz, 1H), 9.34 (s, 1H)

Step 3

Synthesis of 6-(2,2-dimethyl-1,4-diazepan-1-ylsulfonyl)isoquinoline dihydrochloride (Compound 22)

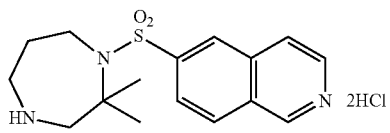 [SMILES: CC1(C)CNCCCN1S(=O)(=O)c1ccc2cnccc2c1]

64 mg of 6-(2,2-dimethyl-1,4-diazepan-1-ylsulfonyl)isoquinoline was dissolved in 5 mL of dichloromethane, and 1 mL of a 1 M hydrochloric acid-diethyl ether solution was added dropwise thereto with stirring and then reacted at room temperature for 3 hours. From the reaction solution, the solvent was distilled off, and the obtained residue was dissolved in 0.5 mL of methanol. Then, 5 mL of ethyl acetate was added with vigorous stirring, and the deposited yellow solid was dried to obtain 68 mg of the compound of interest as a yellow solid (87%).

$^1$H-NMR spectrum (D$_2$O, δ ppm): 1.40 (s, 6H), 1.87-1.94 (m, 2H), 3.16 (t, J=6.1 Hz, 2H), 3.30 (s, 2H), 3.75-3.80 (m, 2H), 8.21 (dd, J=1.8, 8.6 Hz, 1H), 8.41 (d, J=6.56 Hz, 1H), 8.5-8.59 (m, 2H), 8.73 (s, 1H), 9.64 (s, 1H)

Example 23

Synthesis of (R)-5-bromo-6-(2-methyl-1,4-diazocan-1-ylsulfonyl)isoquinoline dihydrochloride (Compound 23)

Step 1

Synthesis of (R)-5-bromo-6-(4-tert-butoxycarbonyl-2-methyl-1,4-diazocan-1-ylsulfonyl)isoquinoline

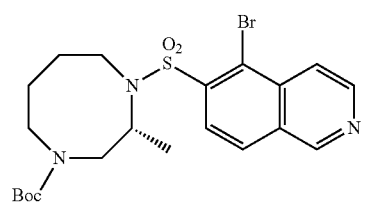 [SMILES: C[C@@H]1CN(C(=O)OC(C)(C)C)CCCCN1S(=O)(=O)c1ccc2cnccc2c1Br]

The compound of interest was synthesized (colorless oil, 41%) according to the production method of Step 1 of Example 12 using Reference Compound 4 instead of Reference Compound 2 and using Reference Compound 23 instead of Reference Compound 9.

$^1$H-NMR spectrum (CDCl$_3$, δ ppm): 0.89 (d, J=6.4 Hz, 1.5H), 0.91 (d, J=6.4 Hz, 1.5H), 1.48 (d, J=8.5 Hz, 9H), 1.83-2.00 (m, 4H), 3.17-3.19 (m, 1H), 3.39-3.52 (m, 4H), 3.93-3.96 (m, 1H), 4.06-4.08 (m, 1H), 8.03 (t, J=9.5 Hz, 1H), 8.22 (s, 1H), 8.30 (d, J=8.5 Hz, 1H), 8.75 (d, J=5.5 Hz, 1H), 9.36 (s, 1H)

Step 2

Synthesis of (R)-5-bromo-6-(2-methyl-1,4-diazocan-1-ylsulfonyl)isoquinoline dihydrochloride (Compound 23)

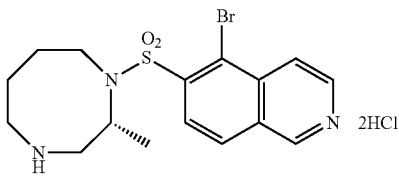 [SMILES: C[C@@H]1CNCCCCN1S(=O)(=O)c1ccc2cnccc2c1Br]

Compound 23 was synthesized (white crystal, 64%) according to the production method of Step 2 of Example 12 using (R)-5-bromo-6-(4-tert-butoxycarbonyl-2-methyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.70 (d, J=6.8 Hz, 3H), 1.79-1.93 (m, 1H), 1.97-2.06 (m, 1H), 3.25 (d, J=8.0 Hz, 2H), 3.27-3.30 (m, 1H), 3.36-3.42 (m, 1H), 3.49-3.54 (m, 1H), 3.36-3.42 (m, 1H), 3.49-3.54 (m, 1H), 4.04 (dt, J=4.5, 15.6 Hz, 1H), 4.17-4.25 (m, 1H), 8.40 (dd, J=8.8, 13.7 Hz, 2H), 8.66 (dd, J=6.9, 12.5 Hz, 2H), 9.63 (s, 1H)

mp: 192° C.

Example 24

Synthesis of (S)-6-(2-methyl-1,4-diazocan-1-ylsulfonyl)isoquinoline dihydrochloride (Compound 24)

Step 1

Synthesis of (S)-6-(4-tert-butoxycarbonyl-2-methyl-1,4-diazocan-1-ylsulfonyl)isoquinoline

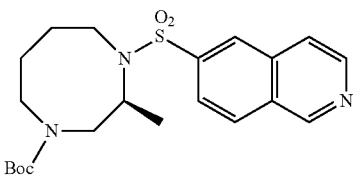 [SMILES: C[C@H]1CN(C(=O)OC(C)(C)C)CCCCN1S(=O)(=O)c1ccc2cnccc2c1]

The compound of interest was synthesized (colorless oil, 32%) according to the production method of Step 1 of Example 12 using Reference Compound 22 instead of Reference Compound 9.

$^1$H-NMR spectrum (CDCl$_3$, δ ppm): 0.84 (d, J=6.7 Hz, 1.5H), 0.88 (d, J=6.7 Hz, 1.5H), 1.47 (s, 9H), 1.70-1.81 (m, 2H), 1.91 (s, 2H), 2.99-3.09 (m, 1H), 3.32-3.39 (m, 1H), 3.43-3.56 (m, 3H), 3.62 (td, J=4.9, 9.8 Hz, 1H), 4.14-4.28 (m, 1H), 7.79 (d, J=4.3 Hz, 1H), 7.92 (dd, J=1.2, 8.5 Hz, 1H), 8.11 (d, J=8.5 Hz, 1H), 8.38 (s, 1H), 8.68 (d, J=5.5 Hz, 1H), 9.37 (s, 1H)

Step 2

Synthesis of (S)-6-(2-methyl-1,4-diazocan-1-ylsulfonyl)isoquinoline dihydrochloride (Compound 24)

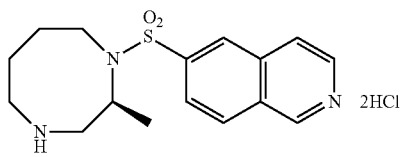 [SMILES: C[C@H]1CNCCCCN1S(=O)(=O)c1ccc2cnccc2c1]

Compound 24 was synthesized (white crystal, 21%) according to the production method of Step 2 of Example 12 using (S)-6-(4-tert-butoxycarbonyl-2-methyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.68 (d, J=7.1 Hz, 3H), 1.77-2.07 (m, 4H), 3.16-3.47 (m, 4H), 3.45 (ddd, J=1.8, 7.9, 13.4 Hz, 1H), 3.69 (dt, J=4.7, 15.2 Hz, 1H), 4.39-4.44 (m, 1H), 8.22 (d, J=8.9 Hz, 1H), 8.36 (t, J=5.1 Hz, 1H), 8.52 (d, J=8.3 Hz, 1H), 8.58 (d, J=6.3 Hz, 1H), 8.72 (s, 1H), 9.61 (s, 1H)

mp: 182° C.

Example 25

Synthesis of (R)-6-(2-methyl-1,4-diazepan-1-ylsulfonyl)-7-fluoroisoquinoline dihydrochloride (Compound 25)

Step 1

Synthesis of (R)-6-{2-(tert-butoxycarbonyl-3-hydroxypropylamino)-1-methylethylaminosulfonyl}-7-fluoroisoquinoline

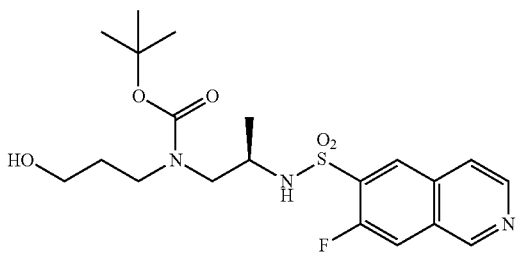 [SMILES: C[C@H](CN(CCCO)C(=O)OC(C)(C)C)NS(=O)(=O)c1cc2ccncc2cc1F]

The compound of interest was synthesized (brown oil, 35%) according to the production method of Step 1 of Example 12 using Reference Compound 5 instead of Reference Compound 2 and using Reference Compound 11 instead of Reference Compound 9.

$^1$H-NMR spectrum (CDCl$_3$, δ ppm): 1.13 (d, J=5.7 Hz, 3H), 1.38 (s, 9H), 1.58 (s, 1H), 1.69 (s, 1H), 1.93 (br s, 1H), 3.03 (dd, J=4.8, 14.5 Hz, 1H), 3.17-3.34 (m, 2H), 3.47 (s, 2H), 3.59-3.75 (m, 2H), 5.54 (br s, 1H), 7.74-7.77 (m, 2H), 8.47 (d, J=7.0 Hz, 1H), 8.66 (s, 1H), 9.31 (s, 1H)

Step 2

Synthesis of (R)-6-(2-methyl-1,4-diazepan-1-ylsulfonyl)-7-fluoroisoquinoline

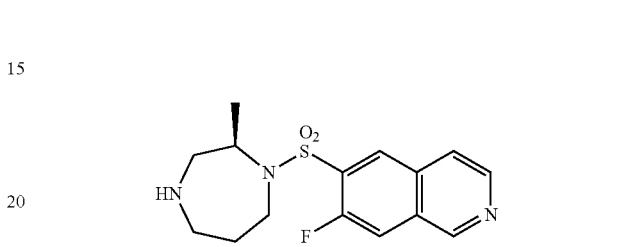

The compound of interest was synthesized (brown oil, 67%) according to the production method of Step 2 of Example 22 using (R)-6-{2-(tert-butoxycarbonyl-3-hydroxypropylamino)-1-methylethylaminosulfonyl}-7-fluoroisoquinoline.

$^1$H-NMR spectrum (CDCl$_3$, δ ppm): 0.96 (d, J=6.7 Hz, 3H), 1.54-1.66 (m, 3H), 2.52-2.59 (m, 1H), 2.72-2.79 (m, 1H), 3.05-3.12 (m, 1H), 3.17-3.29 (m, 2H), 3.93-4.00 (m, 1H), 4.19-4.28 (m, 1H), 7.71 (d, J=10 Hz, 1H), 7.76 (d, J=5.5 Hz, 1H), 8.56 (d, J=6.7 Hz, 1H), 8.65 (d, J=5.5 Hz, 1H), 9.29 (s, 1H)

Step 3

Synthesis of (R)-6-(2-methyl-1,4-diazepan-1-ylsulfonyl)-7-fluoroisoquinoline dihydrochloride (Compound 25)

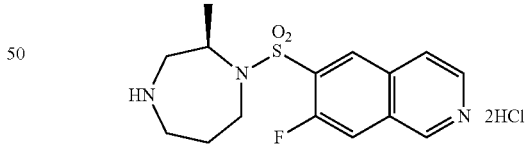

Compound 25 was synthesized (pale yellow crystal, 82%) according to the production method of Step 3 of Example 22 using (R)-6-(2-methyl-1,4-diazepan-1-ylsulfonyl)-7-fluoroisoquinoline.

$^1$H-NMR spectrum (D$_2$O, δ ppm): 0.88 (d, J=6.8 Hz, 3H), 2.05-2.09 (m, 2H), 3.09-3.17 (m, 2H), 3.45-3.50 (m, 2H), 3.56-3.60 (dd, J=5.9, 14.7 Hz, 1H), 3.97-4.00 (dt, J=4.3, 15.7 Hz, 1H), 4.42-4.50 (m, 1H), 8.26 (d, J=9.8 Hz, 1H), 8.44 (d, J=6.1 Hz, 1H), 8.59 (s, 1H), 8.80 (d, J=6.7 Hz, 1H), 9.63 (s, 1H)

$[α]^{24}_D$ −91.3 (c=0.048, H$_2$O)

Example 26

Synthesis of (S)-6-(2-fluoromethyl-1,4-diazepan-1-ylsulfonyl)isoquinoline dihydrochloride (Compound 26)

Step 1

Synthesis of (S)-6-(4-tert-butoxycarbonyl-2-fluoromethyl-1,4-diazepan-1-ylsulfonyl)isoquinoline

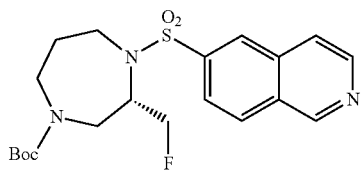 [SMILES: CC(C)(C)OC(=O)N1CCCN(S(=O)(=O)c2ccc3cnccc3c2)[C@H](CF)C1]

The compound of interest was synthesized (colorless oil, 46%) according to the production method of Step 1 of Example 12 using Reference Compound 20 instead of Reference Compound 10.

$^1$H-NMR spectrum (CDCl$_3$, δ ppm): 1.47 (s, 9H), 1.65-1.78 (m, 2H), 3.03-3.26 (m, 2H), 3.42-3.47 (m, 1H), 3.68-3.81 (m, 3H), 3.91-4.00 (m, 1H), 4.35-4.53 (m, 2H), 7.78 (s, 1H), 7.93 (d, J=8.5 Hz, 1H), 8.10 (d, J=8.5 Hz, 1H), 8.40 (s, 1H), 8.67 (br s, 1H), 9.35 (br s, 1H)

Step 2

Synthesis of (S)-6-(2-fluoromethyl-1,4-diazepan-1-ylsulfonyl)isoquinoline dihydrochloride (Compound 26)

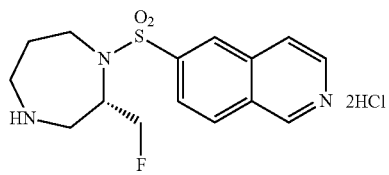 [SMILES: O=S(=O)(c1ccc2cnccc2c1)N1CCCNC[C@H]1CF]

Compound 26 was synthesized (white crystal, 20%) according to the production method of Step 2 of Example 12 using (S)-6-(4-tert-butoxycarbonyl-2-fluoromethyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 2.05-2.12 (m, 2H), 3.06-3.11 (m, 1H), 3.28-3.33 (m, 1H), 3.44-3.52 (m, 2H), 3.75-3.79 (m, 1H), 3.99-4.01 (m, 1H), 4.30-4.34 (m, 1H), 4.40-4.44 (m, 1H), 4.73-4.76 (m, 1H), 8.25 (d, J=8.7 Hz, 1H), 8.44 (br s, 1H), 8.55 (d, J=8.7 Hz, 1H), 8.64 (br s, 1H), 8.74 (s, 1H), 9.71 (br s, 1H)

Example 27

Synthesis of (R)-6-(2-fluoromethyl-1,4-diazocan-1-ylsulfonyl)isoquinoline dihydrochloride (Compound 27)

Step 1

Synthesis of (S)-6-(4-tert-butoxycarbonyl-2-fluoromethyl-1,4-diazocan-1-ylsulfonyl)isoquinoline

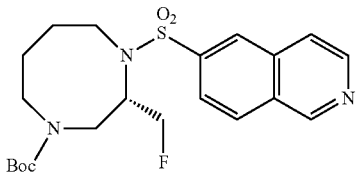 [SMILES: CC(C)(C)OC(=O)N1CCCCN(S(=O)(=O)c2ccc3cnccc3c2)[C@H](CF)C1]

The compound of interest was synthesized (colorless oil, 66%) according to the production method of Step 1 of Example 12 using Reference Compound 27 instead of Reference Compound 10.

$^1$H-NMR spectrum (CDCl$_3$, δ ppm): 1.44 (s, 9H), 1.71-1.89 (m, 4H), 3.12-3.16 (m, 1H), 3.28-3.32 (m, 1H), 3.44-3.48 (m, 2H), 3.57-3.61 (m, 2H), 3.71-3.75 (m, 1H), 4.31-4.47 (m, 2H), 7.93 (d, J=8.0 Hz, 1H), 8.09 (d, J=8.0 Hz, 2H), 8.37 (s, 1H), 8.67 (br s, 1H), 9.35 (br s, 1H)

Step 2

Synthesis of (R)-6-(2-fluoromethyl-1,4-diazocan-1-ylsulfonyl)isoquinoline dihydrochloride (Compound 27)

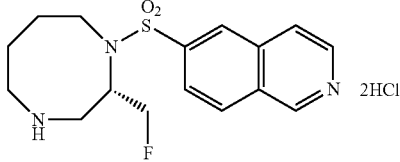 [SMILES: O=S(=O)(c1ccc2cnccc2c1)N1CCCCNC[C@H]1CF ; "2HCl"]

Compound 27 was synthesized (white crystal, 50%) according to the production method of Step 2 of Example 12 using (S)-6-(4-tert-butoxycarbonyl-2-fluoromethyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 1.59-1.60 (m, 1H), 1.78-1.80 (m, 2H), 1.87-1.97 (m, 1H), 3.10-3.17 (m, 2H), 3.30-3.33 (m, 2H), 3.69-3.72 (m, 2H), 4.26-4.30 (m, 1H), 4.35-4.39 (m, 1H), 4.55-4.65 (m, 1H), 8.18 (d, J=8.5 Hz, 1H), 8.33 (br s, 1H), 8.46 (d, J=8.5 Hz, 1H), 8.56 (br s, 1H), 8.73 (s, 1H), 9.09 (br s, 1H)

$[α]^{24}_D$ −52.9 (c=0.034, H$_2$O)

Example 28

Synthesis of (S)-6-(2-methyl-1,4-diazonan-1-ylsulfonyl)isoquinoline dihydrochloride (Compound 28)

Step 1

Synthesis of (S)-6-(4-tert-butoxycarbonyl-2-methyl-1,4-diazonan-1-ylsulfonyl)isoquinoline

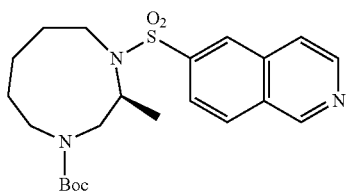 [SMILES: C[C@H]1CN(C(=O)OC(C)(C)C)CCCCCN1S(=O)(=O)c1ccc2cnccc2c1]

The compound of interest was synthesized (colorless oil, 45%) according to the production method of Step 1 of Example 12 using Reference Compound 30 instead of Reference Compound 10.

$^1$H-NMR spectrum (CDCl$_3$, δ ppm): 0.92 (d, J=7.1 Hz, 1.5H), 1.14 (d, J=7.1 Hz, 1.5H), 1.59 (s, 9H), 1.68-1.77 (m, 2H), 1.80-1.88 (m, 3H), 1.89-1.98 (m, 1H), 3.14-3.21 (m, 1H), 3.33 (dd, J=8.0, 15.3 Hz, 1H), 3.39-3.46 (m, 3H), 3.70 (s, 1H), 4.07-4.13 (m, 1H), 7.77 (d, J=6.1 Hz, 1H), 7.93 (dd, J=1.8, 8.2 Hz, 1H), 8.09 (d, J=8.5 Hz, 1H), 8.35 (s, 1H), 8.67 (d, J=6.1 Hz, 1H), 9.35 (s, 1H)

Step 2

Synthesis of (S)-6-(2-methyl-1,4-diazocan-1-ylsulfonyl)isoquinoline dihydrochloride (Compound 28)

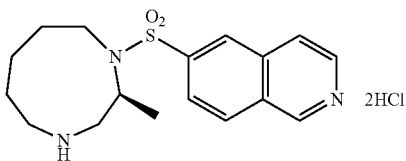 [SMILES: C[C@H]1CNCCCCCN1S(=O)(=O)c1ccc2cnccc2c1 ; "2HCl"]

Compound 28 was synthesized (white crystal, 42%) according to the production method of Step 2 of Example 12 using (S)-6-(4-tert-butoxycarbonyl-2-methyl-1,4-diazonan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.66 (d, J=6.4 Hz, 3H), 1.73-1.84 (m, 4H), 1.87-2.02 (m, 2H), 3.16-3.24 (m, 4H), 3.43-3.49 (m, 2H), 4.44 (s, 1H), 8.27 (d, J=8.2 Hz, 1H), 8.45 (dd, J=6.1, 11.1 Hz, 1H), 8.58 (d, J=5.3 Hz, 1H), 8.61 (d, J=5.9 Hz, 1H), 8.77 (s, 1H), 8.86 (s, 1H)

mp: not measurable due to the hygroscopic property of compound 28

[α]$^{24}_D$+36.9 (c=0.021, H$_2$O)

Example 29

Synthesis of (R)-5-bromo-6-(2-methyl-1,4-diazepan-1-ylsulfonyl)isoquinoline dihydrochloride (Compound 29)

Step 1

Synthesis of (R)-5-bromo-6-(4-tert-butoxycarbonyl-2-methyl-1,4-diazepan-1-ylsulfonyl)isoquinoline

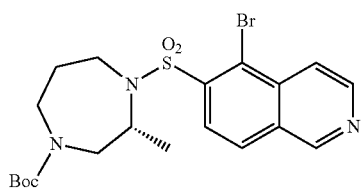 [SMILES: C[C@@H]1CN(C(=O)OC(C)(C)C)CCCN1S(=O)(=O)c1ccc2cnccc2c1Br]

The compound of interest was synthesized (brown oil, 36%) according to the production method of Step 1 of Example 12 using Reference Compound 4 instead of Reference Compound 2 and using Reference Compound 11 instead of Reference Compound 9.

$^1$H-NMR spectrum (CDCl$_3$, δ ppm): 0.84 (d, J=7.2 Hz, 1.5H), 0.94 (d, J=6.5 Hz, 1.5H), 1.48 (s, 9H), 1.78-1.96 (m, 2H), 3.16-3.32 (m, 3H), 3.62-3.74 (m, 2H), 3.98-4.13 (m, 2H), 8.03 (d, J=7.6 Hz, 1H), 8.21 (t, J=4.7 Hz, 1H), 8.32 (d, J=8.5 Hz, 1H), 8.74 (dd, J=2.1, 6.3 Hz, 1H), 9.36 (s, 1H)

Step 2

Synthesis of (R)-5-bromo-6-(2-methyl-1,4-diazepan-1-ylsulfonyl)isoquinoline dihydrochloride (Compound 29)

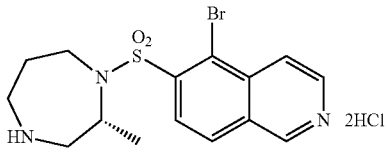 [SMILES: C[C@@H]1CNCCCN1S(=O)(=O)c1ccc2cnccc2c1Br ; "2HCl"]

Compound 29 was synthesized (white crystal, 14%) according to the production method of Step 2 of Example 12 using (R)-5-bromo-6-(4-tert-butoxycarbonyl-2-methyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.84 (d, J=6.7 Hz, 3H), 2.04-2.09 (m, 2H), 3.11-3.18 (m, 2H), 3.45 (dt, J=4.5, 13.7 Hz, 1H), 3.52-3.58 (m, 2H), 4.08 (dt, J=4.7, 15.4 Hz, 1H), 4.34-4.39 (m, 1H), 8.34 (d, J=8.3 Hz, 1H), 8.40 (d, J=8.3 Hz, 1H), 8.64 (s, 2H), 9.60 (s, 1H)

mp: not measurable due to the hygroscopic property of compound 29

Example 30

Synthesis of (R)-6-(6-methyl-1,4-diazocan-1-ylsulfonyl)isoquinoline dihydrochloride (Compound 30)

Step 1

Synthesis of (R)-6-[3-{(tert-butoxycarbonyl-2-hydroxyethylamino)methyl}butylaminosulfonyl]isoquinoline

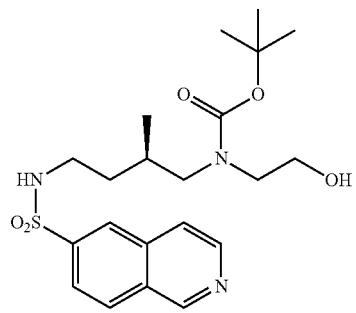 [SMILES: C[C@H](CCNS(=O)(=O)c1ccc2cnccc2c1)CN(CCO)C(=O)OC(C)(C)C]

The compound of interest was synthesized (brown oil, 87%) according to the production method of Step 1 of Example 22 using Reference Compound 24 instead of Reference Compound 36.

$^1$H-NMR spectrum (CDCl$_3$, δ ppm): 0.83 (d, J=6.5 Hz, 3H), 1.43 (s, 9H), 1.52-1.62 (m, 2H), 1.80-1.90 (br m, 2H), 2.80-3.53 (br m, 6H), 3.68-3.82 (br m, 2H), 6.14 (s, 1H), 7.79 (d, J=5.5 Hz, 1H), 7.99 (d, J=9.1 Hz, 1H), 8.13 (d, J=8.5 Hz, 1H), 8.42 (s, 1H), 8.69 (d, J=5.6 Hz, 1H), 9.34 (s, 1H)

Step 2

Synthesis of (R)-6-(6-methyl-1,4-diazocan-1-ylsulfonyl)isoquinoline

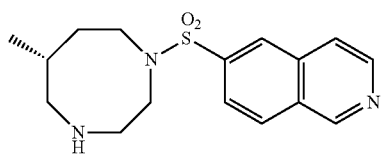 [SMILES: C[C@@H]1CCN(S(=O)(=O)c2ccc3cnccc3c2)CCNC1]

The compound of interest was synthesized (brown oil, 49%) according to the production method of Step 2 of Example 22 using (R)-6-[3-{(tert-butoxycarbonyl-2-hydroxyethylamino)methyl}butylaminosulfonyl]isoquinoline.

$^1$H-NMR spectrum (CDCl$_3$, δ ppm): 0.98 (d, J=6.7 Hz, 3H), 1.61-1.70 (m, 2H), 1.95-2.09 (m, 2H), 2.77 (dd, J=9.2, 13.5 Hz, 1H), 3.06-3.30 (m, 5H), 3.33-3.41 (m, 1H), 3.55-3.60 (m, 1H), 7.78 (d, J=5.49 Hz, 1H), 7.90 (dd, J=1.83, 8.55 Hz, 1H), 8.12 (d, J=8.54 Hz, 1H), 8.33 (s, 1H), 8.68 (d, J=6.1 Hz, 1H), 9.37 (s, 1H)

Step 3

Synthesis of (R)-6-(6-methyl-1,4-diazocan-1-ylsulfonyl)isoquinoline dihydrochloride (Compound 30)

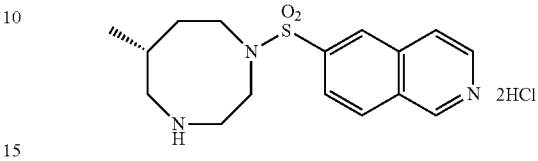

Compound 30 was synthesized (white crystal, 89%) according to the production method of Step 3 of Example 22 using (R)-6-(6-methyl-1,4-diazocan-1-ylsulfonyl)isoquinoline.

$^1$H-NMR spectrum (D$_2$O, δ ppm): 0.99 (d, J=6.6 Hz, 3H), 1.64-1.71 (m, 1H), 1.87-1.90 (m, 1H), 2.15 (br s, 1H), 3.10-3.15 (m, 2H), 3.30-3.44 (m, 4H), 3.50-3.57 (m, 1H), 3.61-3.66 (m, 1H), 8.17 (d, J=8.5 Hz, 1H), 8.44 (d, J=6.6 Hz, 1H), 8.56-8.59 (m, 2H), 8.68 (s, 1H), 9.67 (s, 1H)

$[α]^{25}_D$ +9.7 (c=0.059, H$_2$O)

Example 31

Synthesis of (R)-6-(7-methyl-1,4-diazocan-1-ylsulfonyl)isoquinoline dihydrochloride (Compound 31)

Synthesis of (R)-6-{2-(tert-butoxycarbonyl-4-hydroxy-3-methylbutylamino)ethylaminosulfonyl}isoquinoline

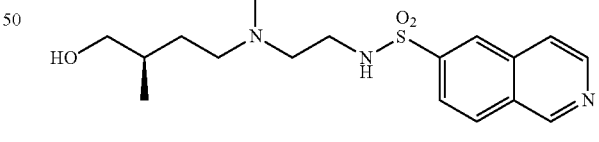

The compound of interest was synthesized (brown oil, 82%) according to the production method of Step 1 of Example 22 using Reference Compound 25 instead of Reference Compound 36.

$^1$H-NMR spectrum (CDCl$_3$, δ ppm): 0.85 (d, J=6.6 Hz, 3H), 1.45 (s, 9H), 1.49-1.66 (br m, 4H), 3.04-3.50 (m, 8H), 5.76 (br s, 1H), 7.78 (d, J=5.5 Hz, 1H), 7.96 (d, J=7.9 Hz, 1H), 8.12 (d, J=8.4 Hz, 1H), 8.40 (s, 1H), 8.68 (d, J=5.7 Hz, 1H), 9.37 (s, 1H)

Step 2

Synthesis of (R)-6-(7-methyl-1,4-diazocan-1-ylsulfonyl)isoquinoline

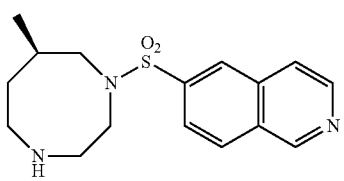 [SMILES: C[C@@H]1CCNCCN(S(=O)(=O)c2ccc3cnccc3c2)C1]

The compound of interest was synthesized (brown oil, 52%) according to the production method of Step 2 of Example 22 using (R)-6-{2-(tert-butoxycarbonyl-4-hydroxy-3-methylbutylamino)ethylaminosulfonyl}isoquinoline.

$^1$H-NMR spectrum (CDCl$_3$, δ ppm): 0.95 (d, J=6.6 Hz, 3H), 1.37-1.52 (br m, 2H), 1.89-1.99 (br m, 2H), 2.91-3.20 (m, 6H), 3.24-3.32 (m, 1H), 3.39-3.46 (m, 1H), 7.79 (d, J=5.5 Hz, 1H), 7.91 (d, J=8.5 Hz, 1H), 8.12 (d, J=8.6 Hz, 1H), 8.34 (s, 1H), 8.69 (d, J=6.0 Hz, 1H), 9.37 (s, 1H)

Step 3

Synthesis of (R)-6-(7-methyl-1,4-diazocan-1-ylsulfonyl)isoquinoline dihydrochloride (Compound 31)

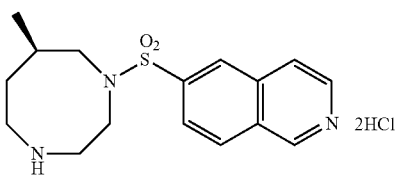 [SMILES: C[C@@H]1CCNCCN(S(=O)(=O)c2ccc3cnccc3c2)C1 ; "2HCl"]

Compound 31 was synthesized (white crystal, 83%) according to the production method of Step 3 of Example 22 using (R)-6-(7-methyl-1,4-diazocan-1-ylsulfonyl)isoquinoline.

$^1$H-NMR spectrum (D$_2$O, δ ppm): 0.85 (d, J=6.7 Hz, 3H), 1.61-1.70 (m, 1H), 1.92-2.06 (m, 2H), 2.92-2.99 (m, 1H), 3.19-3.26 (m, 1H), 3.26-3.34 (m, 2H), 3.35-3.43 (m, 2H), 3.44-3.51 (m, 1H), 3.60-3.68 (m, 1H), 8.17 (dd, J=1.8, 9.2 Hz, 1H), 8.42 (d, J=6.1 Hz, 1H), 8.53-8.58 (m, 2H), 8.67 (s, 1H), 9.66 (s, 1H)

[α]$^{24}_D$ +9.6 (c=0.050, H$_2$O)

Example 32

Synthesis of (S)-6-(7-methyl-1,4-diazepan-1-ylsulfonyl)isoquinoline dihydrochloride (Compound 32)

Step 1

Synthesis of (R)-6-{2-(3-hydroxybutyl-tert-butoxycarbonylamino)ethylaminosulfonyl}isoquinoline

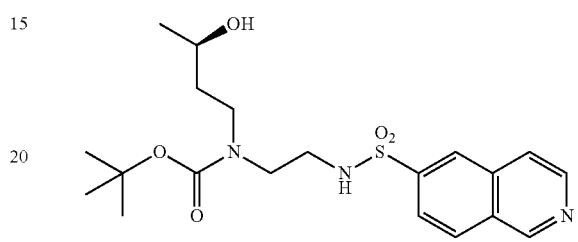

The compound of interest was synthesized (pale yellow oil, 74%) according to the production method of Step 1 of Example 12 using Reference Compound 14 instead of Reference Compound 9.

$^1$H-NMR spectrum (CDCl$_3$, δ ppm): 1.15 (d, J=7.3 Hz, 3H), 1.43 (s, 9H), 1.46-1.50 (m, 2H), 1.91 (br s, 1H), 3.02 (br s, 1H), 3.17 (s, 3H), 3.44 (br s, 1H), 3.69 (br s, 1H), 3.80 (s, 1H), 6.22 (br s, 1H), 7.79 (d, J=6.6 Hz, 1H), 7.97 (d, J=8.2 Hz, 1H), 8.13 (d, J=7.3 Hz, 1H), 8.41 (s, 1H), 8.69 (d, J=5.8 Hz, 1H), 9.36 (s, 1H)

Step 2

Synthesis of (S)-6-(7-methyl-1,4-diazepan-1-ylsulfonyl)isoquinoline dihydrochloride (Compound 32)

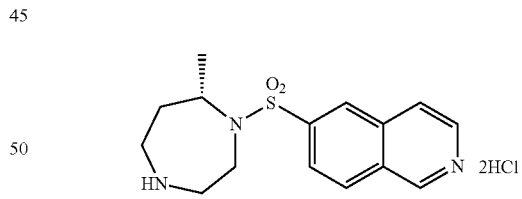

Compound 32 was obtained (white crystal, 50%) by synthesis according to the production method of Step 2 of Example 22 using (R)-6-{2-(3-hydroxybutyl-tert-butoxycarbonylamino)ethylaminosulfonyl}isoquinoline.

$^1$H-NMR spectrum (D$_2$O, δ ppm): 0.80 (d, J=6.1 Hz, 3H), 1.63-1.72 (m, 1H), 2.34 (dt, J=7.1, 17.6 Hz, 1H), 3.04-3.15 (m, 2H), 3.39-3.47 (m, 3H), 4.00 (d, J=16.9 Hz, 1H), 4.23 (dt, J=6.3, 9.7 Hz, 1H), 8.22 (dd, J=1.8, 8.5 Hz, 1H), 8.42 (d, J=7.4 Hz, 1H), 8.54 (d, J=9.0 Hz, 1H), 8.57 (d, J=6.6 Hz, 1H), 8.73 (s, 1H), 9.64 (s, 1H)

mp: not measurable due to the hygroscopic property of compound 32

Example 33

Synthesis of (R)-6-(2-methyl-1,4-diazonan-1-ylsulfonyl)isoquinoline dihydrochloride (Compound 33)

Step 1

Synthesis of (R)-6-(4-tert-butoxycarbonyl-2-methyl-1,4-diazonan-1-ylsulfonyl)isoquinoline

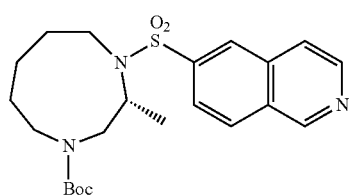 [SMILES: C[C@@H]1CN(C(=O)OC(C)(C)C)CCCCCN1S(=O)(=O)c1ccc2cnccc2c1]

The compound of interest was synthesized (colorless oil, 72%) according to the production method of Step 1 of Example 12 using Reference Compound 31 instead of Reference Compound 10.

$^1$H-NMR spectrum (CDCl$_3$, δ ppm): 0.91 (d, J=7.1 Hz, 1.5H), 1.13 (d, J=7.1 Hz, 1.5H), 1.47 (s, 9H), 1.70-1.80 (m, 2H), 1.85 (br s, 3H), 1.93-1.98 (m, 1H), 3.20-3.27 (m, 1H), 3.37 (dd, J=6.8, 15.3 Hz, 1H), 3.40-3.49 (m, 3H), 3.67 (s, 1H), 4.11 (br s, 1H), 7.78 (d, J=6.1 Hz, 1H), 7.97 (dd, J=1.8, 8.2 Hz, 1H), 8.11 (d, J=8.5 Hz, 1H), 8.39 (s, 1H), 8.69 (d, J=6.1 Hz, 1H), 9.36 (s, 1H)

Step 2

Synthesis of (R)-6-(2-methyl-1,4-diazonan-1-ylsulfonyl)isoquinoline dihydrochloride (Compound 33)

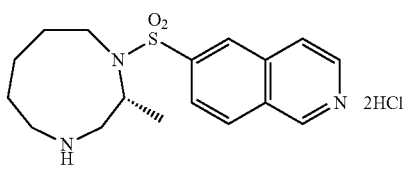 [SMILES: C[C@@H]1CNCCCCCN1S(=O)(=O)c1ccc2cnccc2c1 ; "2HCl"]

Compound 33 was synthesized (white crystal, 44%) according to the production method of Step 2 of Example 12 using (R)-6-(4-tert-butoxycarbonyl-2-methyl-1,4-diazonan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.63 (d, J=4.7 Hz, 3H), 1.69-1.89 (m, 6H), 2.95-3.20 (m, 4H), 3.42-3.48 (m, 2H), 4.42 (br s, 1H), 8.24 (dd, J=2.1, 8.9 Hz, 1H), 8.40 (dd, J=3.0, 6.2 Hz, 1H), 8.57 (d, J=8.3 Hz, 1H), 8.58 (d, J=6.8 Hz, 1H), 8.73 (s, 1H), 9.63 (s, 1H)

mp: not measurable due to the hygroscopic property of compound 33

Example 34

Synthesis of (R)-6-(7-methyl-1,4-diazepan-1-ylsulfonyl)isoquinoline dihydrochloride (Compound 34)

Step 1

Synthesis of (S)-6-{2-(3-hydroxybutyl-tert-butoxycarbonylamino)ethylaminosulfonyl}isoquinoline

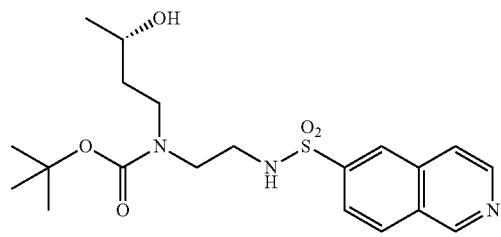 [SMILES: C[C@H](O)CCN(CCNS(=O)(=O)c1ccc2cnccc2c1)C(=O)OC(C)(C)C]

The compound of interest was synthesized (pale yellow oil, 46%) according to the production method of Step 1 of Example 12 using Reference Compound 15 instead of Reference Compound 9.

$^1$H-NMR spectrum (CDCl$_3$, δ ppm): 1.27 (d, J=7.3 Hz, 3H), 1.43 (s, 11H), 1.91 (br s, 1H), 3.02 (s, 1H), 3.17 (s, 1H), 3.50-3.63 (m, 4H), 3.80 (s, 1H), 6.20 (br s, 1H), 7.78 (d, J=6.1 Hz, 1H), 7.97 (d, J=8.5 Hz, 1H), 8.13 (d, J=7.9 Hz, 1H), 8.41 (s, 1H), 8.68 (d, J=5.5 Hz, 1H), 9.36 (s, 1H)

Step 2

Synthesis of (R)-6-(7-methyl-1,4-diazepan-1-ylsulfonyl)isoquinoline

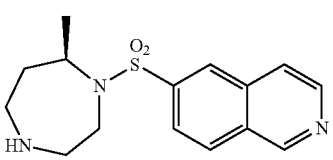 [SMILES: C[C@@H]1CCNCCN1S(=O)(=O)c1ccc2cnccc2c1]

The compound of interest was synthesized (brown oil, 28%) according to the production method of Step 2 of Example 22 using (S)-6-{2-(3-hydroxybutyl-tert-butoxycarbonylamino)ethylaminosulfonyl}isoquinoline.

$^1$H-NMR spectrum (CDCl$_3$, δ ppm): 1.02 (d, J=6.7 Hz, 3H), 1.70 (br s, 2H), 2.15-2.21 (m, 1H), 2.61 (dd, J=9.2, 13.4 Hz, 1H), 2.91-2.95 (m, 3H), 3.12-3.17 (m, 1H), 3.87 (d, J=15.3 Hz, 1H), 4.16-4.20 (m, 1H), 7.78 (d, J=5.5 Hz, 1H), 7.96 (d, J=8.5 Hz, 1H), 8.11 (d, J=8.5 Hz, 1H), 8.40 (s, 1H), 8.68 (d, J=5.5 Hz, 1H), 9.35 (s, 1H)

Step 3

Synthesis of (R)-6-(7-methyl-1,4-diazepan-1-ylsulfonyl)isoquinoline dihydrochloride (Compound 34)

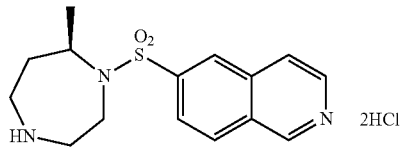 [SMILES: C[C@@H]1CCNCCN1S(=O)(=O)c1ccc2cnccc2c1 ; "2HCl"]

Compound 34 was synthesized (white crystal, 50%) according to the production method of Step 2 of Example 12 using (R)-6-(7-methyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.78 (d, J=6.1 Hz, 3H), 1.67 (dt, J=8.4, 19.1 Hz, 1H), 2.33 (dt, J=7.5, 16.5 Hz, 1H), 3.03-3.13 (m, 2H), 3.41-3.44 (m, 3H), 3.98 (d, J=17.1 Hz, 1H), 4.21-4.24 (m, 1H), 8.23 (dd, J=1.8, 9.2 Hz, 1H), 8.46 (d, J=6.1 Hz, 1H), 8.56 (d, J=3.7 Hz, 1H), 8.57 (s, 1H), 8.74 (s, 1H), 9.68 (s, 1H)

mp: not measurable due to the hygroscopic property

Example 35

Synthesis of (2R,7R)-6-(2,7-dimethyl-1,4-diazepan-1-ylsulfonyl)isoquinoline dihydrochloride (Compound 35)

Step 1

Synthesis of (2R,7R)-6-(4-tert-butoxycarbonyl-2,7-dimethyl-1,4-diazepan-1-ylsulfonyl)isoquinoline

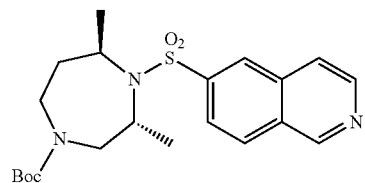 [SMILES: C[C@@H]1CCN(C(=O)OC(C)(C)C)C[C@@H](C)N1S(=O)(=O)c1ccc2cnccc2c1]

The compound of interest was synthesized (colorless oil, 55%) according to the production method of Step 1 of Example 12 using Reference Compound 17 instead of Reference Compound 10.

$^1$H-NMR spectrum (CDCl$_3$, δ ppm): 1.09-1.21 (m, 3H), 1.31-1.43 (m, 3H), 1.49 (s, 9H), 1.88-2.16 (br m, 2H), 3.36-3.79 (br m, 6H), 7.77 (d, J=5.5 Hz, 1H), 7.93 (d, J=8.8 Hz, 1H), 8.10 (d, J=8.8 Hz, 1H), 8.38 (s, 1H), 8.67 (d, J=5.5 Hz, 1H), 9.34 (s, 1H)

Step 2

Synthesis of 6-{(2R,7R)-2,7-dimethyl-1,4-diazepan-1-ylsulfonyl}isoquinoline dihydrochloride (Compound 35)

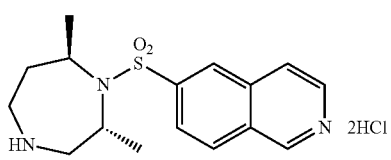 [SMILES: C[C@@H]1CCNC[C@@H](C)N1S(=O)(=O)c1ccc2cnccc2c1 ; "2HCl"]

Compound 35 was synthesized (white crystal, 38%) according to the production method of Step 2 of Example 12 using (2R,7R)-6-(4-tert-butoxycarbonyl-2,7-dimethyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.93 (d, J=6.7 Hz, 3H), 1.36 (d, J=7.3 Hz, 3H), 1.71-1.82 (m, 1H), 2.28-2.37 (m, 1H), 3.18-3.32 (m, 2H), 3.39-3.49 (m, 2H), 3.83-3.92 (m, 1H), 4.21-4.32 (m, 1H), 8.15 (d, J=9.0 Hz, 1H), 8.28 (d, J=6.4 Hz, 1H), 8.45 (d, J=9.4 Hz, 1H), 8.53 (d, J=6.1 Hz, 1H), 8.64 (s, 1H), 9.53 (s, 1H)

$[α]^{25}_D$ −64.3 (c=0.033, H$_2$O)

Example 36)

Synthesis of (2S,7R)-6-(2,7-dimethyl-1,4-diazepan-1-ylsulfonyl)isoquinoline dihydrochloride (Compound 36)

Step 1

Synthesis of (2S,7R)-6-(4-tert-butoxycarbonyl-2,7-dimethyl-1,4-diazepan-1-ylsulfonyl)isoquinoline

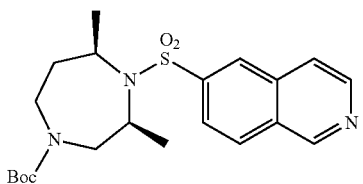 [SMILES: C[C@@H]1CCN(C(=O)OC(C)(C)C)C[C@H](C)N1S(=O)(=O)c1ccc2cnccc2c1]

The compound of interest was synthesized (pale yellow oil, 58%) according to the production method of Step 1 of Example 12 using Reference Compound 18 instead of Reference Compound 9.

$^1$H-NMR spectrum (CDCl$_3$, δ ppm): 1.20-1.35 (m, 6H), 1.44 (s, 9H), 1.80-1.83 (m, 1H), 2.04-2.05 (m, 1H), 3.15-3.20 (m, 1H), 3.42-3.46 (m, 3H), 4.35-4.39 (m, 1H), 4.47-4.50 (m, 1H), 7.82 (s, 1H), 7.93 (d, J=9.0 Hz, 1H), 8.12 (d, J=8.5 Hz, 1H), 8.41 (s, 1H), 8.69 (s, 1H), 9.36 (s, 1H)

Step 2

Synthesis of (2S,7R)-6-(2,7-dimethyl-1,4-diazepan-1-ylsulfonyl)isoquinoline dihydrochloride (Compound 36)

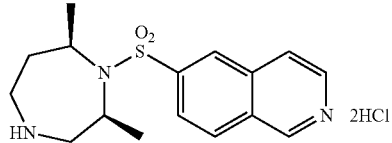 [SMILES: C[C@@H]1CCNC[C@H](C)N1S(=O)(=O)c1ccc2cnccc2c1 ; "2HCl"]

Compound 36 was synthesized (white crystal, 57%) according to the production method of Step 2 of Example 12 using (2S,7R)-6-(4-tert-butoxycarbonyl-2,7-dimethyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 1.10 (d, J=6.5 Hz, 3H), 1.26 (d, J=6.5 Hz, 3H), 1.89-1.96 (m, 1H), 2.25-2.28 (m, 1H), 2.99-3.04 (m, 1H), 3.11-3.14 (m, 1H), 3.27-3.31 (m, 1H), 3.34-3.38 (m, 1H), 4.40-4.42 (m, 1H), 4.50-4.52 (m, 1H), 8.26 (d, J=8.5 Hz, 1H), 8.52 (br s, 1H), 8.56 (d, J=8.5 Hz, 1H), 8.73-8.76 (m, 2H), 9.63 (s, 1H)

$[α]^{25}_D$ −22.5 (c=0.030, H$_2$O)

Example 37

Synthesis of (R)-6-(8-methyl-1,4-diazocan-1-ylsulfonyl)isoquinoline dihydrochloride (Compound 37)

Step 1

Synthesis of (R)-6-(4-tert-butoxycarbonyl-8-methyl-1,4-diazocan-1-ylsulfonyl)isoquinoline

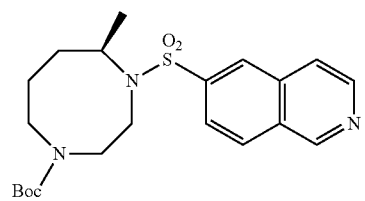 [SMILES: C[C@@H]1CCCN(C(=O)OC(C)(C)C)CCN1S(=O)(=O)c1ccc2cnccc2c1]

The compound of interest was synthesized (colorless oil, 66%) according to the production method of Step 1 of Example 12 using Reference Compound 35 instead of Reference Compound 10.

$^1$H-NMR spectrum (CDCl$_3$, δ ppm): 0.65 (d, J=6.0 Hz, 3H), 1.45 (s, 9H), 1.48-1.66 (m, 4H), 3.07-3.13 (m, 1H), 3.18-3.23 (m, 1H), 3.30-3.37 (m, 1H), 3.50-3.52 (m, 1H), 3.72-3.76 (m, 1H), 4.08-4.14 (m, 2H), 7.78 (d, J=5.5 Hz, 1H), 7.95 (d, J=8.5 Hz, 1H), 8.12 (d, J=8.5 Hz, 1H), 8.38 (s, 1H), 8.68 (d, J=5.5 Hz, 1H), 9.36 (br s, 1H)

Step 2

Synthesis of (R)-6-(8-methyl-1,4-diazocan-1-ylsulfonyl)isoquinoline dihydrochloride

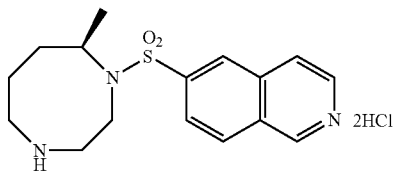 [SMILES: C[C@@H]1CCCNCCN1S(=O)(=O)c1ccc2cnccc2c1 ; "2HCl"]

Compound 37 was synthesized (white crystal, 58%) according to the production method of Step 2 of Example 12 using (R)-6-(4-tert-butoxycarbonyl-8-methyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.56 (d, J=6.0 Hz, 3H), 1.52-1.59 (m, 1H), 1.82-1.93 (m, 3H), 3.16-3.20 (m, 1H), 3.24-3.28 (m, 1H), 3.37-3.50 (m, 3H), 3.71-3.75 (m, 1H), 4.09-4.13 (m, 1H), 7.78 (d, J=8.5 Hz, 1H), 8.37 (d, J=6.5 Hz, 1H), 8.51 (d, J=8.5 Hz, 1H), 8.54 (d, J=6.0 Hz, 1H), 8.71 (s, 1H), 9.36 (s, 1H)

$[α]^{25}_D$ −95.3 (c=0.035, H$_2$O)

Example 38

Synthesis of (R)-6-(2-methyl-1,5-diazocan-1-ylsulfonyl)isoquinoline dihydrochloride (Compound 38)

Step 1

Synthesis of (R)-6-(4-tert-butoxycarbonyl-2-methyl-1,5-diazocan-1-ylsulfonyl)isoquinoline

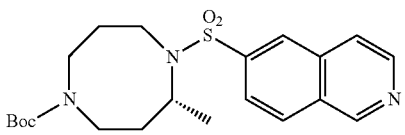 [SMILES: C[C@@H]1CCN(C(=O)OC(C)(C)C)CCCN1S(=O)(=O)c1ccc2cnccc2c1]

The compound of interest was synthesized (colorless oil, 45%) according to the production method of Step 1 of Example 12 using Reference Compound 29 instead of Reference Compound 10.

$^1$H-NMR spectrum (CDCl$_3$, δ ppm): 0.72 (d, J=6.0 Hz, 3H), 1.45 (s, 9H), 1.80-1.86 (m, 1H), 1.93-1.98 (m, 2H), 2.15-2.17 (m, 1H), 2.82-2.95 (m, 3H), 3.17-3.22 (m, 1H), 3.36-3.46 (m, 1H), 3.70-3.73 (m, 1H), 4.05-4.13 (m, 1H), 7.78 (d, J=5.5 Hz, 1H), 7.99 (d, J=8.0 Hz, 1H), 8.12 (d, J=8.5 Hz, 1H), 8.40 (s, 1H), 8.68 (d, J=5.5 Hz, 1H), 9.37 (s, 1H)

Step 2

Synthesis of (R)-6-(2-methyl-1,5-diazocan-1-ylsulfonyl)isoquinoline dihydrochloride (Compound 38)

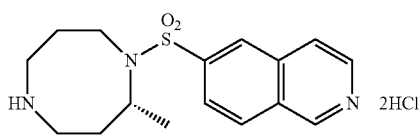 [SMILES: C[C@@H]1CCNCCCN1S(=O)(=O)c1ccc2cnccc2c1 ; "2HCl"]

Compound 38 was synthesized (white crystal, 54%) according to the production method of Step 2 of Example 12 using (R)-6-(4-tert-butoxycarbonyl-2-methyl-1,5-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.58 (d, J=6.5 Hz, 3H), 1.87-1.99 (m, 3H), 2.10-2.20 (m, 1H), 3.13-3.17 (m, 2H), 3.29-3.30 (m, 3H), 3.64-3.69 (m, 1H), 4.11-4.15 (m, 1H), 8.18 (d, J=6.0 Hz, 1H), 8.36 (d, J=6.0 Hz, 1H), 8.49 (d, J=9.5 Hz, 1H), 8.54 (br s, 1H), 8.68 (s, 1H), 9.61 (s, 1H)

$[α]^{25}_D$ −65.9 (c=0.033, H$_2$O)

Example 39

Synthesis of (R)-6-(2-methyl-1,4-diazocan-1-ylsulfonyl)-5-nitroisoquinoline dihydrochloride (Compound 39)

Step 1

Synthesis of (R)-6-(4-tert-butoxycarbonyl-2-methyl-1,4-diazocan-1-ylsulfonyl)-5-nitroisoquinoline

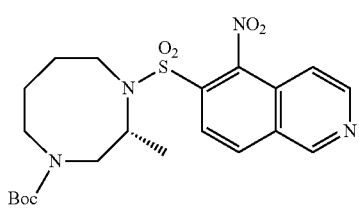

The compound of interest was synthesized (colorless oil, 33%) according to the production method of Step 1 of Example 12 using Reference Compound 6 instead of Reference Compound 2 and using Reference Compound 23 instead of Reference Compound 9.

$^1$H-NMR spectrum (CDCl$_3$, δ ppm): 0.86 (d, J=6.7 Hz, 1.5H), 0.94 (d, J=6.7 Hz, 1.5H), 1.48 (s, 9H), 1.74-1.80 (m, 2H), 1.90-2.00 (m, 2H), 3.14-3.23 (m, 1H), 3.39-3.51 (m, 4H), 3.90-3.95 (m, 1H), 4.06 (s, 1H), 8.03 (t, J=7.0 Hz, 1H), 8.21 (d, J=5.5 Hz, 1H), 8.31 (d, J=8.5 Hz, 1H), 8.75 (d, J=5.5 Hz, 1H), 9.36 (s, 1H)

Step 2

Synthesis of (R)-6-(2-methyl-1,4-diazocan-1-ylsulfonyl)-5-nitroisoquinoline dihydrochloride (Compound 39)

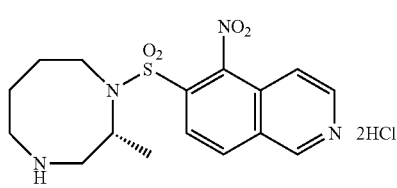 [SMILES: C[C@@H]1CNCCCCN1S(=O)(=O)c1ccc2cnccc2c1[N+](=O)[O-] ; "2HCl"]

Compound 39 was synthesized (white crystal, 74%) according to the production method of Step 2 of Example 12 using (R)-6-(4-tert-butoxycarbonyl-2-methyl-1,4-diazocan-1-ylsulfonyl)-5-nitroisoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.68 (d, J=6.1 Hz, 3H), 1.77-1.82 (m, 1H), 1.84-1.91 (m, 2H), 1.94-2.02 (m, 1H), 3.20-3.26 (m, 3H), 3.35-3.40 (m, 1H), 3.49 (dd, J=5.8, 13.1 Hz, 1H), 4.02 (dd, J=9.2, 15.9 Hz, 1H), 4.14-4.22 (m, 1H), 8.37-8.41 (m, 2H), 8.61-8.64 (m, 2H), 9.56-9.63 (m, 1H)

$[α]^{25}_D$ +65.9 (c=0.064, H$_2$O)

Example 40

Synthesis of (2R,6R)-6-(2,6-dimethylpiperazin-1-ylsulfonyl)isoquinoline dihydrochloride (Compound 40)

Step 1

Synthesis of (2R,6R)-6-(4-tert-butoxycarbonyl-2,6-dimethylpiperazin-1-ylsulfonyl)isoquinoline

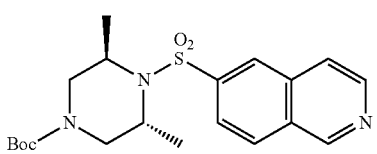 [SMILES: C[C@@H]1CN(C(=O)OC(C)(C)C)C[C@@H](C)N1S(=O)(=O)c1ccc2cnccc2c1]

The compound of interest was synthesized (pale yellow oil, 64%) according to the production method of Step 1 of Example 12 using Reference Compound 8 instead of Reference Compound 9.

$^1$H-NMR spectrum (CDCl$_3$, δ ppm): 1.25 (s, 6H), 1.45 (s, 9H), 3.23 (br s, 1H), 3.45 (br s, 2H), 3.62 (br s, 1H), 4.07-4.17

(m, 2H), 7.77 (d, J=6.0 Hz, 1H), 7.92 (d, J=8.5 Hz, 1H), 8.10 (d, J=9.5 Hz, 1H), 8.39 (s, 1H), 8.68 (d, J=5.5 Hz, 1H), 9.35 (s, 1H)

Step 2

Synthesis of (2R,6R)-6-(2,6-dimethylpiperazin-1-ylsulfonyl)isoquinoline dihydrochloride (Compound 40)

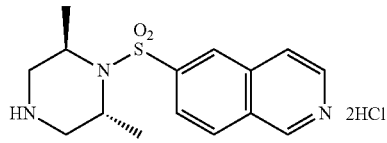 [SMILES: C[C@@H]1CNC[C@@H](C)N1S(=O)(=O)c1ccc2cnccc2c1 ; "2HCl"]

Compound 40 was synthesized (white crystal, 45%) according to the production method of Step 2 of Example 12 using (2R,6R)-6-(4-tert-butoxycarbonyl-2,6-dimethylpiperazin-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 1.23 (d, J=7.0 Hz, 6H), 3.08-3.12 (m, 2H), 3.26-3.29 (m, 2H), 4.34 (br s, 2H), 8.17 (d, J=8.0 Hz, 1H), 8.38 (d, J=5.5 Hz, 1H), 8.50 (d, J=8.5 Hz, 1H), 8.55 (br s, 1H), 8.70 (s, 1H), 9.36 (s, 1H)

$[\alpha]^{25}_D$ –38.2 (c=0.038, H$_2$O)

Example 41

Synthesis of (2S,7S)-6-(2,7-dimethyl-1,4-diazepan-1-ylsulfonyl)isoquinoline dihydrochloride (Compound 41)

Step 1

Synthesis of (2S,7S)-6-(4-tert-butoxycarbonyl-2,7-dimethyl-1,4-diazepan-1-ylsulfonyl)isoquinoline

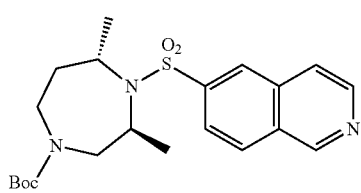 [SMILES: C[C@H]1CCN(C(=O)OC(C)(C)C)C[C@H](C)N1S(=O)(=O)c1ccc2cnccc2c1]

The compound of interest was synthesized (pale yellow oil, 29%) according to the production method of Step 1 of Example 12 using Reference Compound 16 instead of Reference Compound 10.

$^1$H-NMR spectrum (CDCl$_3$, δ ppm): 1.12 (d, J=6.0 Hz, 3H), 1.26 (d, J=6.0 Hz, 3H), 1.48 (s, 9H), 1.62 (br s, 2H), 3.46-3.69 (m, 4H), 4.11-4.18 (m, 2H), 7.77 (d, J=6.0 Hz, 1H), 7.93 (d, J=8.0 Hz, 1H), 8.10 (d, J=8.0 Hz, 1H), 8.38 (s, 1H), 8.67 (d, J=6.0 Hz, 1H), 9.34 (s, 1H)

Step 2

Synthesis of (2S,7S)-6-(2,7-dimethyl-1,4-diazepan-1-ylsulfonyl)isoquinoline dihydrochloride (Compound 41)

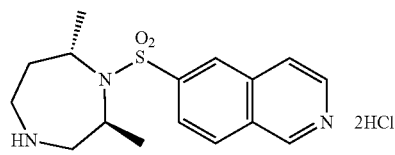 [SMILES: C[C@H]1CCNC[C@H](C)N1S(=O)(=O)c1ccc2cnccc2c1]

Compound 41 was synthesized (white crystal, 36%) according to the production method of Step 2 of Example 12 using (2S,7S)-6-(4-tert-butoxycarbonyl-2,7-dimethyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.90 (d, J=6.5 Hz, 3H), 1.33 (d, J=6.5 Hz, 3H), 1.70-1.78 (m, 1H), 2.26-2.32 (m, 1H), 3.18-3.27 (m, 2H), 3.38-3.44 (m, 2H), 3.82-3.84 (m, 1H), 4.19-4.23 (m, 1H), 8.04 (d, J=8.5 Hz, 1H), 8.13 (br s, 1H), 8.31 (d, J=8.5 Hz, 1H), 8.51 (m, 2H), 9.66 (s, 1H)

Example 42

Synthesis of (S)-6-(2-methyl-1,5-diazocan-1-ylsulfonyl)isoquinoline dihydrochloride (Compound 42)

Step 1

Synthesis of (S)-6-(4-tert-butoxycarbonyl-2-methyl-1,5-diazocan-1-ylsulfonyl)isoquinoline

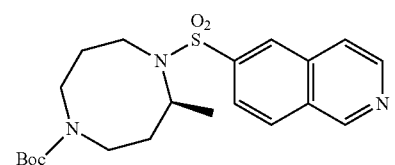 [SMILES: C[C@H]1CCN(C(=O)OC(C)(C)C)CCCN1S(=O)(=O)c1ccc2cnccc2c1]

The compound of interest was synthesized (colorless oil, 58%) according to the production method of Step 1 of Example 12 using Reference Compound 28 instead of Reference Compound 10.

$^1$H-NMR spectrum (CDCl$_3$, δ ppm): 0.72 (d, J=7.0 Hz, 3H), 1.45 (s, 9H), 1.80-1.98 (m, 2H), 2.15-2.20 (m, 2H), 2.82-3.00 (m, 2H), 3.17-3.25 (m, 1H), 3.38-3.45 (m, 1H), 3.63-3.73 (m, 2H), 4.06-4.13 (m, 1H), 7.78 (d, J=5.0 Hz, 1H), 7.99 (d, J=8.5 Hz, 1H), 8.12 (d, J=8.5 Hz, 1H), 8.40 (s, 1H), 8.68 (d, J=5.5 Hz, 1H), 9.37 (s, 1H)

Step 2

Synthesis of (S)-6-(2-methyl-1,5-diazocan-1-ylsulfonyl)isoquinoline dihydrochloride (Compound 42)

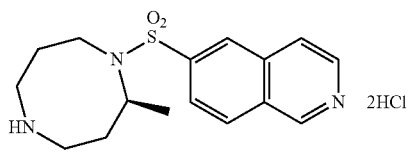 [SMILES: C[C@H]1CCNCCCN1S(=O)(=O)c1ccc2cnccc2c1]

Compound 42 was synthesized (white crystal, 35%) according to the production method of Step 2 of Example 12 using (S)-6-(4-tert-butoxycarbonyl-2-methyl-1,5-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.59 (d, J=6.0 Hz, 3H), 1.85-2.00 (m, 3H), 2.15-2.19 (m, 1H), 3.14-3.22 (m, 2H), 3.30-3.34 (m, 3H), 3.65-3.70 (m, 1H), 4.11-4.15 (m, 1H), 8.17 (d, J=9.0 Hz, 1H), 8.34 (d, J=5.5 Hz, 1H), 8.48 (d, J=9.0 Hz, 1H), 8.54 (s, 1H), 8.67 (s, 1H), 9.62 (s, 1H)

$[\alpha]^{25}_D$+47.9 (c=0.035, H$_2$O)

Example 43

Synthesis of (R)-6-(5-methyl-1,4,7-oxadiazonan-4-ylsulfonyl)isoquinoline dihydrochloride (Compound 43)

Step 1

Synthesis of (R)-6-(7-tert-butoxycarbonyl-5-methyl-1,4,7-oxadiazonan-4-ylsulfonyl)isoquinoline

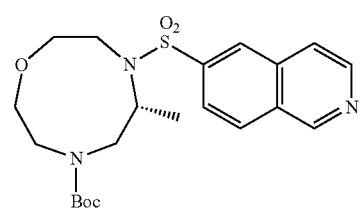 [SMILES: C[C@@H]1CN(C(=O)OC(C)(C)C)CCOCCN1S(=O)(=O)c1ccc2cnccc2c1]

The compound of interest was synthesized (colorless oil, 68%) according to the production method of Step 1 of Example 12 using Reference Compound 32 instead of Reference Compound 10.

$^1$H-NMR spectrum (CDCl$_3$, δ ppm): 0.59 (d, J=7.0 Hz, 3H), 1.51 (s, 9H), 3.03-3.18 (m, 3H), 3.33-3.39 (m, 2H), 3.50-3.53 (m, 1H), 3.81-3.98 (m, 3H), 4.07-4.14 (m, 1H), 4.69 (br s, 1H), 7.78 (d, J=6.0 Hz, 1H), 7.94 (d, J=8.5 Hz, 1H), 8.11 (d, J=8.5 Hz, 1H), 8.36 (s, 1H), 8.67 (d, J=8.5 Hz, 1H), 9.36 (s, 1H)

Step 2

Synthesis of (R)-6-(5-methyl-1,4,7-oxadiazonan-4-ylsulfonyl)isoquinoline dihydrochloride (Compound 43)

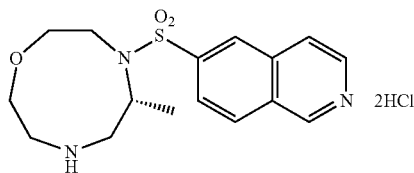 [SMILES: C[C@@H]1CNCCOCCN1S(=O)(=O)c1ccc2cnccc2c1]

Compound 43 was synthesized (white crystal, 77%) according to the production method of Step 2 of Example 12 using (R)-6-(7-tert-butoxycarbonyl-5-methyl-1,4,7-oxadiazonan-4-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.58 (d, J=7.0 Hz, 3H), 3.17 (dd, J=3.2, 14 Hz, 3H), 3.48-3.55 (m, 2H), 3.72-3.77 (m, 2H), 3.81-3.84 (m, 1H), 3.97 (d, J=12.5 Hz, 1H), 4.12-4.17 (m, 1H), 4.45-4.55 (m, 1H), 8.22 (d, J=8.5 Hz, 1H), 8.38 (d, J=6.0 Hz, 1H), 8.52 (d, J=8.5 Hz, 1H), 8.56 (d, J=6.0 Hz, 1H), 8.72 (s, 1H), 9.36 (s, 1H)

$[\alpha]^{25}_D$-38.1 (c=0.035, H$_2$O)

Example 44

Synthesis of (R)-6-(2-methyl-1,4,7-triazonan-1-ylsulfonyl)isoquinoline trihydrochloride (Compound 44)

Step 1

Synthesis of (R)-6-(4,7-di-tert-butoxycarbonyl-2-methyl-1,4,7-triazonan-1-ylsulfonyl)isoquinoline

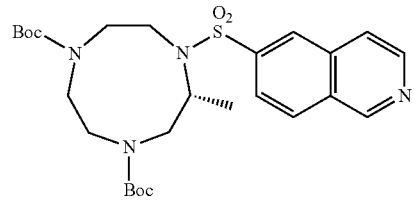 [SMILES: C[C@@H]1CN(C(=O)OC(C)(C)C)CCN(C(=O)OC(C)(C)C)CCN1S(=O)(=O)c1ccc2cnccc2c1]

The compound of interest was synthesized (colorless oil, 43%) according to the production method of Step 1 of Example 12 using Reference Compound 33 instead of Reference Compound 9.

$^1$H-NMR spectrum (CDCl$_3$, δ ppm): 0.52-0.67 (br m, 3H), 1.46 (dd, J=8.2, 13.1 Hz, 9H), 1.56 (s, 9H), 3.06 (br s, 2H), 3.28-3.50 (m, 5H), 3.56 (d, J=14.0 Hz, 1H), 3.84 (d, J=11.6 Hz, 1H), 4.00 (d, J=13.1 Hz, 1H), 4.73 (s, 1H), 7.80 (d, J=5.5

Hz, 1H), 7.95 (d, J=8.5 Hz, 1H), 8.13 (dd, J=8.9, 13.1 Hz, 1H), 8.37 (d, J=16.5 Hz, 1H), 8.69 (t, J=6.1 Hz, 1H), 9.37 (d, J=6.7 Hz, 1H)

Step 2

Synthesis of (R)-6-(2-methyl-1,4,7-triazonan-1-yl-sulfonyl)isoquinoline trihydrochloride (Compound 44)

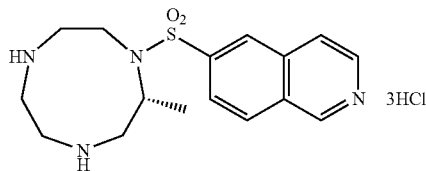 [SMILES: C[C@@H]1CNCCNCCN1S(=O)(=O)c1ccc2cnccc2c1]

Compound 44 was synthesized (white crystal, 34%) according to the production method of Step 2 of Example 12 using (R)-6-(4,7-di-tert-butoxycarbonyl-2-methyl-1,4,7-triazonan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.60 (d, J=4.9 Hz, 3H), 3.14 (t, J=12.8 Hz, 1H), 3.40-3.51 (m, 4H), 3.63-3.68 (m, 2H), 3.71-3.77 (m, 2H), 3.84 (t, J=11.6 Hz, 1H), 4.54-4.59 (m, 1H), 8.28 (d, J=8.5 Hz, 1H), 8.48 (d, J=6.7 Hz, 1H), 8.58 (d, J=6.1 Hz, 1H), 8.61 (d, J=8.5 Hz, 1H), 8.81 (s, 1H), 9.71 (s, 1H)

$[α]^{25}_D$ −59.0 (c=0.040, H$_2$O)

Example 45

Synthesis of 6-(4-glycyl-1,4-diazepan-1-ylsulfonyl)isoquinoline dihydrochloride (Compound 45)

Step 1

Synthesis of 6-(4-tert-butoxycarbonylglycyl-1,4-diazepan-1-ylsulfonyl)isoquinoline

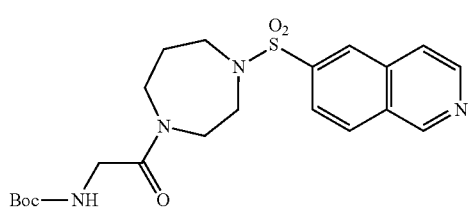 [SMILES: CC(C)(C)OC(=O)NCC(=O)N1CCCN(S(=O)(=O)c2ccc3cnccc3c2)CC1]

300 mg of N-tert-butoxycarbonylglycine was added to a solution containing a dichloromethane (50 mL) solution of 200 mg of 6-(1,4-diazepan-1-ylsulfonyl)isoquinoline supplemented with 150 mg of 1-ethyl-3-(3-dimethylaminopropyl) carbodiimide hydrochloride and 0.2 mL of triethylamine, and the mixture was stirred at room temperature for 16 hours. After the completion of reaction, the reaction solution was washed with saline and dried over anhydrous sodium sulfate. After filtration, the filtrate was concentrated, and the obtained crude product was purified by silica gel column chromatography (ethyl acetate:hexane=1:1) to obtain 146 mg of the compound of interest as a colorless oil (52%).

$^1$H-NMR spectrum (CDCl$_3$, δ ppm): 1.42 (s, 9H), 2.02-2.04 (m, 2H), 2.56 (br s, 1H), 3.25-3.46 (m, 4H), 3.46-3.59 (m, 2H), 3.59-3.77 (m, 2H), 3.88-3.90 (m, 2H), 7.78 (d, J=5.0 Hz, 1H), 7.87 (d, J=8.5 Hz, 1H), 8.12 (d, J=8.5 Hz, 1H), 8.34 (s, 1H), 8.69 (d, J=5.0 Hz, 1H), 9.37 (s, 1H)

Step 2

Synthesis of 6-(4-glycyl-1,4-diazepan-1-ylsulfonyl)isoquinoline dihydrochloride (Compound 45)

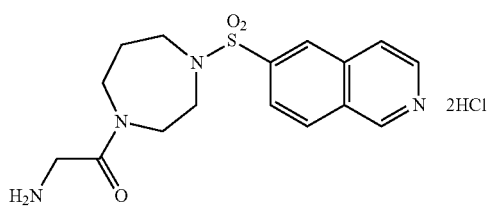 [SMILES: NCC(=O)N1CCCN(S(=O)(=O)c2ccc3cnccc3c2)CC1]

Compound 45 was synthesized according to the production method of Step 2 of Example 12 using 6-(4-tert-butoxycarbonylglycyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 1.99-2.03 (m, 2H), 3.27 (t, J=6.1 Hz, 2H), 3.30-3.31 (m, 2H), 3.46 (t, J=6.1 Hz, 2H), 3.60 (t, J=5.5 Hz, 2H), 4.01-4.05 (m, 2H), 8.14-8.15 (m, 1H), 8.41-8.46 (m, 1H), 8.53 (d, J=6.7 Hz, 2H), 8.61 (s, 1H), 9.62-9.65 (m, 1H)

mp: not measurable due to the hygroscopic property of compound 45

Example 46

Synthesis of (S)-6-(4-glycyl-2-methyl-1,4-diazepan-1-ylsulfonyl)isoquinoline dihydrochloride (Compound 46)

Step 1

Synthesis of (S)-6-(4-tert-butoxycarbonylglycyl-2-methyl-1,4-diazepan-1-ylsulfonyl)isoquinoline

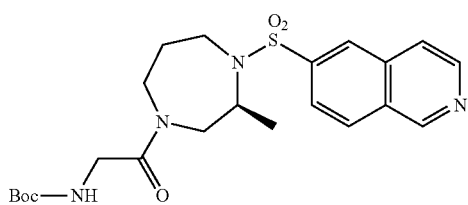 [SMILES: C[C@H]1CN(C(=O)CNC(=O)OC(C)(C)C)CCCN1S(=O)(=O)c1ccc2cnccc2c1]

The compound of interest was synthesized (39%) according to the production method of Step 1 of Example 45 using (S)-6-(2-methyl-1,4-diazepan-1-ylsulfonyl)isoquinoline instead of 6-(1,4-diazepan-1-ylsulfonyl)isoquinoline.

$^1$H-NMR spectrum (CDCl$_3$, δ ppm): 1.12 (d, J=7.0 Hz, 3H), 1.45 (s, 9H), 1.60-1.70 (m, 2H), 2.24 (br s, 1H), 2.79-2.84 (m, 1H), 3.02-3.21 (m, 3H), 3.51-3.53 (m, 1H), 3.80-

3.83 (m, 1H), 4.11-4.15 (m, 2H), 4.45-4.53 (m, 1H), 7.78 (d, J=5.5 Hz, 1H), 7.88 (d, J=8.5 Hz, 1H), 8.07 (d, J=8.5 Hz, 1H), 8.36 (s, 1H), 8.68 (d, J=5.5 Hz, 1H), 9.33 (s, 1H)

Step 2

Synthesis of (S)-6-(4-glycyl-2-methyl-1,4-diazepan-1-ylsulfonyl)isoquinoline dihydrochloride (Compound 46)

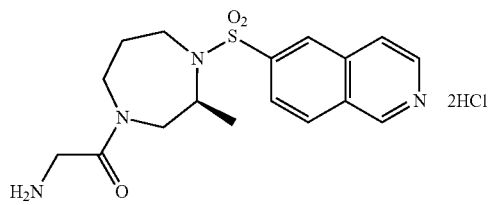 [SMILES: C[C@H]1CN(C(=O)CN)CCCN1S(=O)(=O)c1ccc2cnccc2c1]

Compound 46 was synthesized according to the production method of Step 2 of Example 12 using (S)-6-(4-tert-butoxycarbonylglycyl-2-methyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.96 (d, J=6.0 Hz, 3H), 1.75-1.90 (m, 2H), 3.23-3.31 (m, 5H), 3.50-3.57 (m, 2H), 4.05-4.40 (m, 2H), 7.98-8.28 (m, 2H), 8.41 (d, J=7.5 Hz, 1H), 8.58 (s, 1H), 8.78 (s, 1H), 9.68 (s, 1H)

mp: 190-191° C.

Example 47

Synthesis of (R)-6-(4-glycyl-2-methyl-1,4-diazocan-1-ylsulfonyl)isoquinoline dihydrochloride (Compound 47)

Step 1

Synthesis of (R)-6-(4-tert-butoxycarbonylglycyl-2-methyl-1,4-diazocan-1-ylsulfonyl)isoquinoline

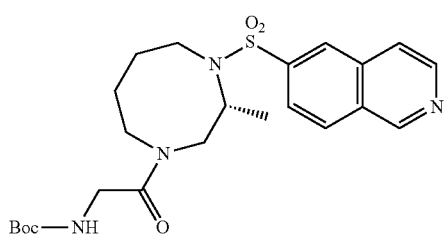 [SMILES: C[C@@H]1CN(C(=O)CNC(=O)OC(C)(C)C)CCCCN1S(=O)(=O)c1ccc2cnccc2c1]

The compound of interest was synthesized (pale yellow oil, 67%) according to the production method of Step 1 of Example 45 using (R)-6-(2-methyl-1,4-diazocan-1-ylsulfonyl)isoquinoline instead of 6-(1,4-diazepan-1-ylsulfonyl)isoquinoline.

$^1$H-NMR spectrum (CDCl$_3$, δ ppm): 0.85 (d, J=6.7 Hz, 3H), 1.47 (s, 9H), 1.52 (m, 4H), 3.03-3.06 (m, 2H), 3.21-3.28 (m, 2H), 3.49 (ddd, J=2.4, 7.9, 14.1 Hz, 1H), 3.65 (dd, J=3.7, 17.1 Hz, 1H), 3.77-3.82 (m, 1H), 3.94-4.00 (m, 1H), 4.37-4.40 (m, 1H), 5.40 (s, 1H), 7.78 (d, J=5.5 Hz, 1H), 7.89 (dd, J=1.8, 8.5 Hz, 1H), 8.09 (d, J=8.5 Hz, 1H), 8.36 (s, 1H), 8.68 (d, J=5.5 Hz, 1H), 9.34 (s, 1H)

Step 2

Synthesis of (R)-6-(4-glycyl-2-methyl-1,4-diazocan-1-ylsulfonyl)isoquinoline dihydrochloride (Compound 47)

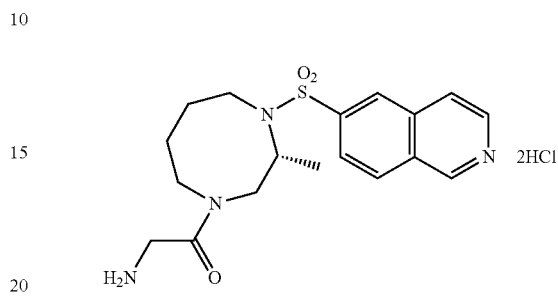

Compound 47 was synthesized (white crystal, 53%) according to the production method of Step 2 of Example 12 using (R)-6-(4-tert-butoxycarbonylglycyl-2-methyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.62 (d, J=6.8 Hz, 3H), 1.78-1.93 (m, 4H), 3.02 (dd, J=11.2, 15.5 Hz, 1H), 3.07-3.13 (m, 1H), 3.20 (dd, J=7.7, 14.7 Hz, 1H), 3.55-3.69 (m, 2H), 3.76 (dd, J=5.6, 14.4 Hz, 1H), 3.97 (d, J=16.6 Hz, 1H), 4.06 (d, J=16.6 Hz, 1H), 4.29-4.36 (m, 1H), 8.20 (d, J=8.2 Hz, 1H), 8.44 (d, J=5.0 Hz, 1H), 8.55 (d, J=8.8 Hz, 1H), 8.58 (d, J=6.6 Hz, 1H), 8.68 (s, 1H), 9.66 (s, 1H)

$[α]^{23}{}_D$ –36.3 (c=0.042, H$_2$O)

Example 48

Synthesis of (R)-6-(4-sarcosyl-2-methyl-1,4-diazocan-1-ylsulfonyl)isoquinoline dihydrochloride (Compound 48)

Step 1

Synthesis of (R)-6-(4-tert-butoxycarbonylsarcosyl-2-methyl-1,4-diazocan-1-ylsulfonyl)isoquinoline

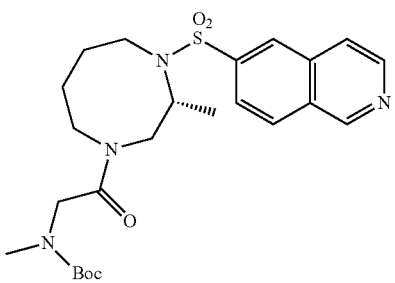 [SMILES: C[C@@H]1CN(C(=O)CN(C)C(=O)OC(C)(C)C)CCCCN1S(=O)(=O)c1ccc2cnccc2c1]

The compound of interest was synthesized (pale yellow oil, 52%) according to the production method of Step 1 of Example 45 using (R)-6-(2-methyl-1,4-diazocan-1-ylsulfonyl)isoquinoline instead of 6-(1,4-diazepan-1-ylsulfonyl)isoquinoline.

$^1$H-NMR spectrum (CDCl$_3$, δ ppm): 0.75 (d, J=6.1 Hz, 3H), 1.46 (s, 9H), 1.63 (s, 1H), 1.72-1.86 (m, 2H), 2.09 (s, 1H), 2.42 (s, 3H), 3.01-3.08 (m, 2H), 3.13 (s, 1H), 3.33 (s, 1H), 3.59-3.73 (m, 2H), 3.80 (d, J=14.0 Hz, 1H), 4.21 (s, 1H), 4.36 (s, 1H), 7.75 (d, J=4.9 Hz, 1H), 7.90 (d, J=7.9 Hz, 1H), 8.08 (d, J=8.5 Hz, 1H), 8.34 (s, 1H), 8.66 (s, 1H), 9.34 (s, 1H)

Step 2

Synthesis of (R)-6-(4-sarcosyl-2-methyl-1,4-diazocan-1-ylsulfonyl)isoquinoline dihydrochloride (Compound 48)

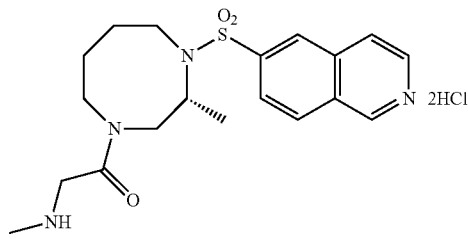 [SMILES: CNCC(=O)N1CCCCN(S(=O)(=O)c2ccc3cnccc3c2)[C@H](C)C1]

Compound 48 was synthesized (white crystal, 53%) according to the production method of Step 2 of Example 12 using (R)-6-(4-tert-butoxycarbonylsarcosyl-2-methyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.57 (d, J=6.7 Hz, 3H), 1.64-1.90 (m, 4H), 2.72 (s, 3H), 2.97 (t, J=13.7 Hz, 1H), 3.03-3.18 (m, 2H), 3.51-3.62 (m, 2H), 3.73 (dd, J=4.3, 14.0 Hz, 1H), 4.02 (d, J=15.9 Hz, 1H), 4.11 (d, J=16.5 Hz, 1H), 4.27-4.32 (m, 1H), 8.18 (d, J=8.5 Hz, 1H), 8.45 (d, J=6.7 Hz, 1H), 8.54 (d, J=5.5 Hz, 2H), 8.66 (s, 1H), 9.60 (s, 1H)

$[α]^{25}_D$ −12.4 (c=0.055, H$_2$O)

Example 49

Synthesis of (S)-5-methyl-6-(2-methyl-1,4-diazepan-1-ylsulfonyl)isoquinoline (Compound 49)

Step 1

Synthesis of (S)-6-(4-tert-butoxycarbonyl-2-methyl-1,4-diazepan-1-ylsulfonyl)-5-methylisoquinoline

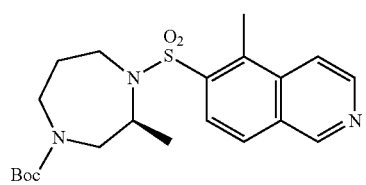 [SMILES: Cc1c(S(=O)(=O)N2CCCN(C(=O)OC(C)(C)C)C[C@@H]2C)ccc2cnccc12]

100 mg of (S)-5-bromo-6-(4-tert-butoxycarbonyl-2-methyl-1,4-diazepan-1-ylsulfonyl)isoquinoline, 15 mg of methylboronic acid, 12 mg of tetrakis(triphenylphosphine)palladium, and 131 mg of potassium phosphate were suspended in 10 mL of 1,4-dioxane and stirred at 100° C. for 10 hours in an argon gas atmosphere. After the completion of reaction, water was added to the reaction solution, followed by extraction with ethyl acetate (30 mL×2). Then, the extract was dried over anhydrous sodium sulfate. After filtration, the filtrate was concentrated, and the obtained crude product was purified by silica gel column chromatography (ethyl acetate:hexane=1:1) to obtain 70 mg of the compound of interest as a colorless oil (81%).

$^1$H-NMR spectrum (CDCl$_3$, δ ppm): 0.95 (d, J=6.4 Hz, 1.5H), 0.99 (d, J=6.4 Hz, 1.5H), 1.48 (s, 4.5H), 1.50 (s, 4.5H), 1.62 (s, 1H), 1.75-1.86 (m, 1H), 2.94 (s, 3H), 3.03-3.20 (m, 2H), 3.70-3.92 (m, 4H), 4.27 (d, J=6.5 Hz, 0.5H), 4.28 (d, J=6.5 Hz, 0.5H), 7.94 (d, J=7.6 Hz, 1H), 7.95 (d, J=7.6 Hz, 1H), 8.18 (t, J=7.9 Hz, 1H), 8.67 (d, J=6.1 Hz, 1H), 9.31 (s, 1H)

Step 2

Synthesis of (S)-5-methyl-6-(2-methyl-1,4-diazepan-1-ylsulfonyl)isoquinoline (Compound 49)

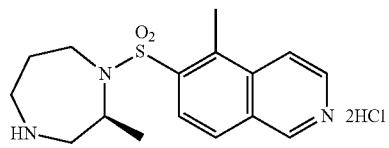 [SMILES: Cc1c(S(=O)(=O)N2CCCNC[C@@H]2C)ccc2cnccc12]

Compound 49 was synthesized (white crystal, 34%) according to the production method of Step 2 of Example 12 using (S)-6-(4-tert-butoxycarbonyl-2-methyl-1,4-diazepan-1-ylsulfonyl)-5-methylisoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.85 (d, J=6.7 Hz, 3H), 2.03 (s, 2H), 2.94 (s, 3H), 3.07-3.13 (m, 2H), 3.43 (td, J=4.7, 9.0 Hz, 1H), 3.48-3.55 (m, 2H), 3.88 (d, J=4.4 Hz, 0.5H), 3.89 (d, J=4.4 Hz, 0.5H), 4.31 (d, J=5.4 Hz, 0.5H), 4.32 (d, J=5.4 Hz, 0.5H), 8.20 (d, J=9.2 Hz, 1H), 8.32 (d, J=9.2 Hz, 1H), 8.53 (d, J=6.7 Hz, 1H), 8.63 (d, J=6.7 Hz, 1H), 9.59 (s, 1H)

mp: 225° C.

Example 50

Synthesis of (S)-1-(2-aminoethylthio)-6-(2-methyl-1,4-diazepan-1-ylsulfonyl)isoquinoline trihydrochloride (Compound 50)

Step 1

Synthesis of (S)-6-(4-tert-butoxycarbonyl-2-methyl-1,4-diazepan-1-ylsulfonyl)isoquinoline 2-oxide

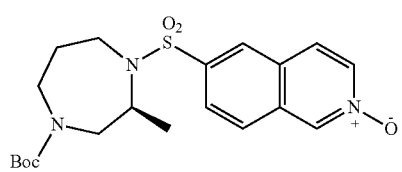

340 mg of (S)-6-(4-tert-butoxycarbonyl-2-methyl-1,4-diazepan-1-ylsulfonyl)isoquinoline was dissolved in 20 mL of dichloromethane, and 244 mg of m-chloroperbenzoic acid was added at 0° C. The reaction solution was stirred at room temperature for 16 hours and then concentrated under reduced pressure, and the obtained crude product was purified by silica gel column chromatography (ethyl acetate:methanol=8:1) to obtain 320 mg of the compound of interest as a colorless oil (91%).

¹H-NMR spectrum (CDCl₃, δ ppm): 1.02 (d, J=6.0 Hz, 3H), 1.43 (s, 9H), 1.50-1.60 (m, 2H), 3.04-3.11 (m, 3H), 3.68-3.92 (m, 3H), 4.35-4.45 (m, 1H), 7.75-7.81 (m, 2H), 7.89 (dd, J=1.5, 7.0 Hz, 1H), 8.22 (dd, J=1.5, 7.0 Hz, 1H), 8.31 (s, 1H), 8.78 (s, 1H)

Step 2

Synthesis of (S)-1-{2-(tert-butoxycarbonylamino)ethylthio}-6-(4-tert-butoxycarbonyl-2-methyl-1,4-diazepan-1-ylsulfonyl)isoquinoline

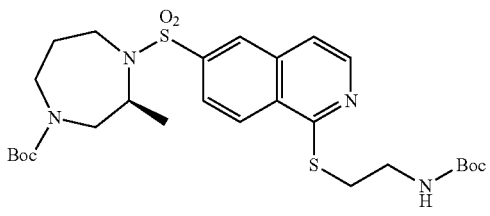 [SMILES: C[C@H]1CN(C(=O)OC(C)(C)C)CCCN1S(=O)(=O)c1ccc2c(SCCNC(=O)OC(C)(C)C)nccc2c1]

320 mg of (S)-6-(4-tert-butoxycarbonyl-2-methyl-1,4-diazepan-1-ylsulfonyl)isoquinoline 2-oxide was dissolved in dichloromethane, and 0.1 mL of ethyl chlorocarbonate, 0.42 mL of 2-(N-tert-butoxycarbonylamino)ethanethiol, and 0.21 mL of triethylamine were added at 0° C. The reaction solution was stirred at room temperature for 16 hours and then concentrated under reduced pressure, and the obtained crude product was purified by silica gel column chromatography (hexane:acetone=4:1) to obtain 223 mg of the compound of interest as a colorless oil (51%).

¹H-NMR spectrum (CDCl₃, δ ppm): 0.88-0.98 (m, 3H), 1.39 (s, 9H), 1.45 (s, 9H), 1.67-1.72 (m, 2H), 3.08-3.15 (m, 3H), 3.50-3.54 (m, 4H), 3.60-3.68 (m, 2H), 3.81-3.92 (m, 2H), 4.38-4.42 (m, 1H), 7.43 (d, J=5.5 Hz, 1H), 7.85 (d, J=9.0 Hz, 1H), 8.27-8.29 (m, 2H), 8.38 (d, J=5.5 Hz, 1H)

Step 3

Synthesis of (S)-1-(2-aminoethylthio)-6-(2-methyl-1,4-diazepan-1-ylsulfonyl)isoquinoline trihydrochloride (Compound 50)

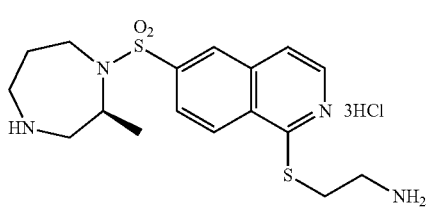 [SMILES: C[C@H]1CNCCCN1S(=O)(=O)c1ccc2c(SCCN)nccc2c1]

Compound 50 was synthesized according to the production method of Step 2 of Example 12 using (S)-1-{2-(tert-butoxycarbonylamino)ethylthio}-6-(4-tert-butoxycarbonyl-2-methyl-1,4-diazepan-1-ylsulfonyl)isoquinoline instead of (S)-6-(4-tert-butoxycarbonyl-2-methyl-1,4-diazepan-1-ylsulfonyl)isoquinoline.

¹H-NMR spectrum (D₂O, δ ppm): 0.96 (d, J=7.0 Hz, 3H), 1.80-1.90 (m, 2H), 2.93-3.05 (m, 2H), 3.15-3.19 (m, 3H), 3.31-3.43 (m, 2H), 3.59 (t, J=7.0 Hz, 2H), 3.68-3.71 (m, 1H), 4.40-4.45 (m, 1H), 7.87 (d, J=6.0 Hz, 1H), 8.10 (d, J=8.5 Hz, 1H), 8.30 (d, J=8.5 Hz, 1H), 8.49 (d, J=6.0 Hz, 1H), 8.62 (s, 1H)

mp: 174-175° C.

[α]²⁵_D +46.4 (c=0.034, H₂O)

Example 51

Synthesis of (R)-1-(2-aminoethylthio)-6-(7-methyl-1,4-diazepan-1-ylsulfonyl)isoquinoline trihydrochloride (Compound 51)

Step 1

Synthesis of (R)-6-(4-tert-butoxycarbonyl-7-methyl-1,4-diazepan-1-ylsulfonyl)isoquinoline 2-oxide

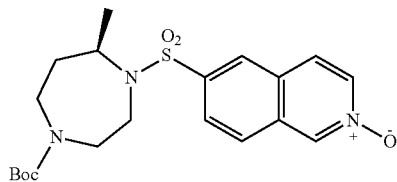

The compound of interest was synthesized (colorless oil, 68%) according to the production method of Step 1 of Example 50 using (R)-6-(4-tert-butoxycarbonyl-7-methyl-1,4-diazepan-1-ylsulfonyl)isoquinoline instead of (S)-6-(4-tert-butoxycarbonyl-2-methyl-1,4-diazepan-1-ylsulfonyl)isoquinoline.

¹H-NMR spectrum (CDCl₃, δ ppm): 1.02 (d, J=6.7 Hz, 3H), 1.44 (s, 9H), 1.62 (s, 1H), 2.12 (s, 1H), 3.18-3.33 (m, 3H), 3.62-3.93 (m, 3H), 4.21 (dd, J=6.7, 13.4 Hz, 1H), 7.80 (d, J=7.3 Hz, 1H), 7.84 (d, J=9.2 Hz, 1H), 7.90 (d, J=8.5 Hz, 1H), 8.23 (d, J=7.3 Hz, 1H), 8.32 (s, 1H), 8.80 (s, 1H)

Step 2

Synthesis of (R)-1-{2-(tert-butoxycarbonylamino)ethylthio}-6-(4-tert-butoxycarbonyl-7-methyl-1,4-diazepan-1-ylsulfonyl)isoquinoline

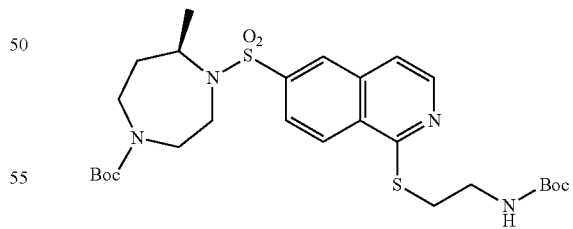

The compound of interest was synthesized (colorless oil, 49%) according to the production method of Step 2 of Example 50 using (R)-6-(4-tert-butoxycarbonyl-7-methyl-1,4-diazepan-1-ylsulfonyl)isoquinoline 2-oxide instead of (S)-6-(4-tert-butoxycarbonyl-2-methyl-1,4-diazepan-1-ylsulfonyl)isoquinoline.

¹H-NMR spectrum (CDCl₃, δ ppm): 0.99 (d, J=6.7 Hz, 3H), 1.28-1.29 (m, 1H), 1.43 (s, 18H), 2.11 (s, 1H), 3.18-3.28 (m, 2H), 3.53 (s, 4H), 3.71-3.78 (m, 2H), 3.85 (d, J=11.0 Hz, 1H), 3.94 (s, 1H), 4.22 (s, 1H), 5.18 (s, 1H), 7.44 (d, J=5.5 Hz, 1H), 7.85 (d, J=8.5 Hz, 1H), 8.28 (s, 1H), 8.31 (d, J=8.5 Hz, 1H), 8.40 (d, J=5.5 Hz, 1H)

Step 3

Synthesis of (R)-1-(2-aminoethylthio)-6-(7-methyl-1,4-diazepan-1-ylsulfonyl)isoquinoline trihydrochloride (Compound 51)

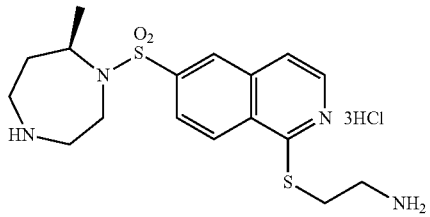 [SMILES: C[C@@H]1CCNCCN1S(=O)(=O)c1ccc2c(SCCN)nccc2c1]

Compound 51 was synthesized (white crystal, 64%) according to the production method of Step 2 of Example 12 using (R)-1-{2-(tert-butoxycarbonylamino)ethylthio}-6-(4-tert-butoxycarbonyl-7-methyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.76 (d, J=6.7 Hz, 3H), 1.63 (dt, J=8.4, 18.7 Hz, 1H), 2.29 (dt, J=7.6, 12.3 Hz, 1H), 2.99-3.04 (m, 2H), 3.32 (t, J=6.1 Hz, 2H), 3.35-3.40 (m, 3H), 3.55 (t, J=6.1 Hz, 2H), 3.93 (d, J=16.5 Hz, 1H), 4.14-4.16 (m, 1H), 7.61 (d, J=5.5 Hz, 1H), 7.92 (d, J=8.5 Hz, 1H), 8.32 (dd, J=1.2, 5.5 Hz, 1H), 8.35 (d, J=8.5 Hz, 1H), 8.41 (s, 1H)

mp: 187° C.

$[α]^{25}_D$ –70.2 (c=0.032, H$_2$O)

Example 52

Synthesis of (R)-1-(2-aminoethylthio)-6-(2-methyl-1,4-diazocan-1-ylsulfonyl)isoquinoline trihydrochloride (Compound 52)

Step 1

Synthesis of (R)-6-(4-tert-butoxycarbonyl-2-methyl-1,4-diazocan-1-ylsulfonyl)isoquinoline 2-oxide

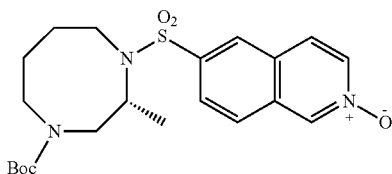

The compound of interest was synthesized (colorless oil, 56%) according to the production method of Step 1 of Example 50 using (R)-6-(4-tert-butoxycarbonyl-2-methyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (CDCl$_3$, δ ppm): 0.84 (d, J=6.7 Hz, 1.5H), 0.94 (d, J=6.7 Hz, 1.5H), 1.47 (s, 9H), 1.65-1.74 (m, 4H), 3.03-3.08 (m, 1H), 3.28-3.60 (m, 5H), 4.21-4.27 (m, 1H), 7.80 (dd, J=7.9, 16.5 Hz, 2H), 7.91 (d, J=8.5 Hz, 1H), 8.22 (d, J=7.3 Hz, 1H), 8.30 (s, 1H), 8.80 (s, 1H)

Step 2

Synthesis of (R)-1-{2-(tert-butoxycarbonylamino)ethylthio}-6-(4-tert-butoxycarbonyl-2-methyl-1,4-diazocan-1-ylsulfonyl)isoquinoline

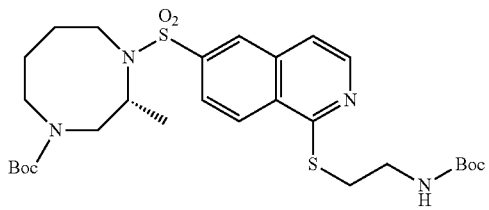 [SMILES: C[C@@H]1CN(C(=O)OC(C)(C)C)CCCCN1S(=O)(=O)c1ccc2c(SCCNC(=O)OC(C)(C)C)nccc2c1]

The compound of interest was synthesized (colorless oil, 44%) according to the production method of Step 2 of Example 50 using (R)-6-(4-tert-butoxycarbonyl-2-methyl-1,4-diazocan-1-ylsulfonyl)isoquinoline 2-oxide instead of (S)-6-(4-tert-butoxycarbonyl-2-methyl-1,4-diazepan-1-ylsulfonyl)isoquinoline.

$^1$H-NMR spectrum (CDCl$_3$, δ ppm): 0.84 (d, J=6.7 Hz, 1.5H), 0.87 (d, J=6.7 Hz, 1.5H), 1.42 (s, 9H), 1.46 (s, 9H), 1.66-1.75 (m, 2H), 1.87-2.01 (m, 2H), 2.97-3.07 (m, 1H), 3.35-3.58 (m, 8H), 4.21-4.35 (m, 2H), 5.19 (s, 1H), 7.45 (d, J=5.5 Hz, 1H), 7.86 (d, J=8.9 Hz, 1H), 8.27 (s, 1H), 8.30 (d, J=8.5 Hz, 1H), 8.40 (d, J=5.5 Hz, 1H)

Step 3

Synthesis of (R)-1-(2-aminoethylthio)-6-(2-methyl-1,4-diazocan-1-ylsulfonyl)isoquinoline trihydrochloride (Compound 52)

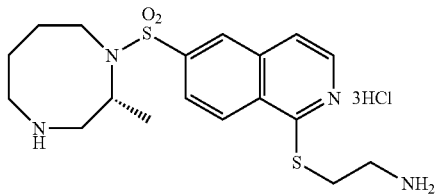 [SMILES: C[C@@H]1CNCCCCN1S(=O)(=O)c1ccc2c(SCCN)nccc2c1]

Compound 52 was synthesized (white crystal, 47%) according to the production method of Step 2 of Example 12 using (R)-1-{2-(tert-butoxycarbonylamino)ethylthio}-6-(4-tert-butoxycarbonyl-2-methyl-1,4-diazocan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 0.60 (d, J=6.1 Hz, 3H), 1.71-1.73 (m, 1H), 1.79-1.89 (m, 2H), 1.96-2.00 (m, 1H), 3.13-3.21 (m, 4H), 3.32 (t, J=6.1 Hz, 2H), 3.41 (dd, J=7.3, 13.4 Hz, 1H), 3.56 (t, J=6.1 Hz, 2H), 3.61-3.64 (m, 1H), 4.31-4.36 (m, 1H), 7.62 (d, J=5.5 Hz, 1H), 7.94 (d, J=8.5 Hz, 1H), 8.33-8.35 (m, 2H), 8.42 (s, 1H)

mp: 209-213° C.

$[α]^{23}_D$ –35.9 (c=0.040, H$_2$O)

Example 53

Synthesis of 6-(1,4-diazepan-1-ylsulfonyl)isoquinolin-1(2H)-one dihydrochloride (Compound 53)

Step 1

Synthesis of 6-(4-tert-butoxycarbonyl-1,4-diazepan-1-ylsulfonyl)isoquinoline 2-oxide

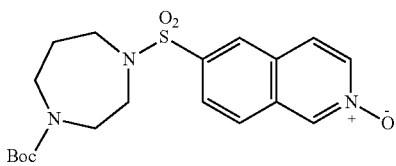

The compound of interest was synthesized (colorless oil, 99%) according to Step 1 of Example 50 using 6-(4-tert-butoxycarbonyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (CDCl$_3$, δ ppm): 1.41 (s, 9H), 1.93-2.04 (m, 2H), 3.29-3.40 (m, 4H), 3.48-3.59 (m, 4H), 7.78 (d, J=7.0 Hz, 1H), 7.82 (d, J=8.5 Hz, 1H), 7.88 (d, J=8.5 Hz, 1H), 8.22 (d, J=7.0 Hz, 1H), 8.27 (s, 1H), 8.78 (s, 1H)

Step 2

Synthesis of 6-(4-tert-butoxycarbonyl-1,4-diazepan-1-ylsulfonyl)-1-methoxyisoquinoline

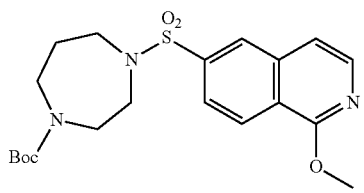 [SMILES: COc1nccc2cc(S(=O)(=O)N3CCCN(C(=O)OC(C)(C)C)CC3)ccc12]

0.2 mL of triethylamine and 0.1 mL of ethyl chlorocarbonate were added dropwise with stirring at 0° C. to a methanol (5 mL) solution of 300 mg of 6-(4-tert-butoxycarbonyl-1,4-diazepan-1-ylsulfonyl)isoquinoline 2-oxide, and the mixture was then stirred at room temperature for 3 hours. After the completion of reaction, the reaction solvent was distilled off under reduced pressure. To the obtained residue, 20 mL of ethyl acetate was added, and the deposited insoluble matter was removed by filtration. The filtrate was concentrated, and the obtained crude product was purified by silica gel column chromatography (ethyl acetate:hexane=1:1) to obtain 110 mg of the compound of interest as a white crystal (36%).

$^1$H-NMR spectrum (CDCl$_3$, δ ppm): 1.41 (s, 9H), 1.94-1.96 (m, 2H), 3.29-3.37 (m, 4H), 3.47-3.57 (m, 4H), 4.15 (s, 3H), 7.30 (d, J=6.0 Hz, 1H), 7.81 (d, J=8.5 Hz, 1H), 8.12 (d, J=6.0 Hz, 1H), 8.21 (s, 1H), 8.37 (d, J=8.5 Hz, 1H)

Step 3

Synthesis of 6-(1,4-diazepan-1-ylsulfonyl)isoquinolin-1(2H)-one (Compound 53)

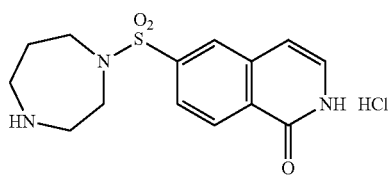 [SMILES: O=c1[nH]ccc2cc(S(=O)(=O)N3CCCNCC3)ccc12 ; Cl]

110 mg of 6-(4-tert-butoxycarbonyl-1,4-diazepan-1-ylsulfonyl)-1-methoxyisoquinoline was dissolved in 2 mL of 1,4-dioxane and 1.5 mL of water. 4 mL of a 4 M hydrochloric acid-dioxane solution was added dropwise thereto, and the mixture was then stirred at 90° C. for 16 hours. After the completion of reaction, the reaction solvent was distilled off. The obtained residue was dissolved in 5 mL of methanol, and 5 mL of ethyl acetate was then added with vigorous stirring. The deposited white crystal was collected by filtration and dried under reduced pressure to obtain 64 mg of the compound of interest as a white crystal (72%).

$^1$H-NMR spectrum (DMSO-d$_6$, δ ppm): 1.95-1.99 (m, 2H), 2.01 (br s, 1H), 3.13-3.17 (m, 4H), 3.34-3.36 (m, 2H), 3.54-3.60 (m, 2H), 6.74 (d, J=7.0 Hz, 1H), 7.32 (dd, J=7.0 Hz, 1H), 7.79 (d, J=8.5 Hz, 1H), 8.17 (s, 1H), 8.35 (d, J=8.5 Hz, 1H), 8.65 (br s, 1H), 11.5 (s, 1H)

mp: 266-267° C.

Example 54

Synthesis of 1-amino-6-(1,4-diazepan-1-ylsulfonyl)isoquinoline dihydrochloride (Compound 54)

Step 1

Synthesis of 1-amino-6-(4-tert-butoxycarbonyl-1,4-diazepan-1-ylsulfonyl)isoquinoline

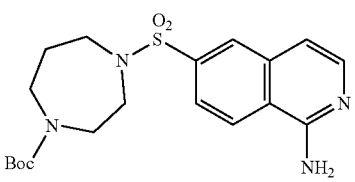 [SMILES: CC(C)(C)OC(=O)N1CCCN(S(=O)(=O)c2ccc3c(N)nccc3c2)CC1]

310 mg of p-toluenesulfonyl chloride was added to a pyridine (20 mL) solution of 510 mg of 6-(4-tert-butoxycarbonyl-1,4-diazepan-1-ylsulfonyl)isoquinoline 2-oxide obtained in Step 1 of Example 53, and the mixture was stirred at room temperature for 16 hours. Then, the reaction solvent was distilled off under reduced pressure. To the obtained residue, 9 mL of 2-ethanolamine was added, and the mixture was stirred at room temperature for 6 hours. After the completion of reaction, the reaction solution was poured into ice water, and the deposited white crystal was collected by filtration. The obtained crystal was purified by silica gel column chromatography (dichloromethane:methanol=30:1) to obtain 380 mg of the compound of interest as a white crystal (75%).

¹H-NMR spectrum (CDCl₃, δ ppm): 1.41 (s, 9H), 2.15-2.20 (m, 2H), 3.30-3.38 (m, 4H), 3.47-3.57 (m, 4H), 5.25 (s, 2H), 7.13 (d, J=6.0 Hz, 1H), 7.76 (d, J=8.5 Hz, 1H), 7.92 (d, J=8.5 Hz, 1H), 8.06 (d, J=6.0 Hz, 1H), 8.18 (s, 1H)

Step 2

Synthesis of 1-amino-6-(1,4-diazepan-1-ylsulfonyl)isoquinoline dihydrochloride (Compound 54)

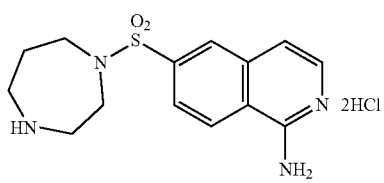 [SMILES: Nc1nccc2cc(S(=O)(=O)N3CCCNCC3)ccc12]

Compound 54 was synthesized (92%) according to the production method of Step 2 of Example 12 using 1-amino-6-(4-tert-butoxycarbonyl-1,4-diazepan-1-ylsulfonyl)isoquinoline instead of (S)-6-(4-tert-butoxycarbonyl-2-methyl-1,4-diazepan-1-ylsulfonyl)isoquinoline.

¹H-NMR spectrum (DMSO-d₆, δ ppm): 1.95-2.00 (m, 2H), 2.11 (br s, 1H), 3.15-3.18 (m, 4H), 3.36-3.41 (m, 2H), 3.55 (s, 2H), 3.60-3.64 (m, 2H), 7.40 (d, J=7.0 Hz, 1H), 7.82 (d, J=7.0 Hz, 1H), 8.07 (d, J=8.0 Hz, 1H), 8.26 (br s, 2H), 8.47 (s, 1H), 8.86 (d, J=8.0 Hz, 1H)
mp: 214-215° C.

Example 55

Synthesis of 1-nitrile-6-(1,4-diazepan-1-ylsulfonyl)isoquinoline dihydrochloride (Compound 55)

Step 1

Synthesis of 1-nitrile-6-(4-tert-butoxycarbonyl-1,4-diazepan-1-ylsulfonyl)isoquinoline

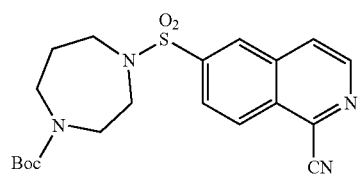 [SMILES: CC(C)(C)OC(=O)N1CCCN(S(=O)(=O)c2ccc3c(C#N)nccc3c2)CC1]

4 mL of distilled water was added to 450 mg of 6-(4-tert-butoxycarbonyl-1,4-diazepan-1-ylsulfonyl)isoquinoline 2-oxide obtained in Step 1 of Example 53, further 250 mg of potassium cyanide and 320 mg of benzoyl chloride were added, and the mixture was stirred at room temperature for 4 hours. After the completion of reaction, the reaction solution was subjected to three extractions with 10 mL of ethyl acetate. The organic layer was dried over anhydrous sodium sulfate and concentrated, and the obtained crude product was then purified by silica gel column chromatography (hexane:ethyl acetate=1:1) to obtain 313 mg of the compound of interest as a pale yellow solid (68%).

¹H-NMR spectrum (CDCl₃, δ ppm): 1.41 (s, 9H), 1.97 (br s, 2H), 3.38 (br s, 2H), 3.40 (br s, 2H), 3.50 (br s, 2H), 3.58 (br s, 2H), 8.03 (d, J=6.0 Hz, 1H), 8.06 (d, J=9.0 Hz, 1H), 8.45 (s, 1H), 8.49 (d, J=9.0 Hz, 1H), 8.80 (d, J=6.0 Hz, 1H)

Step 2

Synthesis of 1-nitrile-6-(1,4-diazepan-1-ylsulfonyl)isoquinoline dihydrochloride (Compound 55)

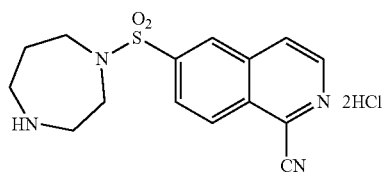 [SMILES: N#Cc1nccc2cc(S(=O)(=O)N3CCCNCC3)ccc12]

Compound 55 was obtained using 1-nitrile-6-(4-tert-butoxycarbonyl-1,4-diazepan-1-ylsulfonyl)isoquinoline instead of 6-(4-tert-butoxycarbonylpiperazin-1-ylsulfonyl)isoquinoline in Step 2 of Example 1.

¹H-NMR spectrum (D₂O, δ ppm): 2.11-2.13 (m, 2H), 3.36-3.42 (m, 4H), 3.48 (t. J=6.0 Hz, 2H), 3.69 (t. J=6.0 Hz, 2H), 8.11 (d, J=8.5 Hz, 1H), 8.27 (d, J=6.0 Hz, 1H), 8.46 (d, J=8.5 Hz, 1H), 8.59 (s, 1H), 8.71 (d, J=8.5 Hz, 1H)

Example 56

Synthesis of (S)-6-{2-(4-aminobutyl)-1,4-diazepan-1-ylsulfonyl}isoquinoline trihydrochloride (Compound 56)

Step 1

Synthesis of (S)-6-{4-tert-butoxycarbonyl-2-(4-tert-butoxycarbonylaminobutyl)-1,4-diazepan-1-ylsulfonyl}isoquinoline

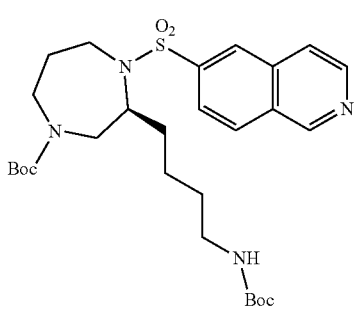 [SMILES: CC(C)(C)OC(=O)NCCCC[C@H]1CN(C(=O)OC(C)(C)C)CCCN1S(=O)(=O)c1ccc2cnccc2c1]

The compound of interest was synthesized according to the production method of Step 1 of Example 12 using Reference Compound 34 instead of Reference Compound 10.

¹H-NMR spectrum (CDCl₃, δ ppm): 1.11-1.27 (m, 2H), 1.35-1.37 (m, 2H), 1.46 (s, 9H), 1.40 (S, 9H), 1.70-2.05 (m, 4H), 2.87-3.03 (m, 3H), 3.30-3.65 (m, 4H), 3.81-3.88 (m, 1H), 4.09-4.21 (m, 1H), 4.60 (br s, 1H), 7.78 (d, J=6.0 Hz, 1H), 7.92 (d, J=8.5 Hz, 1H), 8.11 (d, J=8.5 Hz, 1H), 8.39 (s, 1H), 8.67 (d, J=6.0 Hz, 1H), 9.35 (s, 1H)

Step 2

Synthesis of (S)-6-{2-(4-aminobutyl)-1,4-diazepan-1-ylsulfonyl}isoquinoline trihydrochloride (Compound 56)

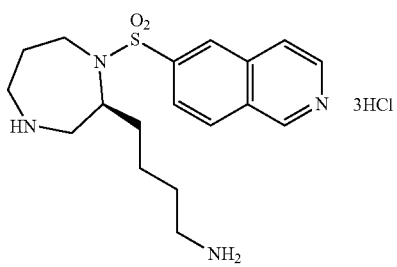 [SMILES: NCCCC[C@H]1CNCCCN1S(=O)(=O)c1ccc2cnccc2c1]

Compound 56 was synthesized according to the production method of Step 2 of Example 12 using (S)-6-(4-tert-butoxycarbonyl-2-(4-tert-butoxycarbonylaminobutyl)-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 1.04-1.14 (m, 2H), 1.31-1.48 (m, 3H), 1.56-1.61 (m, 1H), 1.83-1.93 (m, 2H), 2.48-2.50 (m, 2H), 3.03-3.07 (m, 2H), 3.25-3.32 (m, 3H), 3.75-3.80 (m, 1H), 4.30-4.32 (m, 1H), 7.90 (m, 2H), 8.17 (d, J=8.5 Hz, 1H), 8.31 (s, 1H), 8.49 (d, J=8.5 Hz, 1H), 8.72 (s, 1H)

mp: 38-40° C.

$[α]^{25}_D$ −22.9 (c=0.0483, H$_2$O)

Example 57

Synthesis of 6-(4-methoxycarbonylpiperidin-1-ylsulfonyl)isoquinoline hydrochloride (Compound 57)

Step 1

Synthesis of 6-(4-methoxycarbonylpiperidin-1-ylsulfonyl)isoquinoline

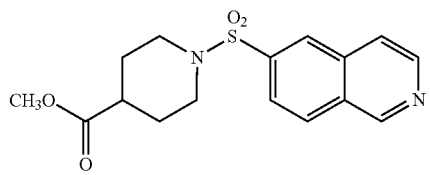

The compound of interest was synthesized using methyl isonipecotate instead of tert-butoxycarbonylpiperazine in Step 1 of Example 1.

$^1$H-NMR spectrum (CDCl$_3$, δ ppm): 1.80-1.87 (m, 2H), 1.96-2.00 (m, 2H), 2.27-2.31 (m, 1H), 2.61-2.66 (m, 2H), 3.64 (s, 3H), 3.69-3.72 (m, 2H), 7.78 (d, J=6.0 Hz, 1H), 7.88 (d, J=8.5 Hz, 1H), 8.13 (d, J=8.5 Hz, 1H), 8.31 (s, 1H), 8.69 (d, J=6.0 Hz, 1H), 9.38 (s, 1H)

Step 2

Synthesis of 6-(4-methoxycarbonylpiperidin-1-ylsulfonyl)isoquinoline hydrochloride

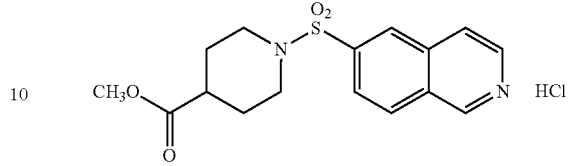

Compound 57 was obtained using 6-(4-methoxycarbonylpiperidin-1-ylsulfonyl)isoquinoline instead of 6-(4-tert-butoxycarbonylpiperazin-1-ylsulfonyl)isoquinoline in Step 2 of Example 1.

$^1$H-NMR spectrum (D$_2$O, δ ppm): 1.61-1.69 (m, 2H), 1.94-1.97 (m, 2H), 2.39-2.43 (m, 1H), 2.68-2.73 (m, 2H), 3.60 (s, 3H), 3.74-3.77 (m, 2H), 8.23 (d, J=7.8 Hz, 1H), 8.58 (d, J=7.8 Hz, 1H), 8.65-8.67 (m, 2H), 8.73 (s, 1H), 9.79 (s, 1H)

Example 58

Synthesis of (S)-6-(3-hydroxypyrrolidin-1-ylsulfonyl)isoquinoline hydrochloride (Compound 58)

Step 1

Synthesis of (S)-6-(3-hydroxypyrrolidin-1-ylsulfonyl)isoquinoline

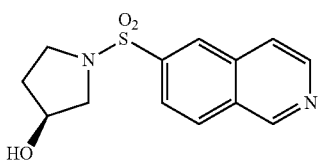 [SMILES: O=S(=O)(c1ccc2cnccc2c1)N1CC[C@H](O)C1]

The compound of interest was synthesized using (S)-3-hydroxypyrrolidine instead of tert-butoxycarbonylpiperazine in Step 1 of Example 1.

$^1$H-NMR spectrum (CDCl$_3$, δ ppm): 1.95-2.01 (m, 2H), 3.34-3.43 (m, 1H), 3.44-3.55 (m, 3H), 4.42 (br s 1H), 7.78 (d, J=5.5 Hz, 1H), 7.98 (d, J=9.0 Hz, 1H), 8.11 (d, J=9.0 Hz, 1H), 8.38 (s, 1H), 8.65 (d, J=5.5 Hz, 1H), 9.32 (s, 1H)

Step 2

Synthesis of (S)-6-(3-hydroxypyrrolidin-1-ylsulfonyl)isoquinoline hydrochloride

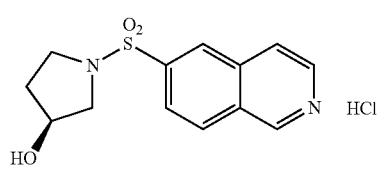 [SMILES: O=S(=O)(c1ccc2cnccc2c1)N1CC[C@H](O)C1 ; Cl]

Compound 58 was obtained using (S)-6-(3-hydroxypyrrolidin-1-ylsulfonyl)isoquinoline instead of 6-(4-tert-butoxycarbonylpiperazin-1-ylsulfonyl)isoquinoline in Step 2 of Example 1.

$^1$H-NMR spectrum (D$_2$O, δ ppm): 1.63-1.76 (m, 2H), 3.14 (d, J=11.0 Hz, 1H), 3.26-3.40 (m, 3H), 4.13-4.14 (m, 1H), 8.14 (d, J=9.0 Hz, 1H), 8.45 (d, J=5.5 Hz, 1H), 8.54 (d, J=9.0 Hz, 1H), 8.69 (s, 1H), 8.76 (br s, 1H), 9.80 (br s, 1H)

Example 59

Synthesis of 5-phenyl-6-(1,4-diazepan-1-ylsulfonyl)isoquinoline dihydrochloride (Compound 59)

Step 1

Synthesis of 5-phenyl-6-(4-tert-butoxycarbonyl-1,4-diazepan-1-ylsulfonyl)isoquinoline

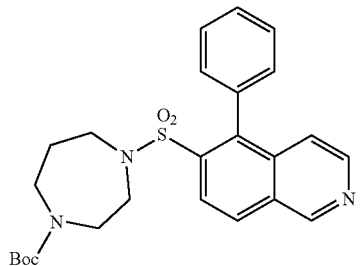 [SMILES: CC(C)(C)OC(=O)N1CCCN(S(=O)(=O)c2ccc3cnccc3c2-c2ccccc2)CC1]

10 mL of toluene was added to a mixture of 146 mg of 5-bromo-6-(4-tert-butoxycarbonyl-1,4-diazepan-1-ylsulfonyl)isoquinoline obtained in the course of Example 5, 50 mg of phenylboronic acid, 80 mg of tetrakis(triphenylphosphine) palladium, and 600 mg of potassium phosphate, and the mixture was stirred at 120° C. for 12 hours in a nitrogen atmosphere. After the completion of reaction, distilled water was added, followed by three extractions with ethyl acetate. The organic layer was washed with saturated saline, dried over anhydrous sodium sulfate, and concentrated. The obtained crude product was purified by silica gel column chromatography (hexane:ethyl acetate=3:1 to 2:1) to obtain 114 mg of the compound of interest as a white solid.

$^1$H-NMR spectrum (CDCl$_3$, δ ppm): 1.43 (s, 9H), 1.75-1.79 (m, 2H), 2.66-2.77 (m, 4H), 3.35-3.46 (m, 4H), 7.12 (d, J=6.0 Hz, 1H), 7.31-7.32 (m, 2H), 7.53-7.54 (m, 3H), 8.12 (d, J=8.0 Hz, 1H), 8.32 (d, J=8.0 Hz, 1H), 8.47 (d, J=6.0 Hz, 1H), 9.36 (s, 1H)

Step 2

Synthesis of 5-phenyl-6-(1,4-diazepan-1-ylsulfonyl)isoquinoline dihydrochloride (Compound 59)

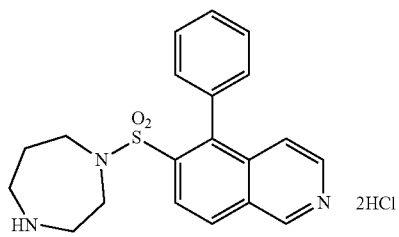 [SMILES: O=S(=O)(c1ccc2cnccc2c1-c1ccccc1)N1CCCNCC1]

Compound 59 was synthesized according to the production method of Step 2 of Example 12 using 5-phenyl-6-(4-tert-butoxycarbonyl-1,4-diazepan-1-ylsulfonyl)isoquinoline instead of (S)-6-(4-tert-butoxycarbonyl-2-methyl-1,4-diazepan-1-ylsulfonyl)isoquinoline.

$^1$H-NMR spectrum (D$_2$O, δ ppm): 1.85-1.90 (m, 2H), 2.95-2.99 (m, 4H), 3.09-3.11 (m, 2H), 3.20-3.24 (m, 2H), 7.33-7.35 (m, 2H), 7.50-7.54 (m, 3H), 7.70 (d, J=6.0 Hz, 1H), 8.37 (d, J=8.5 Hz, 1H), 8.49 (d, J=8.5 Hz, 1H), 8.83 (d, J=6.0 Hz, 1H), 9.35 (s, 1H)

Evaluation of Biological Activity

Evaluation Example 1

Blood Pressure Lowering Effect of Compound of the Present Invention in Rats

The compound of the present invention was intraperitoneally administered to rats (SD, sex: male, 6 rats per group) and evaluated for its blood pressure lowering effect. Example 18 was used as a test compound.
(Preparation of Test Compound Solution)
The test compound was dissolved in saline and diluted to prepare a test compound solution with a predetermined concentration.
(Test Method)
The test drug was intraperitoneally administered at a dose of 10 mg/kg to the rats (6 rats per group), and their blood pressures and pulse rates were measured over time using Softron Indirect Blood Pressure Meter BP-98A.
(Results)
The systolic blood pressures of the animals receiving the compound of the present invention were lowered by up to 30% or more compared with the value before administration, showing that the compound of the present invention has excellent blood pressure lowering effect. Moreover, the pulse rates measured simultaneously therewith were increased. This was confirmed to be pulse rate increase that compensated for blood pressure lowering caused by vasodilation. These results demonstrated that the compounds of the present invention are useful as therapeutic agents for cardiovascular diseases including hypertension.

Evaluation Example 2

Blood Pressure Lowering Effect of Compound of the Present Invention in Spontaneously Hypertensive Rats The compound of the present invention was intraperitoneally administered to spontaneously hypertensive rats (SHR/Izm, sex: male, 4 to 6 rats per group) and evaluated for its blood pressure lowering effect. Examples 32, 34, and 35 were used as test compounds.
(Preparation of Test Compound Solution)
Each test compound was dissolved in saline and diluted to prepare a test compound solution with a predetermined concentration.
(Test Method)
The test drug was intraperitoneally administered at a dose of 10 mg/kg (except for 30 mg/kg for Example 34) to the animals (4 to 6 rats per group), and their blood pressures and pulse rates were measured over time using Softron Indirect Blood Pressure Meter BP-98A.

(Results)

The systolic blood pressures of the animals receiving the compound of the present invention were lowered by up to 30% or more (Examples 34 and 35) compared with the value before administration. Example 32 lowered them by 16%. It was thus shown that the compound of the present invention has excellent blood pressure lowering effect. Moreover, the pulse rates measured simultaneously therewith were increased. This was confirmed to be pulse rate increase that compensated for blood pressure lowering caused by vasodilation. These results demonstrated that the compounds of the present invention are useful as therapeutic agents for cardiovascular diseases including hypertension.

Evaluation Example 3

Ocular Hypotensive Effect of Compound of the Present Invention in Rabbits

The compound of the present invention was administered to rabbits (New Zealand White, sex: male, 3 to 7 per group) and evaluated for its ocular hypotensive effect.
(Preparation of Test Compound Solution)

Each test compound was dissolved in a vehicle (1.04 g of sodium dihydrogen phosphate dihydrate and 0.5 g of sodium chloride dissolved in purified water and then adjusted to pH 7.0 with sodium hydroxide to make the total amount to 100 mL) to prepare a test compound solution with a concentration of 10 (W/V).
(Test Method)

The intraocular pressures of the rabbits were measured using Tiolat TonoVet handheld tonometer immediately before administration of test compound. The test compound solution and the vehicle were dropped at a volume of 0.04 mL to one eye and the contralateral eye, respectively, and the intraocular pressures were measured over time in the same way as above. The rate of the intraocular pressure of the eye receiving the test compound solution to that of the eye receiving the vehicle was calculated as an ocular hypotensive rate.
(Results)

The maximum ocular hypotensive rate of each test compound is shown in Table 1. As shown in Table 1, all the compounds of the present invention exhibited excellent ocular hypotensive effect. This demonstrated that the compounds of the present invention are useful as therapeutic drugs for glaucoma.

TABLE 1

Ocular hypotensive effects of compounds of the present invention

| Example No. | Maximum ocular hypotensive rate |
| --- | --- |
| 1 | ++ |
| 2 | ++ |
| 3 | ++ |
| 4 | + |
| 5 | ++ |
| 6 | + |
| 7 | ++ |
| 8 | ++ |
| 9 | + |
| 10 | + |
| 12 | ++ |
| 13 | ++ |
| 14 | ++ |
| 15 | ++ |
| 16 | ++ |
| 17 | ++ |
| 18 | ++ |
| 19 | ++ |
| 20 | ++ |
| 21 | ++ |
| 22 | ++ |
| 23 | ++ |
| 24 | ++ |
| 25 | ++ |
| 26 | ++ |
| 27 | ++ |
| 28 | ++ |
| 29 | ++ |
| 30 | ++ |
| 31 | ++ |
| 32 | ++ |
| 33 | ++ |
| 34 | ++ |
| 35 | ++ |
| 36 | ++ |
| 37 | ++ |
| 38 | ++ |
| 39 | ++ |
| 40 | ++ |
| 41 | ++ |
| 42 | ++ |
| 43 | ++ |
| 44 | ++ |
| 45 | + |
| 47 | + |
| 48 | + |
| 49 | ++ |
| 51* | ++ |
| 52* | ++ |

+: 5-15% ocular hypotensive rate
++: 15% or more ocular hypotensive rate
*: test compound concentration of 2%

Evaluation Example 4

Neurite Outgrowth Promoting Effect

To examine the usefulness of the compound of the present invention as a therapeutic agent for neurodegenerative diseases, NG108-15 cells frequently used as a model of neurons were cultured in the presence of the compound of the present invention, which was then evaluated for its neurite outgrowth promoting effect. Examples 15 and 49 were used as test compounds.
(Preparation of Test Compound Solution)

Each test compound was dissolved in dimethyl sulfoxide and diluted to prepare a test compound solution with a predetermined concentration.
(Test Method)

The NG108-15 cells (obtained from ATCC) were cultured in a Dulbecco's modified eagle's medium containing 5% fetal bovine serum and 1×HAT (hypoxanthine, aminopterin, and thymidine). The cells were inoculated at 12,000 cells/well to a 24-well plate and statically cultured at 37° C. for 12 hours in an environment of 5% $CO_2$ and 95% air. Then, each test compound was added at a final concentration of 10, 3, 1, or 0.3 μmol/L. 24 hours later, the degree of neurite outgrowth was observed under an inverted microscope.
(Results)

The NG108-15 cells cultured in the compound-supplemented culture solution were confirmed to have remarkable neurite outgrowth compared with the cells cultured in the absence of the compound. This demonstrated that the compound of the present invention has neurite outgrowth promoting effect.

Evaluation Example 5

Motor Function Recovering Effect of Compound of the Present Invention on a Spinal Cord Injury Model of the Mouse To examine the usefulness of the compound of the present invention as a therapeutic agent for spinal cord injury, the mouse model of spinal cord injury was prepared and a motor function recovering effect after spinal cord injury was investigated.

(Preparation of Test Compound Solution)

Example 14 as a test compound was dissolved in saline and diluted to prepare a test compound solution with a predetermined concentration.

(Test Method)

C57BL/6Cr mice (female, body weight: around 19 g, 6 to 8 rats per group) were anesthetized by halothane inhalation. The spinal cord at the level of the eighth thoracic vertebrae was compressed with 20 g of weight for 5 minutes to prepare a spinal cord injury model, according to the method described in the document (Acta Neuropathol. 100, 13-22 (2000)). The test compound was intraperitoneally administered at a dose of 3 mg/kg once a day for 7 consecutive days from the surgery day. After 1, 4, 7, 10, and 14 days from the preparation of the spinal cord injury model, the severity of neurological dysfunction was scored by a partial modification of the performance score described in J. Neurosurg. 93 (Spine 1), 94-101 (2000). The details of the behavioral score are as follows:

Open field locomotion (rated 0 to 42)
Toe spread (rated 0 to 5)
Contact place response (rated 0 to 5)
Withdrawal reflexes (rated 0 to 5 for each reflex to extension, pain, and pressure stimulations)
Righting reflex (rated 0 to 5)

According to this score, normal animals are given 0, whereas animals with the most serious disorder are given 72.

(Results)

The neurological dysfunction score of each group on day 14 after operation was 41 in the group receiving saline, whereas it was 33 in the group receiving the test compound. The compound of the present invention exhibited effect of recovering motor function after spinal cord injury. This demonstrated that the compounds of the present invention are useful as pharmaceuticals for spinal cord injury.

The invention claimed is:

1. An isoquinoline-6-sulfonamide compound of Formula (1), a salt thereof, or a solvate of the compound or the salt:

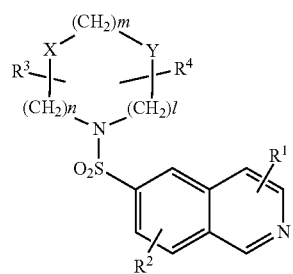

(1)

wherein

X and Y each independently is a direct bond, NH, CH=CH, O, or S;

$R^1$ and $R^2$ each independently is a hydrogen atom, a halogen atom, a cyano group, an alkyl group, a halogenoalkyl group, an alkenyl group, an alkoxy group, an alkylthio group, a hydroxyl group, a mercapto group, a nitro group, an aryl group, an amino group, or an aminoalkylthio group;

$R^3$ and $R^4$ each independently is a hydrogen atom, an alkyl group, an alkenyl group, an amino group, an alkylamino group, a dialkylamino group, an aminoalkyl group, a halogenoalkyl group, an alkanoyl group, an aminoalkanoyl group, an alkylaminoalkanoyl group, an alkoxycarbonyl group, a hydroxyl group, or a mercapto group, or $R^3$ and $R^4$ together form an alkylene group or an alkenylene group, which may be bridged between two carbon atoms to an arbitrary position; and l, m, and n represent an integer number of 1 to 4.

2. The compound, salt, or solvate of claim 1, wherein in Formula (1),

X and Y are each independently a direct bond, NH, CH=CH, O, or S;

$R^1$ and $R^2$ are each independently a hydrogen atom, a halogen atom, a cyano group, a $C_{1-3}$ alkyl group, a halogeno $C_{1-8}$ alkyl group, a $C_{2-8}$ alkenyl group, a $C_{1-8}$ alkoxy group, a $C_{1-8}$ alkylthio group, a hydroxyl group, a mercapto group, a nitro group, a phenyl group, an amino group, or an amino $C_{1-8}$ alkylthio group;

$R^3$ and $R^4$ are each independently a hydrogen atom, a $C_{1-8}$ alkyl group, a $C_{2-8}$ alkenyl group, an amino group, an amino $C_{1-8}$ alkyl group, a halogeno $C_{1-8}$ alkyl group, a $C_{1-8}$ alkylamino group, a di-$C_{1-8}$ alkylamino group, a $C_{2-8}$ alkanoyl group, an amino $C_{2-8}$ alkanoyl group, a $C_{1-8}$ alkoxycarbonyl group, a hydroxyl group, or a mercapto group, or $R^3$ and $R^4$ together form a bridged $C_{1-3}$ alkylene group or alkenylene group;

l and m are each independently 1 to 3; and n is 2 or 3.

3. The compound, salt, or solvate of claim 1, wherein in Formula (1),

X is a direct bond or NH;

Y is a direct bond, NH, CH=CH, or O;

$R^1$ and $R^2$ are each independently a hydrogen atom, a halogen atom, a $C_{1-8}$ alkyl group, a nitro group, a cyano group, a hydroxyl group, a halogeno $C_{1-8}$ alkyl group, a phenyl group, or an amino $C_{1-8}$ alkylthio group;

$R^3$ and $R^4$ are a hydrogen atom, a $C_{1-8}$ alkyl group, an amino group, a $C_{1-8}$ alkylamino group, an amino $C_{1-8}$ alkyl group, a halogeno $C_{1-8}$ alkyl group, an amino $C_{1-8}$ alkanoyl group, a $C_{1-8}$ alkylamino group, or a $C_{1-8}$ alkanoyl group, or $R^3$ and $R^4$ together form a bridged $C_{1-3}$ alkylene group;

l and m are each independently 1 to 3; and n is 2 or 3.

4. The compound, salt, or solvate of claim 1, wherein in Formula (1),

X is a direct bond or NH;

Y is a direct bond, NH, CH=CH, or O;

$R^1$ and $R^2$ are each independently a hydrogen atom, a halogen atom, a nitro group, an aminoalkylthio group, a $C_{1-6}$ alkyl group, or a halogeno $C_{1-6}$ alkyl group;

$R^3$ and $R^4$ are a hydrogen atom, a $C_{1-6}$ alkyl group, a halogeno $C_{1-6}$ alkyl group, an amino group, a $C_{1-8}$ alkylamino group, or an amino $C_{1-8}$ alkanoyl group, or $R^3$ and $R^4$ together form a bridged $C_{1-3}$ alkylene group;

l and m are each independently 1 to 3; and n is 2 or 3.

5. The compound, salt, or solvate of claim 1, wherein in Formula (1),

X is a direct bond or NH;
Y is a direct bond, CH=CH, or O;
R¹ and R² are each independently a hydrogen atom, a halogen atom, an aminoalkylthio group, or a $C_{1-6}$ alkyl group;
R³ and R⁴ are a hydrogen atom, a $C_{1-6}$ alkyl group, a halogeno $C_{1-6}$ alkyl group, or an amino group, or R³ and R⁴ together form a bridged $C_{1-3}$ alkylene group;
l and m are each independently 1 to 3; and
n is 2 or 3.

6. A compound selected from the group consisting of the following, a salt thereof, or a solvate thereof:
6-(piperazin-1-ylsulfonyl)isoquinoline,
(R)-6-(3-aminopyrrolidin-1-ylsulfonyl)isoquinoline,
6-(1,4-diazepan-1-ylsulfonyl)isoquinoline,
6-(4-aminopiperidin-1-ylsulfonyl)isoquinoline,
5-bromo-6-(1,4-diazepan-1-ylsulfonyl)isoquinoline,
6-(1,4-diazepan-1-ylsulfonyl)-8-fluoroisoquinoline,
6-{(1S,4S)-2,5-diazabicyclo[2.2.1]heptan-2-ylsulfonyl}isoquinoline,
(R,Z)-6-(2-methyl-2,3,4,5-tetrahydro-1,4-diazocin-1(8H)-ylsulfonyl)isoquinoline,
6-(morpholin-1-ylsulfonyl)isoquinoline,
(S)-6-{3-(N-methylamino)pyrrolidin-1-ylsulfonyl}isoquinoline,
(S)-6-{3-(N-butylamino)pyrrolidin-1-ylsulfonyl}isoquinoline,
(S)-6-(2-methyl-1,4-diazepan-1-ylsulfonyl)isoquinoline,
(S)-6-(2-methylpiperazin-1-ylsulfonyl)isoquinoline,
(R)-6-(2-methyl-1,4-diazocan-1-ylsulfonyl)isoquinoline,
(S)-5-bromo-6-(2-methyl-1,4-diazepan-1-ylsulfonyl)isoquinoline,
6-(3-methyl-1,4-diazepan-1-ylsulfonyl)isoquinoline,
6-(7-methyl-1,4-diazepan-1-ylsulfonyl)isoquinoline,
(R)-6-(2-methyl-1,4-diazepan-1-ylsulfonyl)isoquinoline,
(R)-6-(2-ethyl-1,4-diazepan-1-ylsulfonyl)isoquinoline,
(R)-6-(2-ethyl-1,4-diazocan-1-ylsulfonyl)isoquinoline,
6-(1,4-diazocan-1-ylsulfonyl)isoquinoline,
6-(2,2-dimethyl-1,4-diazepan-1-ylsulfonyl)isoquinoline,
(R)-5-bromo-6-(2-methyl-1,4-diazocan-1-ylsulfonyl)isoquinoline,
(S)-6-(2-methyl-1,4-diazocan-1-ylsulfonyl)isoquinoline,
(R)-6-(2-methyl-1,4-diazepan-1-ylsulfonyl)-7-fluoroisoquinoline,
(S)-6-(2-fluoromethyl-1,4-diazepan-1-ylsulfonyl)isoquinoline,
(S)-6-(2-methyl-1,4-diazepan-1-ylsulfonyl)isoquinoline,
(R)-5-bromo-6-(2-methyl-1,4-diazepan-1-ylsulfonyl)isoquinoline,
(R)-6-(6-methyl-1,4-diazocan-1-ylsulfonyl)isoquinoline,
(R)-6-(7-methyl-1,4-diazocan-1-ylsulfonyl)isoquinoline,
(S)-6-(7-methyl-1,4-diazepan-1-ylsulfonyl)isoquinoline,
(R)-6-(2-methyl-1,4-diazonan-1-ylsulfonyl)isoquinoline,
(R)-6-(7-methyl-1,4-diazepan-1-ylsulfonyl)isoquinoline,
(2R,7R)-6-(2,7-dimethyl-1,4-diazepan-1-ylsulfonyl)isoquinoline,
(2S,7R)-6-(2,7-dimethyl-1,4-diazepan-1-ylsulfonyl)isoquinoline,
(R)-6-(8-methyl-1,4-diazocan-1-ylsulfonyl)isoquinoline,
(R)-6-(2-methyl-1,5-diazocan-1-ylsulfonyl)isoquinoline,
(R)-6-(2-methyl-1,4-diazocan-1-ylsulfonyl)-5-nitroisoquinoline,
(2R,6R)-6-(2,6-dimethylpiperazin-1-ylsulfonyl)isoquinoline,
(2S,7S)-6-(2,7-dimethyl-1,4-diazepan-1-ylsulfonyl)isoquinoline,
(S)-6-(2-methyl-1,5-diazocan-1-ylsulfonyl)isoquinoline,
(R)-6-(5-methyl-1,4,7-oxadiazonan-4-ylsulfonyl)isoquinoline,
(R)-6-(2-methyl-1,4,7-triazonan-1-ylsulfonyl)isoquinoline,
6-(4-glycyl-1,4-diazepan-1-ylsulfonyl)isoquinoline,
(S)-6-(4-glycyl-2-methyl-1,4-diazepan-1-ylsulfonyl)isoquinoline,
(R)-6-(4-glycyl-2-methyl-1,4-diazocan-1-ylsulfonyl)isoquinoline,
(R)-6-(4-sarkosyl-2-methyl-1,4-diazocan-1-ylsulfonyl)isoquinoline,
(S)-5-methyl-6-(2-methyl-1,4-diazepan-1-ylsulfonyl)isoquinoline,
(S)-1-(2-aminoethylthio)-6-(2-methyl-1,4-diazepan-1-ylsulfonyl)isoquinoline,
(R)-1-(2-aminoethylthio)-6-(7-methyl-1,4-diazepan-1-ylsulfonyl)isoquinoline,
(R)-1-(2-aminoethylthio)-6-(2-methyl-1,4-diazocan-1-ylsulfonyl)isoquinoline,
6-(1,4-diazepan-1-ylsulfonyl)isoquinolin-1(2H)-one,
1-amino-6-(1,4-diazepan-1-ylsulfonyl)isoquinoline,
1-nitrile-6-(1,4-diazepan-1-ylsulfonyl)isoquinoline,
(S)-6-(2-(4-aminobutyl)-1,4-diazepin-1-ylsulfonyl)isoquinoline,
6-(4-methoxycarbonylpiperidin-1-ylsulfonyl)isoquinoline,
(S)-6-(3-hydroxypyrrolidin-1-ylsulfonyl)isoquinoline, and
5-phenyl-6-(1,4-diazepan-1-ylsulfonyl)isoquinoline.

7. A pharmaceutical composition, comprising:
the compound, salt, or solvate of claim 1; and
a diluent.

8. A method for treating glaucoma, hypertension, or spinal cord injury the method comprising:
administering an effective amount of a composition comprising the compound, salt, or solvate of claim 1.

9. The compound, salt, or solvate of claim 2, wherein in Formula (1),
X is a direct bond or NH;
Y is a direct bond, NH, CH=CH, or O;
R¹ and R² are each independently a hydrogen atom, a halogen atom, a $C_{1-8}$ alkyl group, a nitro group, a cyano group, a hydroxyl group, a halogeno $C_{1-8}$ alkyl group, a phenyl group, or an amino $C_{1-8}$ alkylthio group;
R³ and R⁴ are a hydrogen atom, a $C_{1-8}$ alkyl group, an amino group, a $C_{1-8}$ alkylamino group, an amino $C_{1-8}$ alkyl group, a halogeno $C_{1-8}$ alkyl group, an amino $C_{1-8}$ alkanoyl group, a $C_{1-8}$ alkylamino group, or a $C_{1-8}$ alkanoyl group, or R³ and R⁴ together form a bridged $C_{1-3}$ alkylene group;
l and m are each independently 1 to 3; and
n is 2 or 3.

10. The compound, salt, or solvate of claim 2, wherein in Formula (1),
X is a direct bond or NH;
Y is a direct bond, NH, CH=CH, or O;
R¹ and R² are each independently a hydrogen atom, a halogen atom, a nitro group, an aminoalkylthio group, a $C_{1-6}$ alkyl group, or a halogeno $C_{1-6}$ alkyl group;
R³ and R⁴ are a hydrogen atom, a $C_{1-6}$ alkyl group, a halogeno $C_{1-6}$ alkyl group, an amino group, a $C_{1-8}$ alkylamino group, or an amino $C_{1-8}$ alkanoyl group, or R³ and R⁴ together form a bridged $C_{1-3}$ alkylene group;
l and m are each independently 1 to 3; and
n is 2 or 3.

11. The compound, salt, or solvate of claim 3, wherein in Formula (1),

X is a direct bond or NH;
Y is a direct bond, NH, CH=CH, or O;
R$^1$ and R$^2$ are each independently a hydrogen atom, a halogen atom, a nitro group, an aminoalkylthio group, a C$_{1-6}$ alkyl group, or a halogeno C$_{1-6}$ alkyl group;
R$^3$ and R$^4$ are a hydrogen atom, a C$_{1-6}$ alkyl group, a halogeno C$_{1-6}$ alkyl group, an amino group, a C$_{1-8}$ alkylamino group, or an amino C$_{1-8}$ alkanoyl group, or R$^3$ and R$^4$ together form a bridged C$_{1-3}$ alkylene group;
l and m are each independently 1 to 3; and
n is 2 or 3.

12. The compound, salt, or solvate of claim 2, wherein in Formula (1),
X is a direct bond or NH;
Y is a direct bond, CH=CH, or O;
R$^1$ and R$^2$ are each independently a hydrogen atom, a halogen atom, an aminoalkylthio group, or a C$_{1-6}$ alkyl group;
R$^3$ and R$^4$ are a hydrogen atom, a C$_{1-6}$ alkyl group, a halogeno C$_{1-6}$ alkyl group, or an amino group, or R$^3$ and R$^4$ together form a bridged C$_{1-3}$ alkylene group;
l and m are each independently 1 to 3; and
n is 2 or 3.

13. The compound, salt, or solvate of claim 3, wherein in Formula (1),
X is a direct bond or NH;
Y is a direct bond, CH=CH, or O;
R$^1$ and R$^2$ are each independently a hydrogen atom, a halogen atom, an aminoalkylthio group, or a C$_{1-6}$ alkyl group;
R$^3$ and R$^4$ are a hydrogen atom, a C$_{1-6}$ alkyl group, a halogeno C$_{1-6}$ alkyl group, or an amino group, or R$^3$ and R$^4$ together form a bridged C$_{1-3}$ alkylene group;
l and m are each independently 1 to 3; and
n is 2 or 3.

14. The compound, salt, or solvate of claim 4, wherein in Formula (1),
X is a direct bond or NH;
Y is a direct bond, CH=CH, or O;
R$^1$ and R$^2$ are each independently a hydrogen atom, a halogen atom, an aminoalkylthio group, or a C$_{1-6}$ alkyl group;
R$^3$ and R$^4$ are a hydrogen atom, a C$_{1-6}$ alkyl group, a halogeno C$_{1-6}$ alkyl group, or an amino group, or R$^3$ and R$^4$ together form a bridged C$_{1-3}$ alkylene group;
l and m are each independently 1 to 3; and
n is 2 or 3.

\* \* \* \* \*

UNITED STATES PATENT AND TRADEMARK OFFICE
CERTIFICATE OF CORRECTION

PATENT NO. : 8,951,997 B2
APPLICATION NO. : 13/265246
DATED : February 10, 2015
INVENTOR(S) : Hiroyoshi Hidaka et al.

It is certified that error appears in the above-identified patent and that said Letters Patent is hereby corrected as shown below:

In the Claims

Column 102, Claim 2, line 22, "$C_{1-3}$" should read --$C_{1-8}$--.

Column 103, Claim 6, line 47, "(S)-6-(2-methyl-1, 4-diazepan-1-ylsulfonyl)isoquinoline," should read
--(S)-6-(2-fluoromethyl-1,4-diazocan-1-ylsulfonyl)isoquinoline, (S)-6-(2-methyl-1,4-diazonan-1-ylsulfonyl)isoquinoline,--.

Signed and Sealed this
Second Day of June, 2015

Michelle K. Lee
*Director of the United States Patent and Trademark Office*